United States Patent
Zass

(10) Patent No.: US 10,516,938 B2
(45) Date of Patent: Dec. 24, 2019

(54) SYSTEM AND METHOD FOR ASSESSING SPEAKER SPATIAL ORIENTATION

(71) Applicant: Ron Zass, Kiryat Tivon (IL)

(72) Inventor: Ron Zass, Kiryat Tivon (IL)

( * ) Notice: Subject to any disclaimer, the term of this patent is extended or adjusted under 35 U.S.C. 154(b) by 15 days.

(21) Appl. No.: 15/650,916

(22) Filed: Jul. 16, 2017

(65) Prior Publication Data

US 2018/0020285 A1 Jan. 18, 2018

Related U.S. Application Data

(60) Provisional application No. 62/363,261, filed on Jul. 16, 2016, provisional application No. 62/444,709, (Continued)

(51) Int. Cl.
| | |
|---|---|
| H04R 1/40 | (2006.01) |
| H04R 1/26 | (2006.01) |
| G06K 9/00 | (2006.01) |
| G16H 50/70 | (2018.01) |
| A61N 1/36 | (2006.01) |

(Continued)

(52) U.S. Cl.
CPC ............... *H04R 1/406* (2013.01); *A61B 5/16* (2013.01); *A61N 1/36082* (2013.01); *G06F 17/20* (2013.01); *G06F 17/21* (2013.01); *G06K 9/00275* (2013.01); *G06K 9/00369* (2013.01); *G10L 15/1822* (2013.01); *G10L 17/005* (2013.01); *G10L 17/26* (2013.01); *G10L 21/0205* (2013.01); *G10L 21/028* (2013.01); *G10L 21/0224* (2013.01); *G10L 25/63* (2013.01); *G10L 25/72* (2013.01); *G16H 50/70* (2018.01); *H04R 1/265* (2013.01); *H04R 3/005* (2013.01); *H04R 25/407* (2013.01); *A61B 5/02055* (2013.01); *A61B 5/1114* (2013.01); *A61B 5/1128* (2013.01); *A61B 2562/0204* (2013.01); *A61B 2562/0219* (2013.01); *G01N 2800/28* (2013.01); *G06K 9/00228* (2013.01); *G06K 9/00362* (2013.01); *G06K 9/46* (2013.01);
(Continued)

(58) Field of Classification Search
CPC .......... H04R 2225/43; H04R 2201/023; H04R 25/407; H04R 25/50; H04R 5/0335; H04R 1/406; H04R 1/256; G10L 15/1822; G10L 25/78; G10L 21/0272; G10L 21/028; G06F 3/011; G06K 9/00228; G06K 9/00369
See application file for complete search history.

(56) References Cited

U.S. PATENT DOCUMENTS

| | | | |
|---|---|---|---|
| 9,641,942 B2 * | 5/2017 | Strelcyk | H04R 25/50 |
| 9,746,916 B2 * | 8/2017 | Kim | G06F 3/011 |

(Continued)

*Primary Examiner* — Fan S Tsang
*Assistant Examiner* — Angelica M McKinney

(57) ABSTRACT

System and method for assessing speaker spatial orientation are provided. For example, audio data, as well as input from other sensors, may be analyzed to assess speaker spatial orientation. For example, the audio data may be analyzed to determine that two speakers are engaged in conversation. relative direction of one speaker with respect to the other may be obtained. Spatial orientation of at least one of the speakers may be obtained. The spatial orientation may be assessed according to the relative direction and the determination that the two speakers are engaged in conversation. Feedbacks and reports may be provided based on the assessed speaker spatial orientation.

20 Claims, 21 Drawing Sheets

Related U.S. Application Data filed on Jan. 10, 2017, provisional application No. 62/460,783, filed on Feb. 18, 2017.

(51) Int. Cl.

| | |
|---|---|
| *G10L 17/00* | (2013.01) |
| *G10L 17/26* | (2013.01) |
| *G10L 21/02* | (2013.01) |
| *G10L 21/028* | (2013.01) |
| *H04R 3/00* | (2006.01) |
| *H04R 25/00* | (2006.01) |
| *G10L 25/72* | (2013.01) |
| *G10L 15/18* | (2013.01) |
| *G06F 17/21* | (2006.01) |
| *G06F 17/20* | (2006.01) |
| *G10L 21/0224* | (2013.01) |
| *G10L 25/63* | (2013.01) |
| *A61B 5/16* | (2006.01) |
| *G06K 9/46* | (2006.01) |
| *H04R 5/033* | (2006.01) |
| *A61B 5/0205* | (2006.01) |
| *A61B 5/11* | (2006.01) |

(52) U.S. Cl.
CPC ...... *H04R 5/0335* (2013.01); *H04R 2201/023* (2013.01); *H04R 2225/43* (2013.01)

(56) References Cited

U.S. PATENT DOCUMENTS

| | | | |
|---|---|---|---|
| 10,241,741 B2 * | 3/2019 | Laaksonen | G06F 3/16 |
| 2002/0103649 A1 * | 8/2002 | Basson | A61F 11/04 |
| | | | 704/270 |
| 2003/0018475 A1 * | 1/2003 | Basu | G06K 9/00228 |
| | | | 704/270 |
| 2012/0020503 A1 * | 1/2012 | Endo | G10L 21/0272 |
| | | | 381/312 |
| 2012/0128186 A1 * | 5/2012 | Endo | H04R 25/407 |
| | | | 381/313 |
| 2013/0080168 A1 * | 3/2013 | Iida | G10L 25/51 |
| | | | 704/246 |
| 2015/0302867 A1 * | 10/2015 | Tomlin | G10L 25/48 |
| | | | 704/270 |
| 2017/0111303 A1 * | 4/2017 | Nesbitt | H04L 51/16 |
| 2018/0285312 A1 * | 10/2018 | Liu | G06Q 50/01 |

* cited by examiner

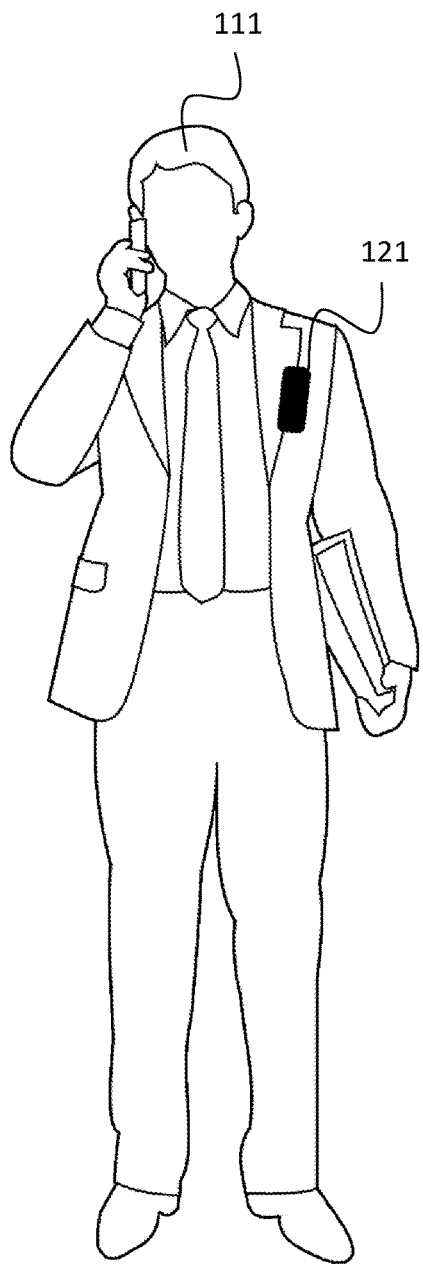
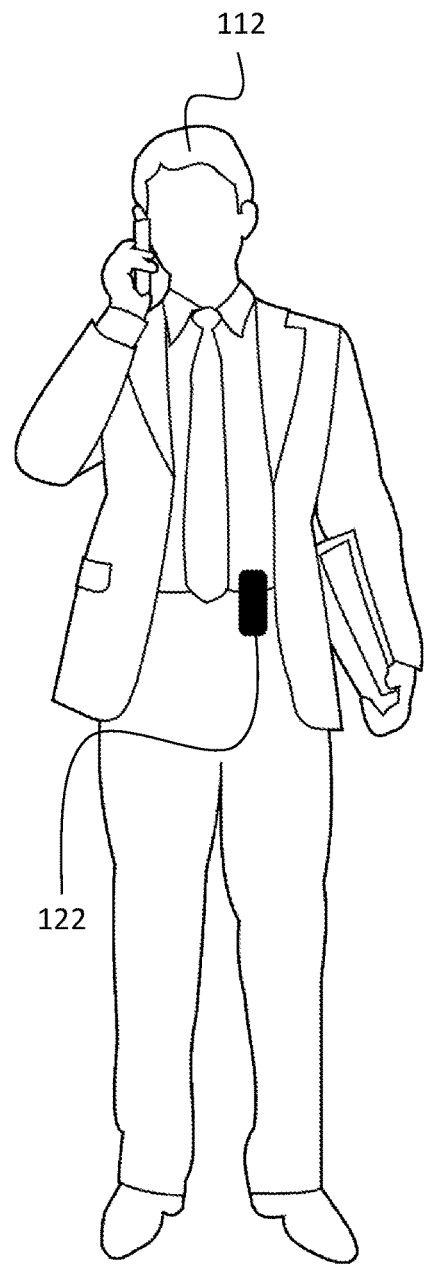
FIG. 1A  FIG. 1B

SYSTEM AND METHOD FOR ASSESSING SPEAKER SPATIAL ORIENTATION

CROSS REFERENCES TO RELATED APPLICATIONS

This application claims the benefit of priority of U.S. Provisional Patent Application No. 62/363,261, filed on Jul. 16, 2016, U.S. Provisional Patent Application No. 62/444,709, filed on Jan. 10, 2017, and U.S. Provisional Patent Application No. 62/460,783, filed on Feb. 18, 2017, the disclosures of which incorporated herein by reference in their entirety.

BACKGROUND

Technological Field

The disclosed embodiments generally relate to systems and methods for processing audio. More particularly, the disclosed embodiments relate to systems and methods for processing audio to assess speaker spatial orientation.

Background Information

Audio as well as other sensors are now part of numerous devices, from intelligent personal assistant devices to mobile phones, and the availability of audio data and other information produced by these devices is increasing.

Various conditions may cause difficulties in maintaining socially appropriate eye contact, including social phobia, autism, Asperger syndrome, and so forth. Inappropriate eye contact may include avoidance of eye contact, abnormal eye contact pattern, excessive eye contact, starring inappropriately, and so forth.

Tantrums, including temper tantrums, meltdowns and sensory meltdowns, are emotional outbursts characterized by stubbornness, crying, screaming, defiance, ranting, hitting, and tirades. In the general population, tantrums are more common in childhood, and are the result of frustration. In some conditions, including autism and Asperger's syndrome, tantrums may be the response to sensory overloads.

Echolalia is a speech disorder characterized by meaningless repetition of vocalization and speech made by another person. Palilalia is a speech disorder characterized by meaningless repetition of vocalization and speech made by the same person. The repetition may be of syllables, words, utterances, phrases, sentences, and so forth. Stuttering, also known as Dysphemia, is a speech disorder characterized by disruption of the flow of speech by involuntary repetitions and prolongations of sounds, vocalization and speech, and by silent pauses in which the speaker is unable to produce sound. Echolalia, palilalia and stuttering are possible symptoms that may occur in a variety of conditions, including: autism, Asperger syndrome, Rett syndrome, communication disorders, Tourette syndrome, Alzheimer's disease, aphasia, schizophrenia, dementia, catatonia, epilepsy, cerebral infraction, brain injury, Pick's disease, Fragile X syndrome, Prader-Willi syndrome, neurodegenerative conditions, psychological disorders, and so forth.

Cluttering, also known as tachyphemia or tachyphrasia, is a communication disorder characterized by rapid rate of speech, erratic speaking rhythm, loss of fluency, frequent pauses, and so forth. Aprosodia is a neurological condition characterized by difficult or inability to properly convey or interpret emotional prosody. Dysprosody is a neurological disorder characterized by impairment in one or more of the prosodic functions. Apraxia of speech is a communication disorder characterized by difficulty in speech production, specifically with sequencing and forming sounds, impaired speech prosody, and in particular impaired speech rhythm. Prosody may refer to variation in rhythm, pitch, stress, intonation, accent, vocal quality, intensity, tempo, flatness, melody, pauses, timing, and so forth. Impaired prosodic functions are also a possible symptom of several other neurological and psychiatric conditions, including: autism, Asperger syndrome, schizophrenia, clinical depression, aphasia, neurodegenerative conditions, and so forth.

Individuals with autism and Asperger syndrome may have difficulty or inability to adjust their language register in a socially appropriate manner.

Apraxia of speech is a communication disorder characterized by difficulty in speech production, specifically with sequencing and forming sounds, impaired speech prosody, and inconsistent articulation errors. Dysarthria is a speech disorder characterized by poor articulation of phonemes. Speech sound disorders are speech disorders characterized by articulation errors, including Developmental verbal dyspraxia and other disorders. Articulation errors are also a possible symptom of several other conditions, including: autism, Asperger syndrome, Down syndrome, aphasia, neurological disorders and neurodegenerative conditions, and so forth.

The Mean Length of Utterance (MLU) is a measurement used in the evaluation of language skills, language development, and communication disorders.

Auditory agnosia is a neurological disorder characterized by difficult or inability to recognize or differentiate between sounds, and in some cases the inability or difficulty to distinguish speech from non-speech. Linguistic agnosia is a neurological disorder characterized by the difficult or inability to comprehend spoken words and phrases. Auditory verbal agnosia, also known as pure word deafness, is a neurological disorder characterized by the difficult or inability to comprehend speech. Deaf individuals has little or no hearing, and as a result may also suffer from a difficult or inability to comprehend speech. While individuals suffering from auditory agnosia, linguistic agnosia, auditory verbal agnosia and deafness have difficulty or inability to recognize and comprehend sounds, words, phrases and speech, they can in general recognize and comprehend other sensory input, including the ability to recognize and read written text.

Vocabulary is an important tool in communication. Measuring the vocabulary size of a person may be used in the evaluation of language skills, language development, and communication disorders. Expanding vocabulary size of a person may improve the person communication abilities. This may be true both for language native speakers, and for people learning a second language.

SUMMARY

In some embodiments, a system and a method for capturing and processing audio data from the environment of a person are provided. The audio data may be analyzed. In some examples, feedbacks may be provided, for example with regard to conversations detected in the audio data. In some examples, reports may be produced, for example based on conversations detected in the audio data. In some embodiments the system may include a wearable apparatus configured to be worn by a wearer.

In some embodiments, feedbacks may be provided in real time to a user. Some examples of such feedbacks may include: suggestions on how to improve the conversation; information related to nonverbal insights on the meaning and/or state of mind of the other participants in the conversation; and so forth. In some examples, such feedbacks may assist individuals with communication difficulties, such as high functioning autistic individuals, individuals with Asperger's, individuals with Pragmatic Language Disorder, individuals with Social Communication Disorder, and so forth.

In some embodiments, reports based on the analysis of the audio data may be produced. For example, such reports may include detailed information regarding communication activities that a wearer takes part in. In some examples, such reports may assist the wearer as well as the wearer's caregivers and/or therapists to measure and analyze the wearer communication activities and abilities. In some examples, such reports may be used for diagnostic, to guide therapy, in order to keep track on the wearer progress and status, and so forth.

In some embodiments, additional input sensors may be used, for example to detect and interpret nonverbal communication. For example, the additional input sensors may include image sensors.

In some embodiments, a method and a system for assessing spatial orientation associated with speakers engaged in conversation are provided. A determination that two speakers are engaged in conversation may be made. Directional information associated with the relative direction of one speaker with respect to the second speaker may be obtained. Spatial orientation information associated with at least one speaker may be obtained. The spatial orientation information may be assessed according to the direction information.

In some embodiments, a method and a wearable apparatus for predicting tantrums are provided. Tantrum prediction rules may be obtained. Input from wearable sensors may be obtained. Tantrum prediction information may be obtained by analyzing input from wearable sensors using the tantrum prediction rules. Feedback may be provided to a user based on the tantrum prediction information.

In some embodiments, a method and a system for detecting tantrums are provided. For example, audio data, physiological data, and/or motion data captured by wearable sensors may be obtained, and the captured data may be analyzed in order to detect tantrums.

In some embodiments, a method and a system for processing audio are provided. Audio data captured by one or more wearable audio sensors may be obtained. A repetition may be detected in the audio data. Properties of the detected repetition may be identified. Feedbacks may be provided based on the detection of the repetition, and possibly based on the identified properties of the detected repetition. Information regarding the detected repetitions and their properties may be aggregated, and reports may be provided based on the aggregated information.

In some embodiments, a method and a system for identifying speech prosody are provided. Audio data captured by audio sensors may be obtained. The audio data may be analyzed to identify one or more portions of the audio data associated with a speaker. The audio data may be analyzed to obtain prosodic information associated with the one or more portions.

In some embodiments, a method and a system for identifying language register are provided. Audio data captured by audio sensors may be obtained. The audio data may be analyzed to obtain language register information.

In some embodiments, a method and a system for detecting articulation errors are provided. Audio data captured by audio sensors may be obtained. The audio data may be analyzed to detect articulation errors.

In some embodiments, a method and a system for analyzing audio data to obtain one or more measurements are provided. Audio data captured by audio sensors may be obtained. The audio data may be analyzed to identify one or more portions of the audio data associated with a speaker. The audio data may be analyzed to identify one or more utterances in the one or more portions of audio data. The audio data may be further analyzed to obtain one or more measurements associated with the length of the one or more utterances.

In some embodiments, a method and a wearable apparatus for processing audio are provided. Audio data may be obtained, for example by capturing audio from the environment of the user using wearable audio sensors. The audio data may be analyzed to obtain textual information. Speaker information may be obtained. The textual information may be visually presented to the user, possibly based on the speaker information.

In some embodiments, a method and a system for analyzing audio data to identify speaker vocabulary are provided. Audio data captured by audio sensors may be obtained. The audio data may be analyzed to identify one or more words associated with a speaker. One or more vocabulary records may be updated based on the one or more words. Feedbacks and reports may be provided based on the one or more vocabulary records.

BRIEF DESCRIPTION OF THE DRAWINGS

FIGS. 1A, 1B, 1C, 1D, 1E and 1F are schematic illustrations of some examples of a user wearing a wearable apparatus.

DESCRIPTION

Figure 1C:
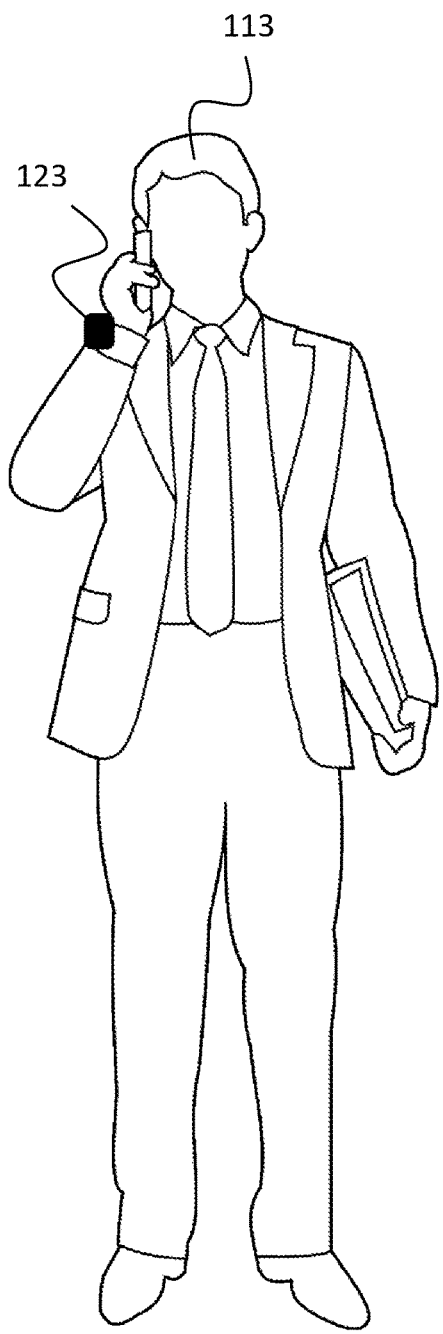

Unless specifically stated otherwise, as apparent from the following discussions, it is appreciated that throughout the specification discussions utilizing terms such as "processing", "calculating", "computing", "determining", "generating", "setting", "configuring", "selecting", "defining", "applying", "obtaining", "monitoring", "providing", "identifying", "segmenting", "classifying", "analyzing", "associating", "extracting", "storing", "receiving", "transmitting", or the like, include action and/or processes of a computer that manipulate and/or transform data into other data, said data represented as physical quantities, for example such as electronic quantities, and/or said data representing the physical objects.

The terms "computer", "processor", "controller", "processing unit", "computing unit", "processing device", and "processing module" should be expansively construed to cover any kind of electronic device, component or unit with data processing capabilities, including, by way of non-limiting example, a personal computer, a wearable computer, a tablet, a smartphone, a server, a computing system, a cloud computing platform, a communication device, a processor (for example, digital signal processor (DSP), an image signal processor (ISR), a microcontroller, a field programmable gate array (FPGA), an application specific integrated circuit (ASIC), a central processing unit (CPA), a graphics processing unit (GPU), a visual processing unit (VPU), and so on), possibly with embedded memory, a single core processor, a multi core processor, a core within a processor, any other electronic computing device, or any combination of the above.

The operations in accordance with the teachings herein may be performed by a computer specially constructed or programmed to perform the described functions.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) may be included in at least one embodiment of the presently disclosed subject matter. Thus the appearance of the phrase "one case", "some cases", "other cases" or variants thereof does not necessarily refer to the same embodiment(s). As used herein, the term "and/or" includes any and all combinations of one or more of the associated listed items.

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable subcombination.

As used herein, the term "tantrum" is to be broadly interpreted to include tantrum, temper tantrum, and sensory meltdown.

One or more stages illustrated in the drawings may be executed in a different order and/or one or more groups of stages may be executed simultaneously and vice versa. The drawings illustrate a general schematic of the system architecture in accordance embodiments of the presently disclosed subject matter. Each module in the drawings can be made up of any combination of software, hardware and/or firmware that performs the functions as defined and explained herein. The modules in the drawings may be centralized in one location or dispersed over more than one location.

It should be noted that some examples of the presently disclosed subject matter are not limited in application to the details of construction and the arrangement of the components set forth in the following description or illustrated in the drawings. The invention can be capable of other embodiments or of being practiced or carried out in various ways. Also, it is to be understood that the phraseology and terminology employed herein is for the purpose of description and should not be regarded as limiting. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Wherever possible, the same reference numbers are used in the drawings and the following description to refer to the same or similar parts.

The drawings in this document may not be to any scale. Different drawings may use different scales and different scales can be used even within the same drawing, for example different scales for different views of the same object or different scales for the two adjacent objects.

FIG. 1A is a schematic illustration of an example of user 111 wearing wearable apparatus or a part of a wearable apparatus 121. In this example, wearable apparatus or a part of a wearable apparatus 121 may be physically connected or integral to a garment, and user 111 may wear the garment.

FIG. 1B is a schematic illustration of an example of user 112 wearing wearable apparatus or a part of a wearable apparatus 122. In this example, wearable apparatus or a part of a wearable apparatus 122 may be physically connected or integral to a belt, and user 112 may wear the belt.

FIG. 1C is a schematic illustration of an example of user 113 wearing wearable apparatus or a part of a wearable apparatus 123. In this example, wearable apparatus or a part of a wearable apparatus 123 may be physically connected or integral to a wrist strap, and user 113 may wear the wrist strap.

Figure 1D:

FIG. 1D is a schematic illustration of an example of user 114 wearing wearable apparatus or a part of a wearable apparatus 124. In this example, wearable apparatus or a part of a wearable apparatus 124 may be physically connected or integral to a necklace 134, and user 114 may wear necklace 134.

Figure 1E:
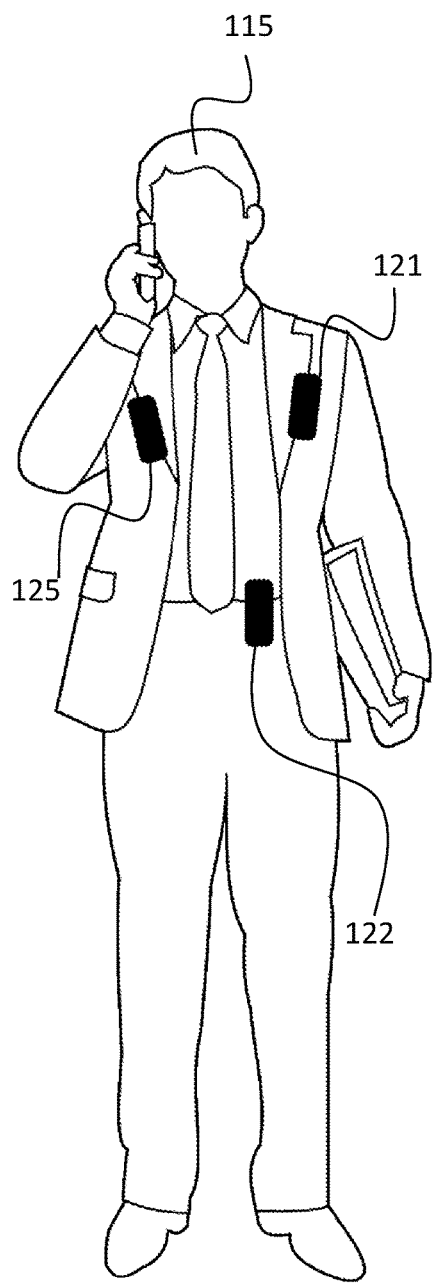

FIG. 1E is a schematic illustration of an example of user 115 wearing wearable apparatus or a part of a wearable apparatus 121, wearable apparatus or a part of a wearable apparatus 122, and wearable apparatus or a part of a wearable apparatus 125. In this example, wearable apparatus or a part of a wearable apparatus 122 may be physically connected or integral to a belt, and user 115 may wear the belt. In this example, wearable apparatus or a part of a wearable apparatus 121 and wearable apparatus or a part of a wearable apparatus 125 may be physically connected or integral to a garment, and user 115 may wear the garment.

Figure 1F:
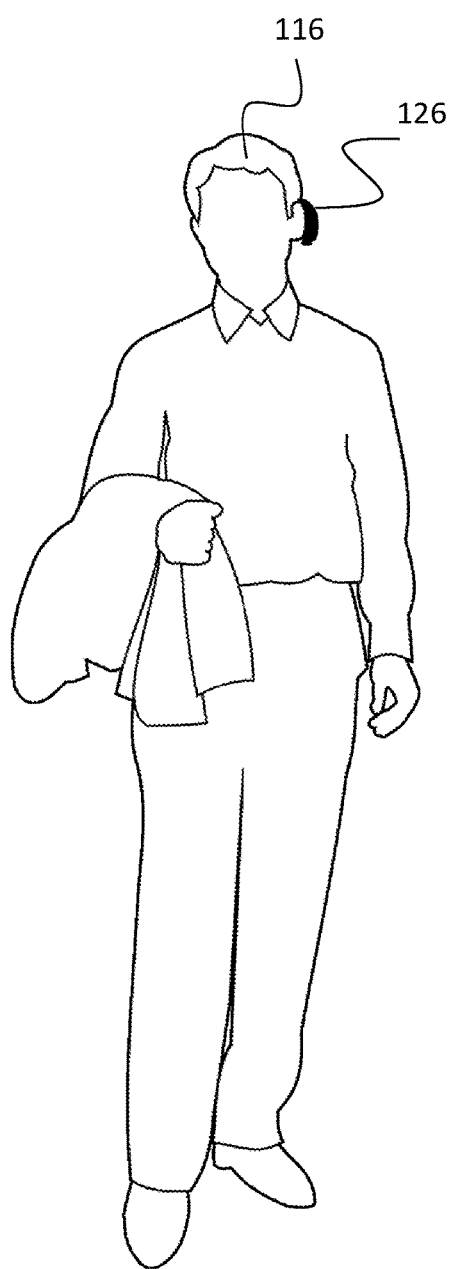

FIG. 1F is a schematic illustration of an example of user 116 wearing wearable apparatus or a part of a wearable apparatus 126. In this example, wearable apparatus or a part of a wearable apparatus 126 may be physically connected to an ear of user 116. In some examples, wearable apparatus or a part of a wearable apparatus 126 may be physically connected to the left ear and/or right ear of user 116. In some examples, user 116 may wear two wearable apparatuses 126, where one wearable apparatus 126 may be connected to the left ear of user 116, and the second wearable apparatus 126 may be connected to the right ear of user 116. In some examples, user 116 may wear a wearable apparatus 126 that has at least two separate parts, where one part of wearable apparatus 126 may be connected to the left ear of user 116, and the second part of wearable apparatus 126 may be connected to the right ear of user 116.

In some embodiments, a user may wear one or more wearable apparatuses, such as one or more instances of wearable apparatuses 121, 122, 123, 124, 125, and/or 126. For example, a user may wear one or more wearable apparatuses that are physically connected or integral to a garment of the user, such as wearable apparatus 121 and/or wearable apparatus 125. For example, a user may wear one or more wearable apparatuses that are physically connected or integral to a belt of the user, such as wearable apparatus 122. For example, a user may wear one or more wearable apparatuses that are physically connected or integral to a wrist strap of the user, such as wearable apparatus 123. For example, a user may wear one or more wearable apparatuses that are physically connected or integral to a necklace that the user is wearing, such as wearable apparatus 124. For example, a user may wear one or more wearable apparatuses that are physically connected or integral to the left ear and/or right ear of the user, such as wearable apparatus 126. In some examples, the one or more wearable apparatuses may communicate and/or collaborate with one another. For example, the one or more wearable apparatuses may communicate by wires and/or wirelessly.

In some embodiments, a user may wear a wearable apparatus, and the wearable apparatus may comprise two or more separate parts. For example, the wearable apparatus may comprise parts 121, 122, 123, 124, 125, and/or 126. For example, the wearable apparatus may comprise one or more parts that are physically connected or integral to a garment of the user, such as 121 and/or part 125. For example, the wearable apparatus may comprise one or more parts that are physically connected or integral to a belt of the user, such as part 122. For example, the wearable apparatus may comprise one or more parts that are physically connected or integral to a wrist strap that the user is wearing, such as part 123. For example, the wearable apparatus may comprise one or more parts that are physically connected or integral to a necklace that the user is wearing, such as part 124. For example, the wearable apparatus may comprise one or more parts that are physically connected to the left ear and/or the right ear of the user, such as part 126. In some examples, the separate parts of the wearable apparatus may communicate by wires and/or wirelessly.

Figure 3A:
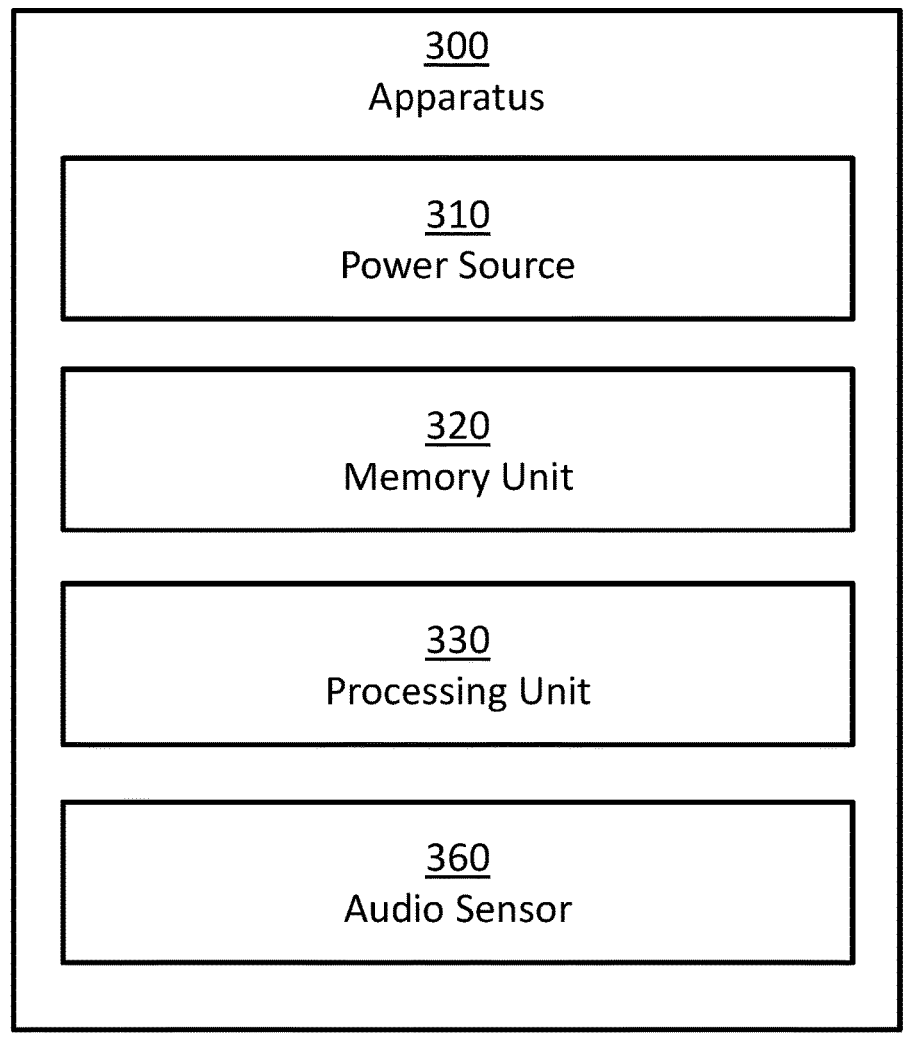
FIGS. 3A and 3B are block diagrams illustrating some possible implementation of an apparatus.
Figure 3B:
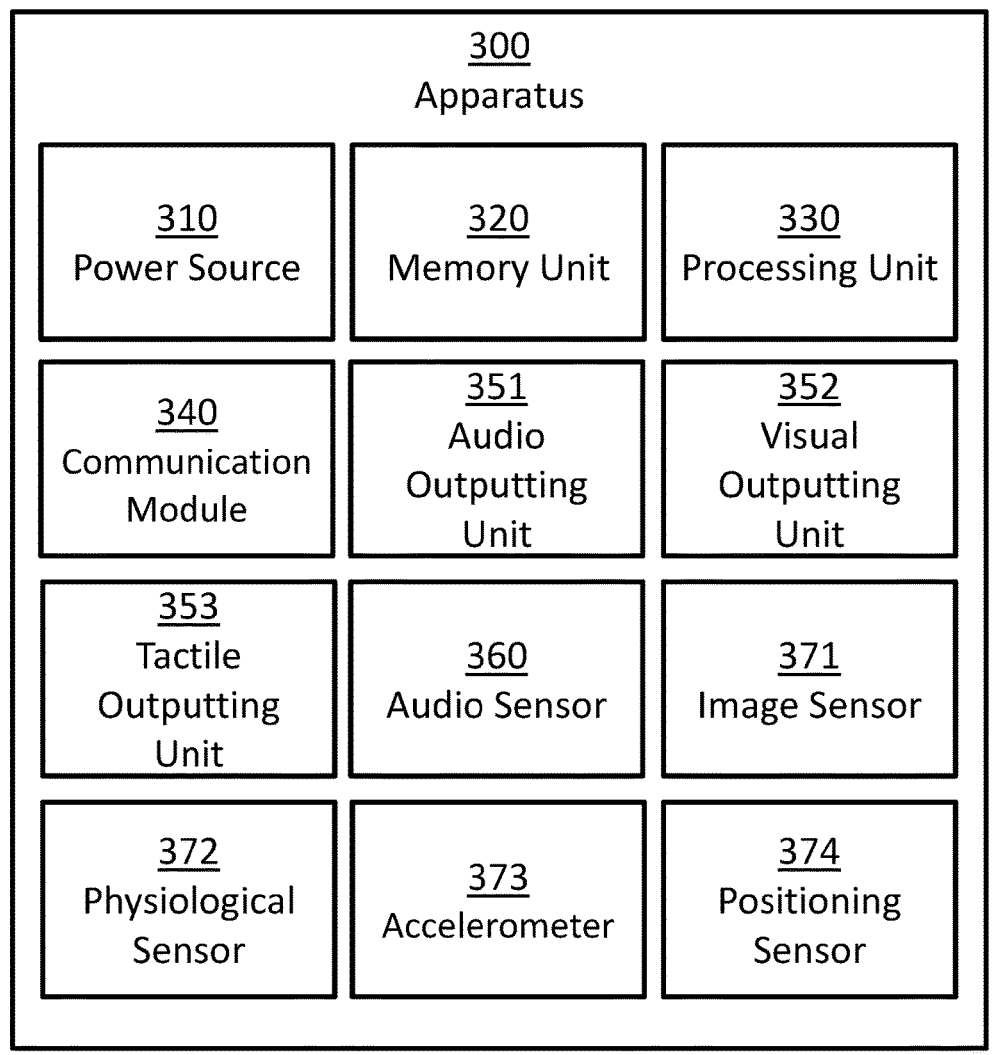

In some embodiments, possible implementations of wearable apparatuses 121, 122, 123, 124, 125, and/or 126 may include apparatus 300, for example as described in FIGS. 3A and 3B. In some embodiments, apparatus 300 may comprise two or more separate parts. For example, apparatus 300 may comprise parts 121, 122, 123, 124, 125, and/or 126. In some examples, the separate parts may communicate by wires and/or wirelessly.

Figure 2A:
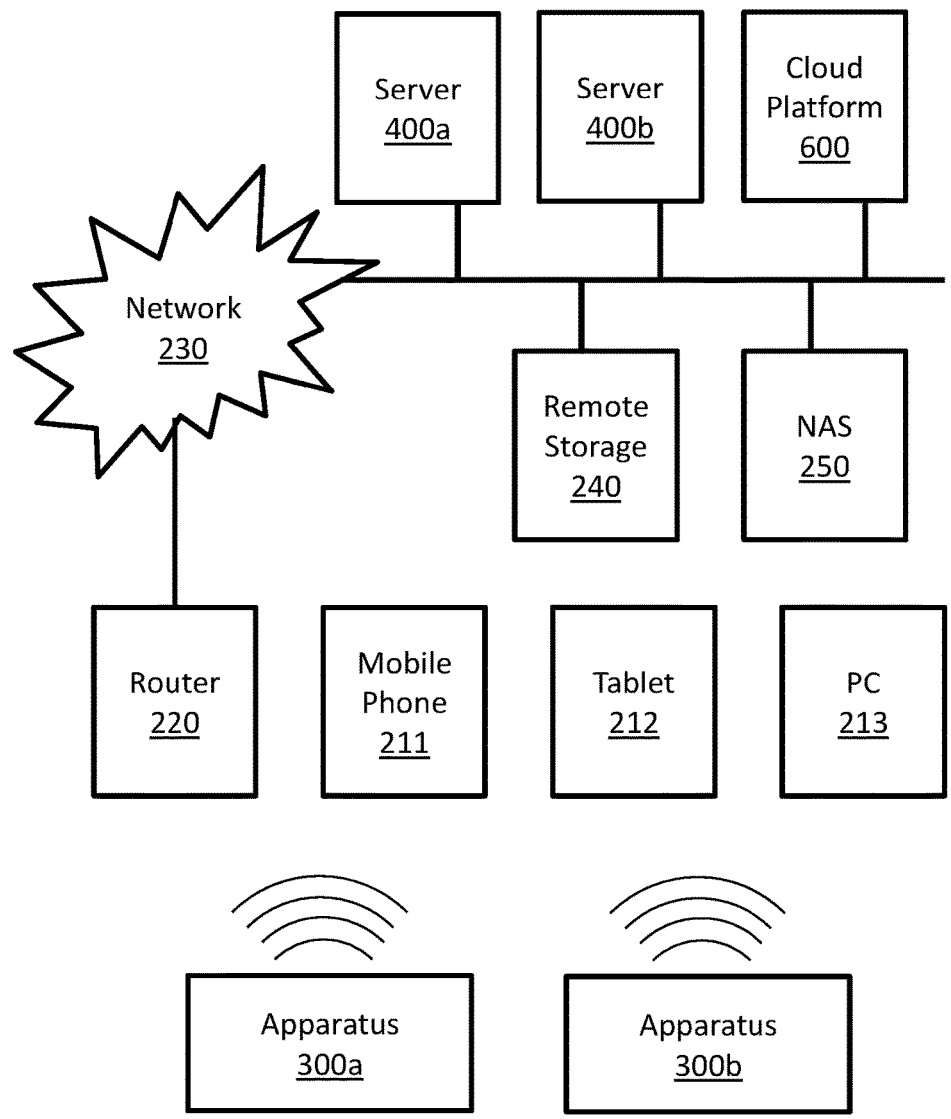
FIGS. 2A and 2B are block diagrams illustrating some possible implementation of a communication system.

FIG. 2A is a block diagram illustrating a possible implementation of a communicating system. In this example, apparatuses 300a and 300b may communicate with server 400a, with server 400b, with cloud platform 500, with each other, and so forth. Some possible implementations of apparatuses 300a and 300b may include apparatus 300, for example as described in FIGS. 3A and 3B. Some possible implementations of servers 400a and/or 400b may include server 400, for example as described in FIG. 4. Some possible implementations of cloud platform 500 are described in FIGS. 5A, 5B and 5C. In this example, apparatus 300a and/or apparatus 300b may communicate directly with mobile phone 211, tablet 212, and/or personal computer (PC) 213. Apparatus 300a and/or apparatus 300b may communicate with local router 220 directly, and/or through at least one of mobile phone 211, tablet 212, and/or personal computer (PC) 213. In this example, local router 220 may be connected to communication network 230. Some examples of communication network 230 may include the Internet, phone networks, cellular networks, satellite communication networks, private communication networks, virtual private networks (VPN), and so forth. Apparatus 300a and/or apparatus 300b may connect to communication network 230 through local router 220 and/or directly. Apparatus 300a and/or apparatus 300b may communicate with other devices, such as servers 400a, server 400b, cloud platform 500, remote storage 240 and network attached storage (NAS) 250, and so forth, through communication network 230 and/or directly.

Figure 2B:
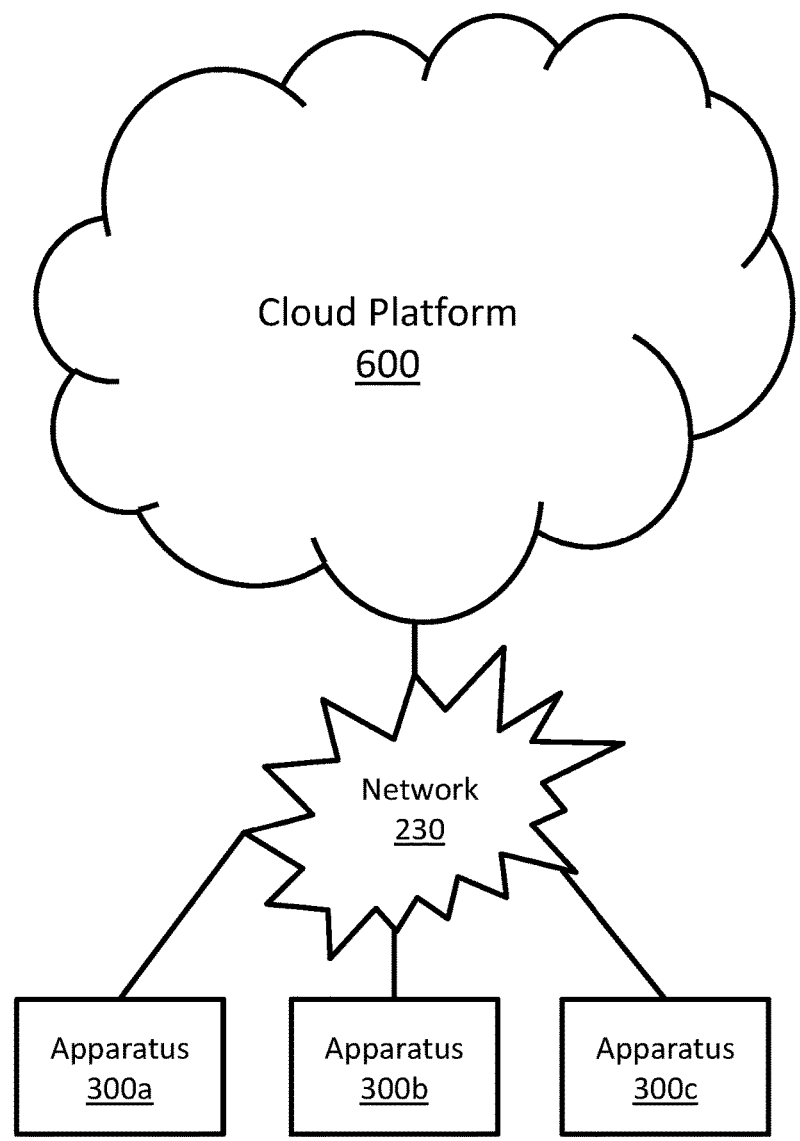

FIG. 2B is a block diagram illustrating a possible implementation of a communicating system. In this example, apparatus 300a, apparatus 300b and/or apparatus 300c may communicate with cloud platform 500 and/or with each other through communication network 230. Possible implementations of apparatuses 300a, 300b and 300c may include apparatus 300, for example as described in FIGS. 3A and 3B. Some possible implementations of cloud platform 500 are described in FIGS. 5A, 5B and 5C. Some examples of communication network 230 may include the Internet, phone networks, cellular networks, satellite communication networks, private communication networks, virtual private networks (VPN), and so forth.

FIGS. 2A and 2B illustrate some possible implementations of a communication system. In some embodiments, other communication systems that enable communication between apparatus 300 and server 400 may be used. In some embodiments, other communication systems that enable communication between apparatus 300 and cloud platform 500 may be used. In some embodiments, other communication systems that enable communication among a plurality of apparatuses 300 may be used.

FIG. 3A is a block diagram illustrating a possible implementation of apparatus 300. In this example, apparatus 300 comprises: one or more power sources 310; one or more memory units 320; one or more processing units 330; and one or more audio sensors 360. In some implementations additional components may be included in apparatus 300, while some components listed above may be excluded. In some embodiments, power sources 310 and/or audio sensors 360 may be excluded from the implementation of apparatus 300. In some embodiments, apparatus 300 may further comprise one or more of the followings: one or more communication modules 340; one or more audio output units 351; one or more visual outputting units 352; one or more tactile outputting units 353; one or more image sensors 371; one or more physiological sensors 372; one or more accelerometers 373; one or more positioning sensors 374; one or more chemical sensors; one or more temperature sensors; one or more barometers; one or more environmental sensors; one or more pressure sensors; one or more proximity sensors; one or more electrical impedance sensors; one or more electrical voltage sensors; one or more electrical current sensors; one or more clocks; one or more user input devices; one or more keyboards; one or more mouses; one or more touch pads; one or more touch screens; one or more antennas; one or more output devices; one or more audio speakers; one or more display screens; one or more augmented reality display systems; one or more LED indicators; and so forth.

FIG. 3B is a block diagram illustrating a possible implementation of apparatus 300. In this example, apparatus 300 comprises: one or more power sources 310; one or more memory units 320; one or more processing units 330; one or more communication modules 340; one or more audio output units 351; one or more visual outputting units 352; one or more tactile outputting units 353; one or more audio sensors 360; one or more image sensors 371; one or more physiological sensors 372; one or more accelerometers 373; and one or more positioning sensors 374. In some implementations additional components may be included in apparatus 300, while some components listed above may be excluded. In some embodiments, one or more of the followings may be excluded from the implementation of apparatus 300: power sources 310; communication modules 340; audio output units 351; visual outputting units 352; tactile outputting units 353; audio sensors 360; image sensors 371; physiological sensors 372; accelerometers 373; and positioning sensors 374. In some embodiments, apparatus 300 may further comprise one or more of the followings: one or more chemical sensors; one or more temperature sensors; one or more barometers; one or more environmental sensors; one or more pressure sensors; one or more proximity sensors; one or more electrical impedance sensors; one or more electrical voltage sensors; one or more electrical current sensors; one or more clocks; one or more user input devices; one or more keyboards; one or more mouses; one or more touch pads; one or more touch screens; one or more antennas; one or more output devices; one or more audio speakers; one or more display screens; one or more augmented reality display systems; one or more LED indicators; and so forth.

In some embodiments, the one or more power sources 310 may be configured to: power apparatus 300; power server 400; power cloud platform 500; power computational node 510; and so forth. Some possible implementation examples the one or more power sources 310 may comprise: one or more electric batteries; one or more capacitors; one or more connections to external power sources; one or more power convertors; one or more electric power generators; any combination of the above; and so forth.

In some embodiments, the one or more processing units 330 may be configured to execute software programs, for example software programs stored in the one or more memory units 320, software programs received through the one or more communication modules 340, and so forth. Some possible implementation examples of processing units 330 may comprise: one or more single core processors; one or more multicore processors; one or more controllers; one or more application processors; one or more system on a chip processors; one or more central processing units; one or more graphical processing units; one or more neural processing units; any combination of the above; and so forth. In some examples, the executed software programs may store information in memory units 320. In some cases, the executed software programs may retrieve information from memory units 320.

In some embodiments, the one or more communication modules 340 may be configured to receive and/or transmit information. Some possible implementation examples of communication modules 340 may comprise: wired communication devices; wireless communication devices; optical communication devices; electrical communication devices; radio communication devices; sonic and/or ultrasonic communication devices; electromagnetic induction communication devices; infrared communication devices; transmitters; receivers; transmitting and receiving devices; modems; network interfaces; wireless USB communication devices, wireless LAN communication devices; Wi-Fi communication devices; LAN communication devices; USB communication devices; firewire communication devices; bluetooth communication devices; cellular communication devices, such as GSM, CDMA, GPRS, W-CDMA, EDGE, CDMA2000, etc.; satellite communication devices; and so forth.

In some implementations, control signals and/or synchronization signals may be transmitted and/or received through communication modules 340. In some implementations, information received though communication modules 340 may be stored in memory units 320. In some implementations, information retrieved from memory units 320 may be transmitted using communication modules 340. In some implementations, input and/or user input may be transmitted and/or received through communication modules 340. In some implementations, audio data may be transmitted and/or received through communication modules 340, such as audio data captured using audio sensors 360. In some implementations, visual data, such as images and/or videos, may be transmitted and/or received through communication modules 340, such as images and/or videos captured using image sensors 371. In some implementations, physiological data may be transmitted and/or received through communication modules 340, such as physiological data captured using physiological sensors 372. In some implementations, proper acceleration information may be transmitted and/or received through communication modules 340, such as proper acceleration information captured using accelerometers 373. In some implementations, positioning information may be transmitted and/or received through communication modules 340, such as positioning information captured using positioning sensors 374.

In some implementations, output information may be transmitted and/or received through communication modules 340. In some implementations, audio output information may be transmitted and/or received through communication modules 340. For example, audio output information to be outputted using audio outputting units 351 may be received through communication modules 340. In some implementations, visual output information may be transmitted and/or received through communication modules 340. For example, visual output information to be outputted using visual outputting units 352 may be received through communication modules 340. In some implementations, tactile output information may be transmitted and/or received through communication modules 340. For example, tactile output information to be outputted using tactile outputting units 353 may be received through communication modules 340.

In some embodiments, the one or more audio outputting units 351 may be configured to output audio to a user, for example through a headset, through one or more audio speakers, and so forth. In some embodiments, the one or more visual outputting units 352 may be configured to output visual information to a user, for example through a display screen, through an augmented reality display system, through a printer, through LED indicators, and so forth. In some embodiments, the one or more tactile outputting units 353 may be configured to output tactile feedbacks to a user, for example through vibrations, through motions, by applying forces, and so forth. In some examples, output may be provided: in real time; offline; automatically; periodically; upon request; and so forth. In some examples, apparatus 300 may be a wearable apparatus and the output may be provided to: a wearer of the wearable apparatus; a caregiver of the wearer of the wearable apparatus; and so forth. In some examples, the output may be provided to: a caregiver; clinicians; insurers; and so forth.

In some embodiments, the one or more audio sensors 360 may be configured to capture audio data. Some possible examples of audio sensors 360 may include: connectors to microphones; microphones; unidirectional microphones; bidirectional microphones; cardioid microphones; omnidirectional microphones; onboard microphones; wired microphones; wireless microphones; any combination of the above; and so forth. In some cases, audio data captured using audio sensors 360 may be stored in memory, for example in memory units 320. In some cases, audio data captured using audio sensors 360 may be transmitted, for example using communication device 340 to an external system, such as server 400, cloud platform 500, computational node 510, apparatus 300, and so forth. In some cases, audio data captured using audio sensors 360 may be processed, for example using processing units 330. For example, the audio data captured using audio sensors 360 may be: compressed; preprocessed using filters, such as low pass filters, high pass filters, etc.; downsampled; and so forth. In some cases, audio data captured using audio sensors 360 may be analyzed, for example using processing units 330. For example, audio data captured using audio sensors 360 may be analyzed to identify low level features, speakers, speech, audio triggers, and so forth. In another example, audio data captured using audio sensors 360 may be applied to an inference model.

In some embodiments, the one or more image sensors 371 may be configured to capture visual data. Some possible examples of image sensors 371 may include: CCD sensors; CMOS sensors; stills image sensors; video image sensors; 2D image sensors; 3D image sensors; and so forth. Some possible examples of visual data may include: still images; video clips; continuous video; 2D images; 2D videos; 3D images; 3D videos; microwave images; terahertz images; ultraviolet images; infrared images; x-ray images; gamma ray images; visible light images; microwave videos; terahertz videos; ultraviolet videos; infrared videos; visible light videos; x-ray videos; gamma ray videos; and so forth. In some cases, visual data captured using image sensors 371 may be stored in memory, for example in memory units 320. In some cases, visual data captured using image sensors 371 may be transmitted, for example using communication device 340 to an external system, such as server 400, cloud platform 500, computational node 510, apparatus 300, and so forth. In some cases, visual data captured using image sensors 371 may be processed, for example using processing units 330. For example, the visual data captured using image sensors 371 may be: compressed; preprocessed using filters, such as low pass filter, high pass filter, etc.; downsampled; and so forth. In some cases, visual data captured using image sensors 371 may be analyzed, for example using processing units 330. For example, visual data captured using image sensors 371 may be analyzed to identify one or more of: low level visual features; objects; faces; persons; events; visual triggers; and so forth. In another example, visual data captured using image sensors 371 may be applied to an inference model.

In some embodiments, the one or more physiological sensors 372 may be configured to capture physiological data. Some possible examples of physiological sensors 372 may include: glucose sensors; electrocardiogram sensors; electroencephalogram sensors; electromyography sensors; odor sensors; respiration sensors; blood pressure sensors; pulse oximeter sensors; heart rate sensors; perspiration sensors; and so forth. In some cases, physiological data captured using physiological sensors 372 may be stored in memory, for example in memory units 320. In some cases, physiological data captured using physiological sensors 372 may be transmitted, for example using communication device 340 to an external system, such as server 400, cloud platform 500, computational node 510, apparatus 300, and so forth. In some cases, physiological data captured using physiological sensors 372 may be processed, for example using processing units 330. For example, the physiological data captured using physiological sensors 372 may be compressed, downsampled, and so forth. In some cases, physiological data captured using physiological sensors 372 may be analyzed, for example using processing units 330. For example, physiological data captured using physiological sensors 372 may be analyzed to identify events, triggers, and so forth. In another example, physiological data captured using physiological sensors 372 may be applied to an inference model.

In some embodiments, the one or more accelerometers 373 may be configured to capture proper acceleration information, for example by: measuring proper acceleration of apparatus 300; detecting changes in proper acceleration of apparatus 300; and so forth. In some embodiments, the one or more accelerometers 373 may comprise one or more gyroscopes. In some cases, information captured using accelerometers 373 may be stored in memory, for example in memory units 320. In some cases, information captured using accelerometers 373 may be transmitted, for example using communication device 340 to an external system, such as server 400, cloud platform 500, computational node 510, apparatus 300, and so forth. In some cases, information captured using accelerometers 373 may be processed, for example using processing units 330. For example, the information captured using accelerometers 373 may be compressed, downsampled, and so forth. In some cases, information captured using accelerometers 373 may be analyzed, for example using processing units 330. For example, the information captured using accelerometers 373 may be analyzed to identify events, triggers, and so forth. In another example, the information captured using accelerometers 373 may be applied to an inference model.

In some embodiments, the one or more positioning sensors 374 may be configured to: obtain positioning information associated with apparatus 300; detect changes in the position of apparatus 300; and so forth. In some embodiments, the positioning sensors 374 may be implemented using different technologies, such as: Global Positioning System (GPS); GLObal NAvigation Satellite System (GLONASS); Galileo global navigation system, BeiDou navigation system; other Global Navigation Satellite Systems (GNSS); Indian Regional Navigation Satellite System (IRNSS); Local Positioning Systems (LPS), Real-Time Location Systems (RTLS); Indoor Positioning System (IPS); Wi-Fi based positioning systems; cellular triangulation; and so forth. In some embodiments, the one or more positioning sensors 374 may comprise one or more altimeters, and be configured to measure altitude and/or to detect changes in altitude. In some embodiments, information captured using positioning sensors 374 may be stored in memory, for example in memory units 320. In some cases, information captured using positioning sensors 374 may be transmitted, for example using communication device 340 to an external system, such as server 400, cloud platform 500, computational node 510, apparatus 300, and so forth. In some cases, information captured using positioning sensors 374 may be processed, for example using processing units 330. For example, the information captured using positioning sensors 374 may be compressed, downsampled, and so forth. In some cases, information captured using positioning sensors 374 may be analyzed, for example using processing units 330. For example, the information captured using positioning sensors 374 may be analyzed to identify events, triggers, and so forth. In another example, the information captured using positioning sensors 374 may be applied to an inference model.

Figure 4:
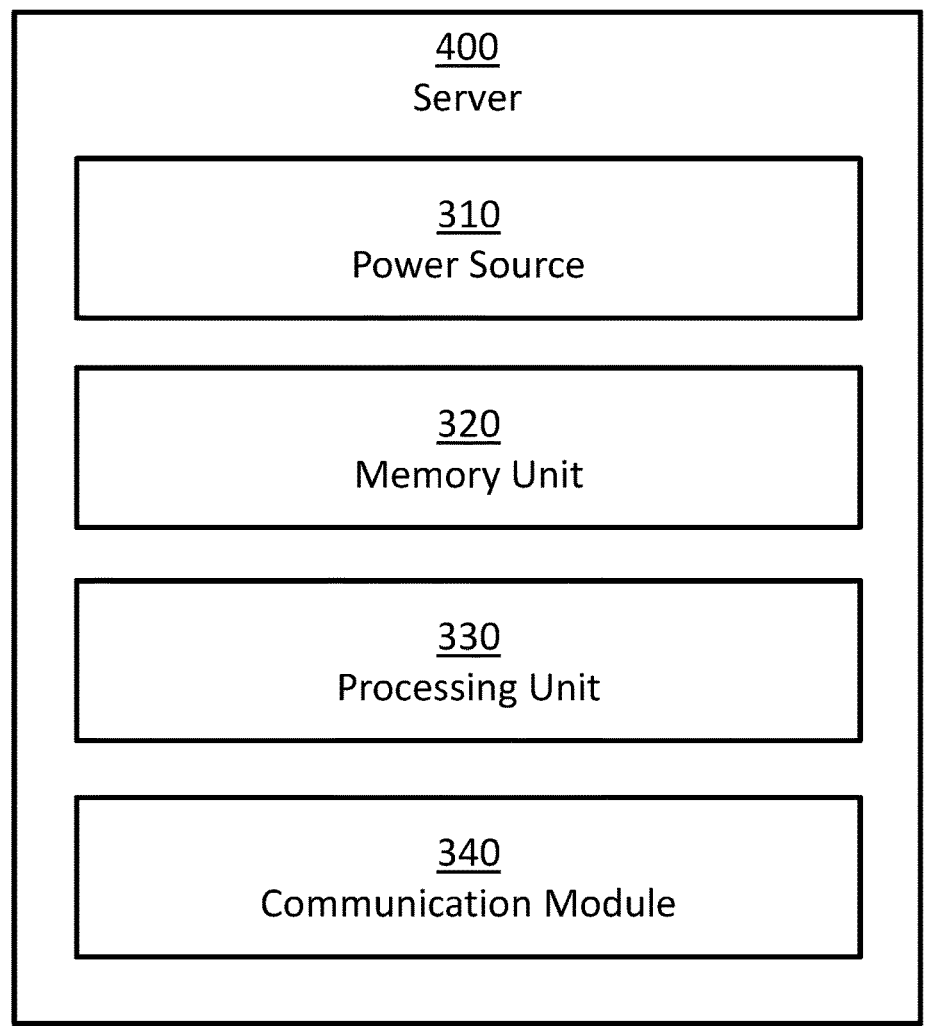
FIG. 4 is a block diagram illustrating a possible implementation of a server.

FIG. 4 is a block diagram illustrating a possible implementation of a server 400. In this example, server 400 comprises: one or more power sources 310; one or more memory units 320; one or more processing units 330; and one or more communication modules 340. In some implementations additional components may be included in server 400, while some components listed above may be excluded. In some embodiments, power sources 310 and/or communication modules 340 may be excluded from the implementation of server 400. In some embodiments, server 400 may further comprise one or more of the followings: one or more audio output units 351; one or more visual outputting units 352; one or more tactile outputting units 353; one or more audio sensors 360; one or more image sensors 371; one or more accelerometers 373; one or more positioning sensors 374; one or more chemical sensors; one or more temperature sensors; one or more barometers; one or more environmental sensors; one or more pressure sensors; one or more proximity sensors; one or more electrical impedance sensors; one or more electrical voltage sensors; one or more electrical current sensors; one or more clocks; one or more user input devices; one or more keyboards; one or more mouses; one or more touch pads; one or more touch screens; one or more antennas; one or more output devices; one or more audio speakers; one or more display screens; one or more augmented reality display systems; one or more LED indicators; and so forth.

Figure 5A:
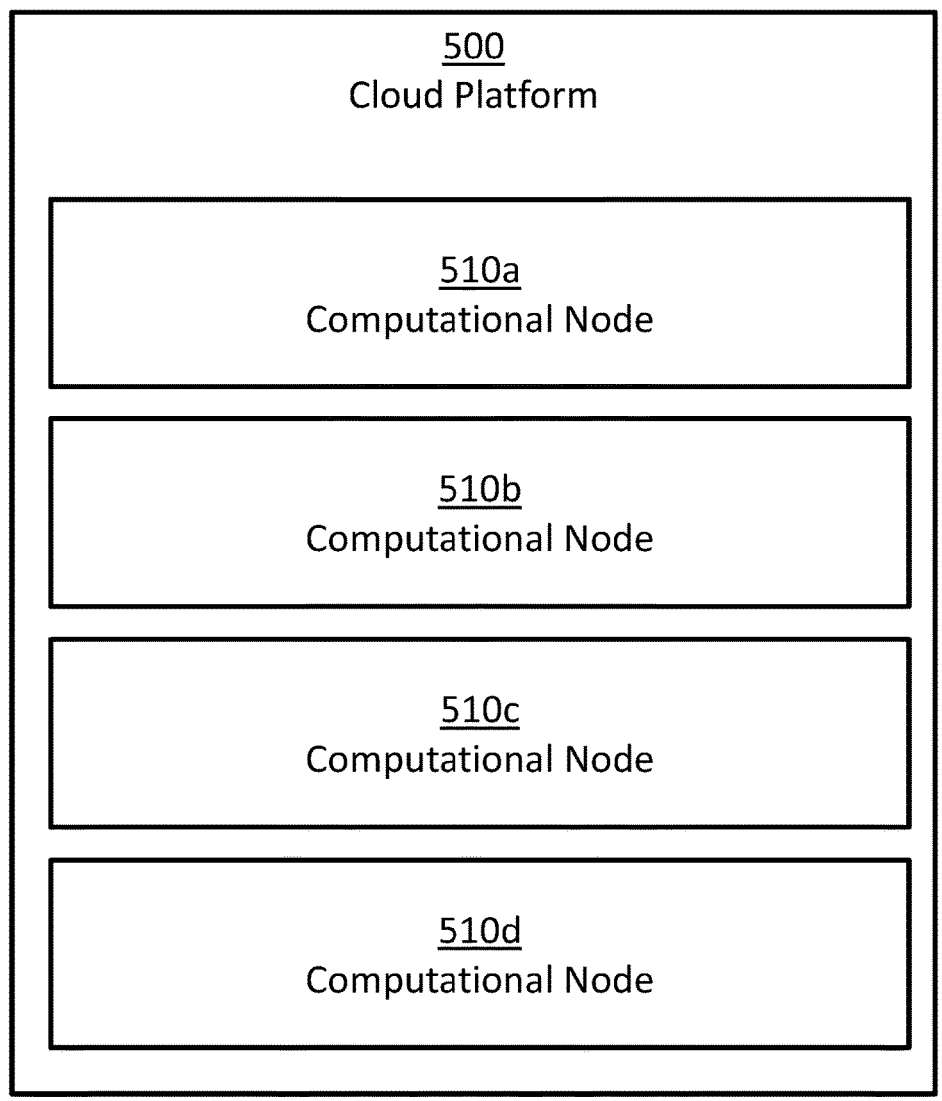
FIGS. 5A and 5B are block diagrams illustrating some possible implementation of a cloud platform.

FIG. 5A is a block diagram illustrating a possible implementation of cloud platform 500. In some examples, cloud platform 500 may comprise a number of computational nodes, in this example four computational nodes: computational node 510a, computational node 510b, computational node 510c and computational node 510d. In some examples, a possible implementation of computational nodes 510a, 510b, 510c and/or 510d may comprise server 400 as described in FIG. 4. In some examples, a possible implementation of computational nodes 510a, 510b, 510c and/or 510d may comprise computational node 510 as described in FIG. 5C.

Figure 5B:
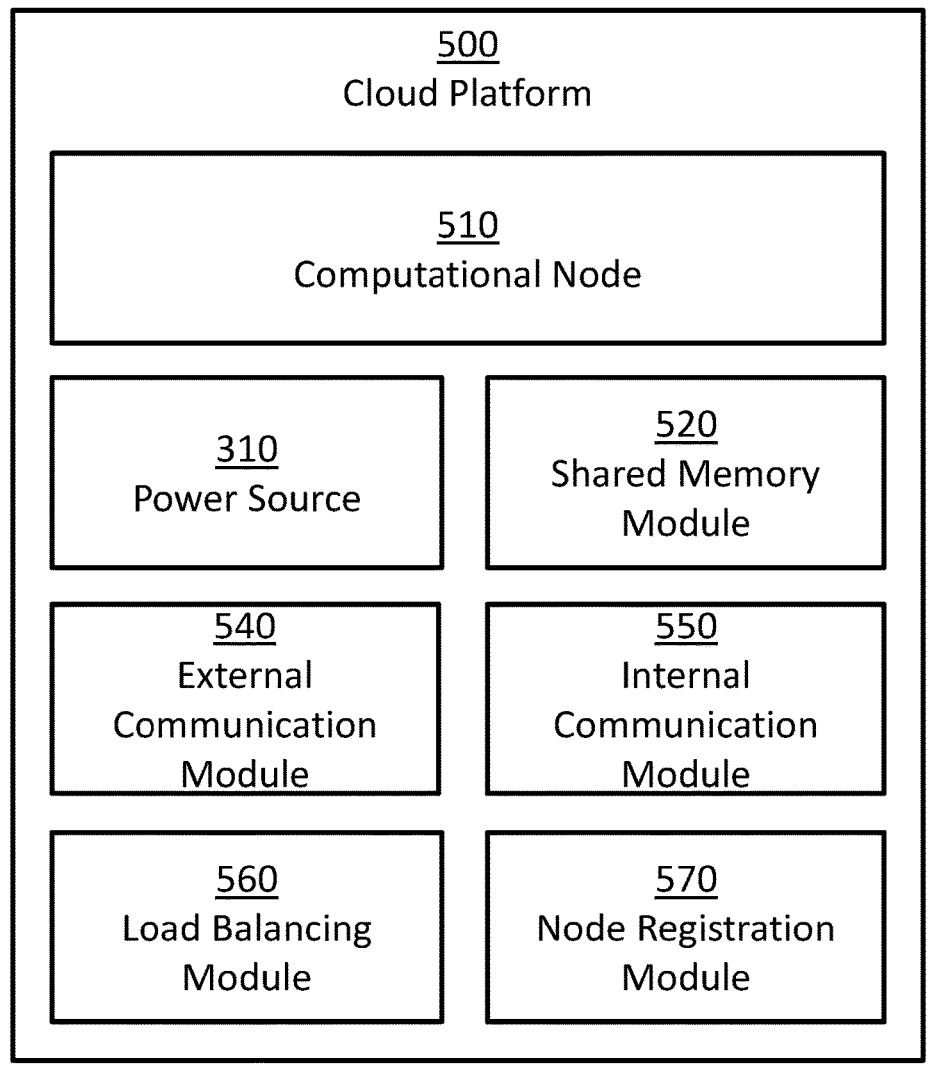

FIG. 5B is a block diagram illustrating a possible implementation of cloud platform 500. In this example, cloud platform 500 comprises: one or more computational nodes 510; one or more power sources 310; one or more shared memory modules 520; one or more external communication modules 540; one or more internal communication modules 550; one or more load balancing modules 560; and one or more node registration modules 570. In some implementations additional components may be included in cloud platform 500, while some components listed above may be excluded. In some embodiments, one or more of the followings may be excluded from the implementation of cloud platform 500: power sources 310; shared memory modules 520; external communication modules 540; internal communication modules 550; load balancing modules 560; and node registration modules 570. In some embodiments, cloud platform 500 may further comprise one or more of the followings: one or more audio output units 351; one or more visual outputting units 352; one or more tactile outputting units 353; one or more audio sensors 360; one or more image sensors 371; one or more accelerometers 373; one or more positioning sensors 374; one or more chemical sensors; one or more temperature sensors; one or more barometers; one or more environmental sensors; one or more pressure sensors; one or more proximity sensors; one or more electrical impedance sensors; one or more electrical voltage sensors; one or more electrical current sensors; one or more clocks; one or more user input devices; one or more keyboards; one or more mouses; one or more touch pads; one or more touch screens; one or more antennas; one or more output devices; one or more audio speakers; one or more display screens; one or more augmented reality display systems; one or more LED indicators; and so forth.

Figure 5C:
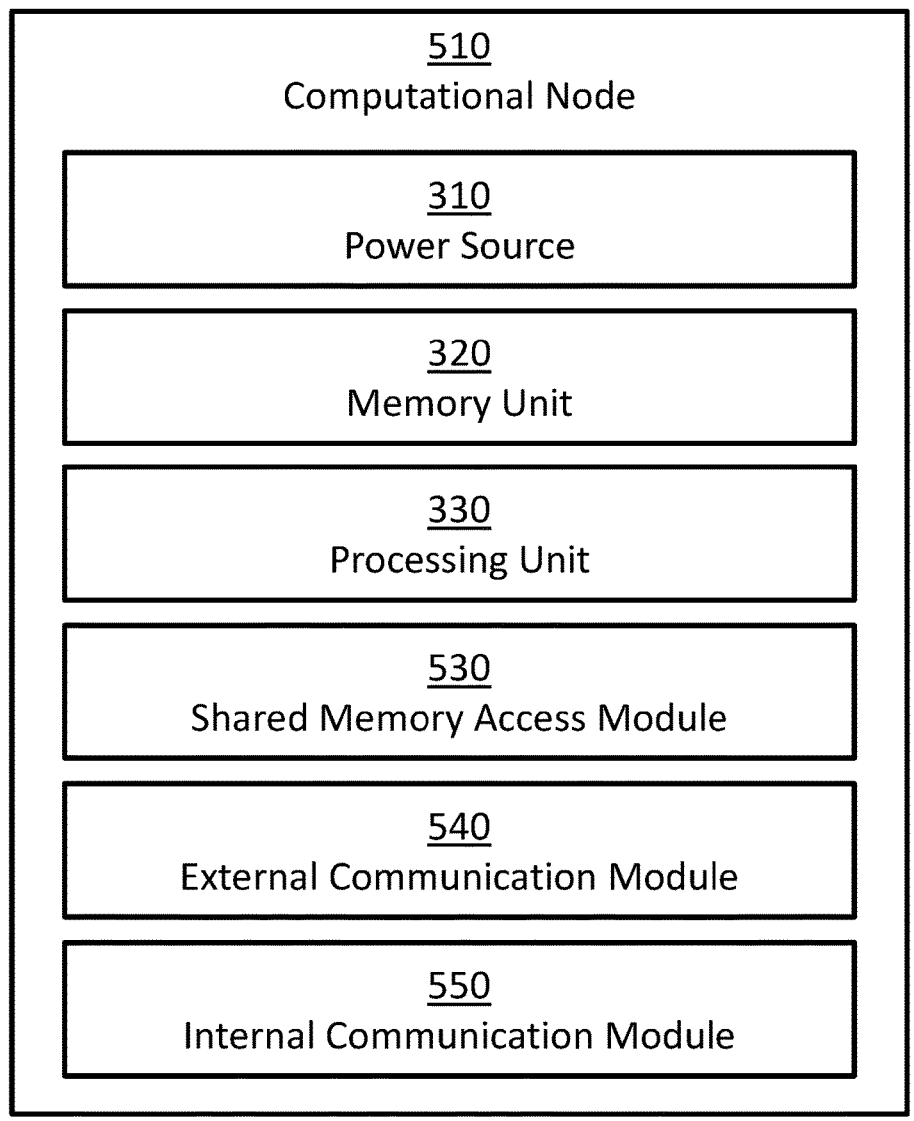
FIG. 5C is a block diagram illustrating a possible implementation of a computational node.

FIG. 5C is a block diagram illustrating a possible implementation of computational node 510 of a cloud platform, such as cloud platform 500. In this example computational node 510 comprises: one or more power sources 310; one or more memory units 320; one or more processing units 330; one or more shared memory access modules 530; one or more external communication modules 540; and one or more internal communication modules 550. In some implementations additional components may be included in computational node 510, while some components listed above may be excluded. In some embodiments, one or more of the followings may be excluded from the implementation of computational node 510: power sources 310; memory units 320; shared memory access modules 530; external communication modules 540; and internal communication modules 550. In some embodiments, computational node 510 may further comprise one or more of the followings: one or more audio output units 351; one or more visual outputting units 352; one or more tactile outputting units 353; one or more audio sensors 360; one or more image sensors 371; one or more accelerometers 373; one or more positioning sensors 374; one or more chemical sensors; one or more temperature sensors; one or more barometers; one or more environmental sensors; one or more pressure sensors; one or more proximity sensors; one or more electrical impedance sensors; one or more electrical voltage sensors; one or more electrical current sensors; one or more clocks; one or more user input devices; one or more keyboards; one or more mouses; one or more touch pads; one or more touch screens; one or more antennas; one or more output devices; one or more audio speakers; one or more display screens; one or more augmented reality display systems; one or more LED indicators; and so forth.

In some embodiments, external communication modules 540 and internal communication modules 550 may be implemented as a combined communication module, for example as communication modules 340. In some embodiments, one possible implementation of cloud platform 500 may comprise server 400. In some embodiments, one possible implementation of computational node 510 may comprise server 400. In some embodiments, one possible implementation of shared memory access modules 530 may comprise the usage of internal communication modules 550 to send information to shared memory modules 520 and/or receive information from shared memory modules 520. In some embodiments, node registration modules 570 and load balancing modules 560 may be implemented as a combined module.

In some embodiments, the one or more shared memory modules 520 may be accessed by more than one computational node. Therefore, shared memory modules 520 may allow information sharing among two or more computational nodes 510. In some embodiments, the one or more shared memory access modules 530 may be configured to enable access of computational nodes 510 and/or the one or more processing units 330 of computational nodes 510 to shared memory modules 520. In some examples, computational nodes 510 and/or the one or more processing units 330 of computational nodes 510, may access shared memory modules 520, for example using shared memory access modules 530, in order to perform one or more of: executing software programs stored on shared memory modules 520; store information in shared memory modules 520; retrieve information from the shared memory modules 520; and so forth.

In some embodiments, the one or more internal communication modules 550 may be configured to receive information from one or more components of cloud platform 500, and/or to transmit information to one or more components of cloud platform 500. For example, control signals and/or synchronization signals may be sent and/or received through internal communication modules 550. In another example, input information for computer programs, output information of computer programs, and/or intermediate information of computer programs, may be sent and/or received through internal communication modules 550. In another example, information received though internal communication modules 550 may be stored in memory units 320, in shared memory units 520, and so forth. In an additional example, information retrieved from memory units 320 and/or shared memory units 520 may be transmitted using internal communication modules 550. In another example, user input data may be transmitted and/or received using internal communication modules 550.

In some embodiments, the one or more external communication modules 540 may be configured to receive and/or to transmit information. For example, control signals and/or synchronization signals may be sent and/or received through external communication modules 540. In another example, information received though external communication modules 540 may be stored in memory units 320, in shared memory units 520, and so forth. In an additional example, information retrieved from memory units 320 and/or shared memory units 520 may be transmitted using external communication modules 540. In another example, input data may be transmitted and/or received using external communication modules 540. Examples of such input data may include: input data inputted by a user using user input devices; information captured from the environment of apparatus 300 using one or more sensors; and so forth. Examples of such sensors may include: audio sensors 360; image sensors 371; physiological sensors 372; accelerometers 373; and positioning sensors 374; chemical sensors; temperature sensors; barometers; environmental sensors; pressure sensors; proximity sensors; electrical impedance sensors; electrical voltage sensors; electrical current sensors; and so forth.

In some embodiments, the one or more node registration modules 570 may be configured to track the availability of the computational nodes 510. In some examples, node registration modules 570 may be implemented as: a software program, such as a software program executed by one or more of the computational nodes 510; a hardware solution; a combined software and hardware solution; and so forth. In some implementations, node registration modules 570 may communicate with computational nodes 510, for example using internal communication modules 550. In some examples, computational nodes 510 may notify node registration modules 570 of their status, for example by sending messages: at computational node 510 startups; at computational node 510 shutdowns; at periodic times; at selected times; in response to queries received from node registration modules 570; and so forth. In some examples, node registration modules 570 may query about computational nodes 510 status, for example by sending messages: at node registration module 570 startup; at periodic times; at selected times; and so forth.

In some embodiments, the one or more load balancing modules 560 may be configured to divide the work load among computational nodes 510. In some examples, load balancing modules 560 may be implemented as: a software program, such as a software program executed by one or more of the computational nodes 510; a hardware solution; a combined software and hardware solution; and so forth. In some implementations, load balancing modules 560 may interact with node registration modules 570 in order to obtain information regarding the availability of the computational nodes 510. In some implementations, load balancing modules 560 may communicate with computational nodes 510, for example using internal communication modules 550. In some examples, computational nodes 510 may notify load balancing modules 560 of their status, for example by sending messages: at computational node 510 startups; at computational node 510 shutdowns; at periodic times; at selected times; in response to queries received from load balancing modules 560; and so forth. In some examples, load balancing modules 560 may query about computational nodes 510 status, for example by sending messages: at load balancing module 560 startup; at periodic times; at selected times; and so forth.

Figure 6A:
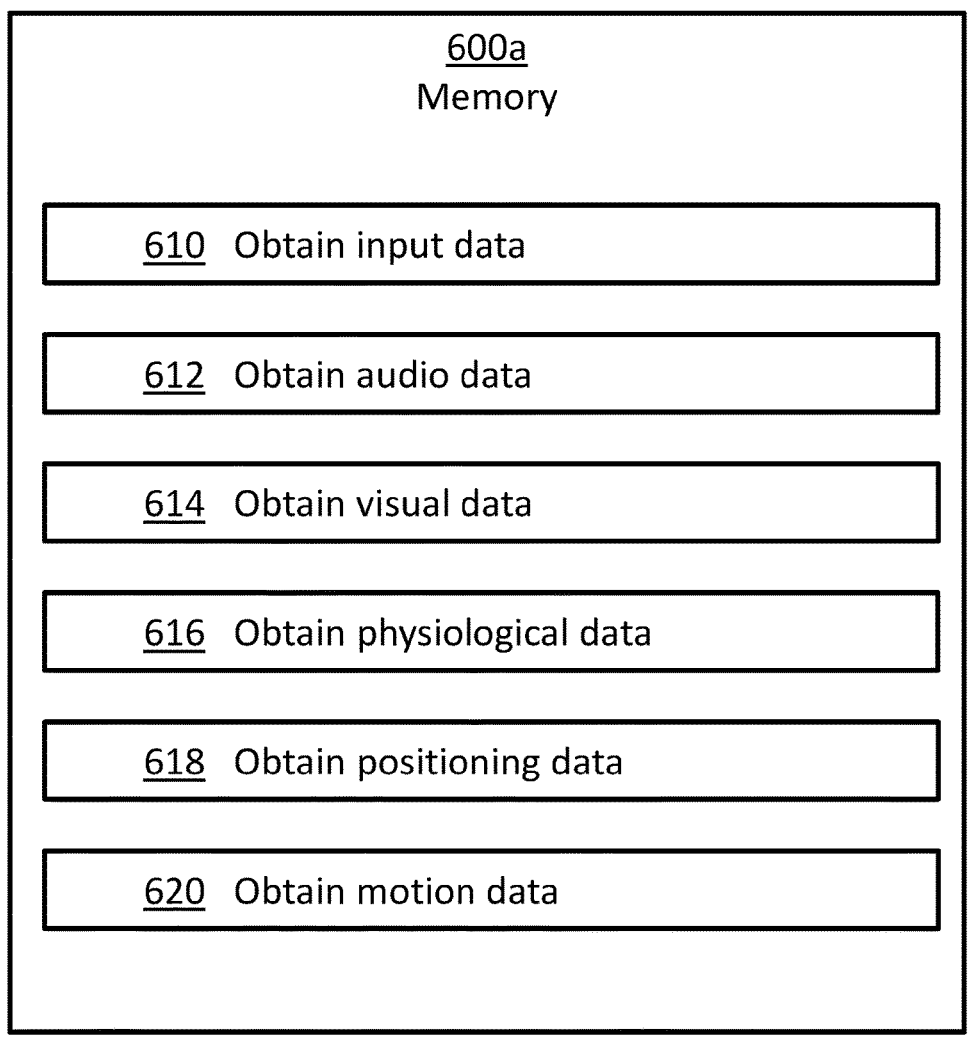
FIGS. 6A and 6B illustrate exemplary embodiments of memory containing software modules.
Figure 6B:
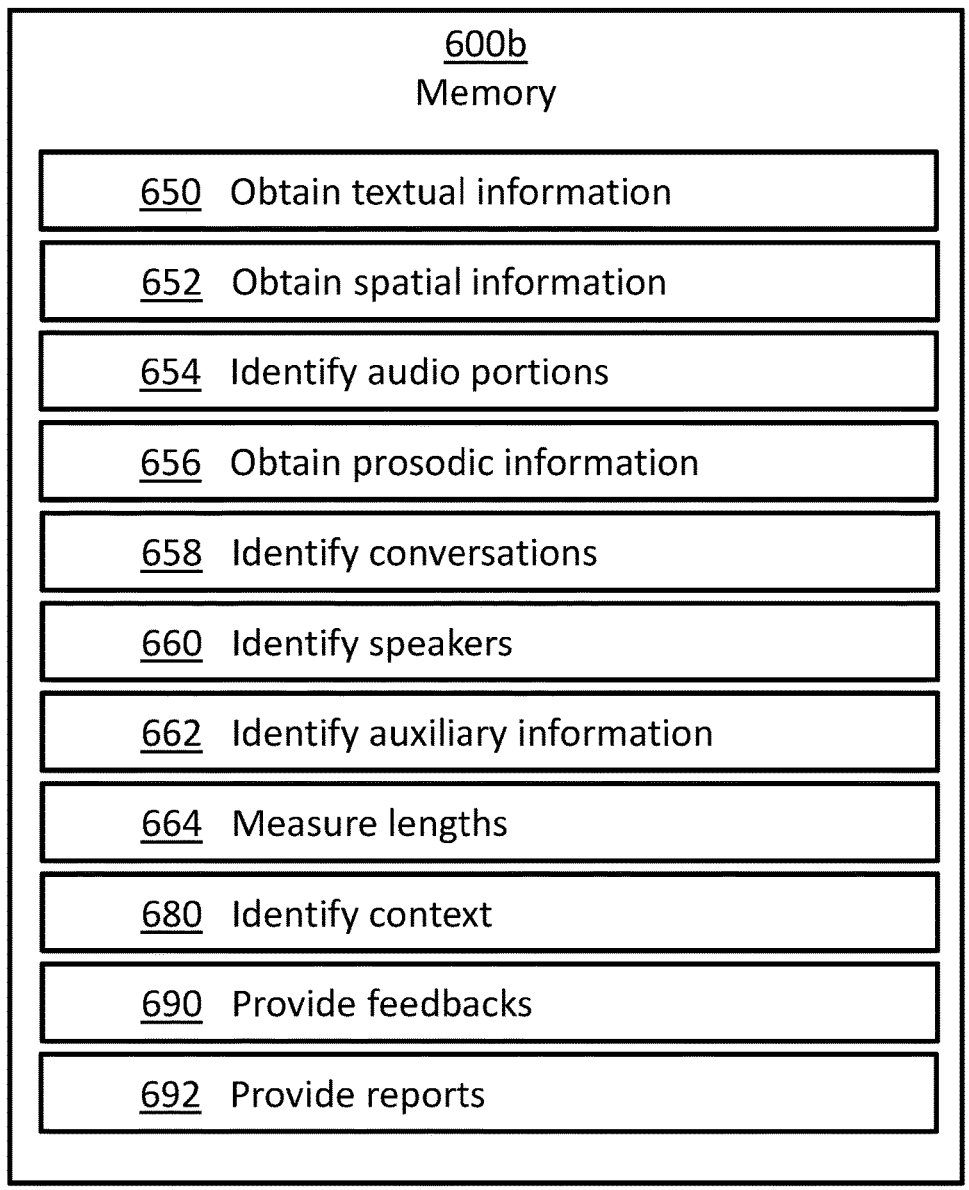

FIG. 6A illustrates an exemplary embodiment of memory 600a containing software modules, and FIG. 6B illustrates an exemplary embodiment of memory 600b containing software modules. In some examples, memory 600a may be separate and/or integrated with memory 600b. In addition, memory 600a and memory 600b may be separate from and/or integrated with memory units 320, separate from and/or integrated with shared memory modules 520, and so forth. In some examples, memory 600a and/or memory 600b may be included in a single device, such as apparatus 300, in server 400, in cloud platform 500, in computational node 510, and so forth. In some examples, at least one of memory 600a and memory 600b may be distributed across several devices, such as one or more apparatuses 300, one or more servers 400, one or more cloud platforms 500, one or more computational nodes 510, and so forth. Memory 600a and memory 600b may store more or fewer modules than those shown in FIGS. 6A and 6B. In this example, memory 600a may comprise: module for obtaining input data (610), module for obtaining audio data (612), module for obtaining visual data (614), module for obtaining physiological data (616), module for obtaining positioning data (618), and module for obtaining motion data (620). In this example, memory 600b may comprise: module for obtaining textual information (650), module for obtaining spatial information (652), module for identifying audio portions (654), module for obtaining prosodic information (656), module for identifying conversations (658), module for identifying speakers (660), module for identifying auxiliary information (662), module for measuring lengths (664), module for identifying context (680), module for providing feedbacks (690), and module for providing reports (692). The above modules may be implemented in software, hardware, firmware, a mix of any of those, or the like. For example, if the modules are implemented in software, they may contain software instructions for execution by at least one processing device, such as processing unit 330, by apparatus 300, by server 400, by cloud platform 500, by computational node 510, and so forth.

In some embodiments, obtaining input data (610) may comprise one or more of: obtaining audio data and/or preprocessed audio data, for example using module 612 for obtaining audio data; obtaining visual data and/or preprocessed visual data, for example using module 614 for obtaining visual data; obtaining physiological data and/or preprocessed physiological data, for example using module 616 for obtaining physiological data; obtaining positioning data and/or preprocessed positioning data, for example using module 618 for obtaining positioning data; obtaining motion data and/or preprocessed motion data, for example using module 620 for obtaining motion data; and so forth. In some embodiments, a user may wear a wearable apparatus comprising one or more sensors, such as a wearable version of apparatus 300, and obtaining input data (610) may comprise obtaining input data captured from the environment of the user using the input sensors.

In some embodiments, obtaining audio data (612) may comprise obtaining and/or capturing audio data from one or more audio sensors, for example using audio sensors 360. In some examples, the one or more audio sensors may comprise one or more wearable audio sensors, such as a wearable version of audio sensors 360. In some embodiments, obtaining audio data (612) may comprise receiving audio data from an external device, for example through a communication device such as communication modules 340, external communication modules 540, internal communication modules 550, and so forth. In some embodiments, obtaining audio data (612) may comprise reading audio data from memory, such as memory units 320, shared memory modules 520, and so forth. In some embodiments, obtaining audio data (612) may comprise obtaining audio data captured: continuously; at selected times; when specific conditions are met; upon a detection of a trigger; and so forth.

In some embodiments, obtaining audio data (612) may further comprise analyzing the audio data to obtain preprocessed audio data. One of ordinary skill in the art will recognize that the followings are examples, and that the audio data may be preprocessed using other kinds of preprocessing methods. In some examples, the audio data may be preprocessed by transforming the audio data using a transformation function to obtain a transformed audio data, and the preprocessed audio data may comprise the transformed audio data. For example, the transformation function may comprise a multiplication of a vectored time series representation of the audio data with a transformation matrix. For example, the transformation function may comprise convolutions, audio filters (such as low-pass filters, high-pass filters, band-pass filters, all-pass filters, etc.), nonlinear functions, and so forth. In some examples, the audio data may be preprocessed by smoothing the audio data, for example using Gaussian convolution, using a median filter, and so forth. In some examples, the audio data may be preprocessed to obtain a different representation of the audio data. For example, the preprocessed audio data may comprise: a representation of at least part of the audio data in a frequency domain; a Discrete Fourier Transform of at least part of the audio data; a Discrete Wavelet Transform of at least part of the audio data; a time/frequency representation of at least part of the audio data; a spectrogram of at least part of the audio data; a log spectrogram of at least part of the audio data; a Mel-Frequency Cepstrum of at least part of the audio data; a sonogram of at least part of the audio data; a periodogram of at least part of the audio data; a representation of at least part of the audio data in a lower dimension; a lossy representation of at least part of the audio data; a lossless representation of at least part of the audio data; a time order series of any of the above; any combination of the above; and so forth. In some examples, the audio data may be preprocessed to extract audio features from the audio data. Some examples of such audio features may include: auto-correlation; number of zero crossings of the audio signal; number of zero crossings of the audio signal centroid; MP3 based features; rhythm patterns; rhythm histograms; spectral features, such as spectral centroid, spectral spread, spectral skewness, spectral kurtosis, spectral slope, spectral decrease, spectral roll-off, spectral variation, etc.; harmonic features, such as fundamental frequency, noisiness, inharmonicity, harmonic spectral deviation, harmonic spectral variation, tristimulus, etc.; statistical spectrum descriptors; wavelet features; higher level features; perceptual features, such as total loudness, specific loudness, relative specific loudness, sharpness, spread, etc.; energy features, such as total energy, harmonic part energy, noise part energy, etc.; temporal features; and so forth.

In some embodiments, analysis of the audio data may be performed on the raw audio data and/or on the preprocessed audio data. In some examples, the analysis of the audio data and/or the preprocessed audio data may be based, at least in part, on one or more rules, functions, procedures, neural networks, inference models, and so forth. The rules, functions, procedures, neural networks, and inference models may be applied to the raw audio data and/or to the preprocessed audio data. Some examples of such inference models may comprise: a classification model; a regression model; an inference model preprogrammed manually; a result of training algorithms, such as machine learning algorithms and/or deep learning algorithms, on training examples, where the training examples may include examples of data instances, and in some cases, each data instance may be labeled with a corresponding desired label and/or result; and so forth.

In some embodiments, obtaining visual data (614) may comprise obtaining and/or capturing visual data, such as: images; video frames; sequence of images; video clips; continuous videos; 3D images; 3D video frames; sequence of 3D images; 3D video clips; continuous 3D video clips; any combination of the above; and so forth. In some embodiments, visual data obtained by module 614 may be synchronized with audio data obtained by module 612. In some embodiments, obtaining visual data (614) may comprise obtaining and/or capturing visual data from one or more image sensors, for example using image sensors 371. In some embodiments, the one or more image sensors may comprise one or more wearable image sensors, such as image sensors 371 included a wearable version of apparatus 300. In some embodiments, obtaining visual data (614) may comprise receiving visual data from an external device, for example through a communication device such as communication modules 340, external communication modules 540, internal communication modules 550, and so forth. In some embodiments, obtaining visual data (614) may comprise reading visual data from memory, such as memory units 320, shared memory modules 520, and so forth. In some embodiments, obtaining visual data (614) may comprise obtaining visual data captured: continuously; at selected times; when specific conditions are met; upon a detection of a trigger; and so forth.

In some embodiments, obtaining visual data (614) may further comprise analyzing the visual data to obtain preprocessed visual data. One of ordinary skill in the art will recognize that the followings are examples, and that the visual data may be preprocessed using other kinds of preprocessing methods. In some examples, the visual data may be preprocessed by transforming the visual data using a transformation function to obtain a transformed visual data, and the preprocessed visual data may comprise the transformed visual data. For example, the transformation function may comprise convolutions, visual filters (such as low-pass filters, high-pass filters, band-pass filters, all-pass filters, etc.), nonlinear functions, and so forth. In some examples, the visual data may be preprocessed by smoothing the visual data, for example using Gaussian convolution, using a median filter, and so forth. In some examples, the visual data may be preprocessed to obtain a different representation of the visual data. For example, the preprocessed visual data may comprise: a representation of at least part of the visual data in a frequency domain; a Discrete Fourier Transform of at least part of the visual data; a Discrete Wavelet Transform of at least part of the visual data; a time/frequency representation of at least part of the visual data; a representation of at least part of the visual data in a lower dimension; a lossy representation of at least part of the visual data; a lossless representation of at least part of the visual data; a time order series of any of the above; any combination of the above; and so forth. In some examples, the visual data may be preprocessed to extract edges, and the preprocessed visual data may comprise information based on and/or related to the extracted edges. In some examples, the visual data may be preprocessed to extract visual features from the visual data. Some examples of such visual features may comprise information based on and/or related to: edges; corners; blobs; ridges; Scale Invariant Feature Transform (SIFT) features; temporal features; and so forth.

In some embodiments, analysis of the visual data may be performed on the raw visual data and/or on the preprocessed visual data. In some examples, the analysis of the visual data and/or the preprocessed visual data may be based, at least in part, on one or more rules, functions, procedures, neural networks, inference models, and so forth. The rules, functions, procedures, neural networks, and inference models may be applied to the raw visual data and/or to the preprocessed visual data. Some examples of such inference models may comprise: a classification model; a regression model; an inference model preprogrammed manually; a result of training algorithms, such as machine learning algorithms and/or deep learning algorithms, on training examples, where the training examples may include examples of data instances, and in some cases, each data instance may be labeled with a corresponding desired label and/or result; and so forth.

In some embodiments, obtaining physiological data (616) may comprise obtaining and/or capturing physiological data from one or more physiological sensors, for example using physiological sensors 372. In some examples, one or more physiological sensors may comprise one or more wearable physiological sensors, such as physiological sensors 372 included in a wearable version of apparatus 300. Some examples of such physiological sensors may include: glucose sensors, electrocardiogram sensors, electroencephalogram sensors, electromyography sensors, odor sensors, respiration sensors, blood pressure sensors, pulse oximeter sensors, heart rate sensors, perspiration sensors, and so forth. In some embodiments, physiological data obtained by module 616 may be synchronized with audio data obtained by module 612 and/or with visual data obtained by module 614. In some embodiments, obtaining physiological data (616) may comprise receiving physiological data from an external device, for example through a communication device such as communication modules 340, external communication modules 540, internal communication modules 550, and so forth. In some embodiments, obtaining physiological data (616) may comprise reading physiological data from memory, such as memory units 320, shared memory modules 520, and so forth. In some embodiments, obtaining physiological data (616) may comprise obtaining physiological data captured: continuously; at selected times; when specific conditions are met; upon a detection of a trigger; and so forth.

In some embodiments, obtaining physiological data (616) may further comprise analyzing physiological data to obtain preprocessed physiological data. One of ordinary skill in the art will recognize that the followings are examples, and that the physiological data may be preprocessed using other kinds of preprocessing methods. In some examples, the physiological data may be preprocessed by transforming the physiological data using a transformation function to obtain a transformed physiological data, and the preprocessed physiological data may comprise the transformed physiological data. For example, the transformation function may comprise convolutions, filters (such as low-pass filters, high-pass filters, band-pass filters, all-pass filters, etc.), nonlinear functions, and so forth. In some examples, the physiological data may be preprocessed by smoothing the physiological data, for example using Gaussian convolution, using a median filter, and so forth. In some examples, the physiological data may be preprocessed to obtain a different representation of the physiological data. For example, the preprocessed physiological data may comprise: a representation of at least part of the physiological data in a frequency domain; a Discrete Fourier Transform of at least part of the physiological data; a Discrete Wavelet Transform of at least part of the physiological data; a time/frequency representation of at least part of the physiological data; a representation of at least part of the physiological data in a lower dimension; a lossy representation of at least part of the physiological data; a lossless representation of at least part of the physiological data; a time order series of any of the above; any combination of the above; and so forth. In some examples, the physiological data may be preprocessed to detect features within the physiological data, and the preprocessed physiological data may comprise information based on and/or related to the detected features.

In some embodiments, analysis of the physiological data may be performed on the raw physiological data and/or on the preprocessed physiological data. In some examples, the analysis of the physiological data and/or the preprocessed physiological data may be based, at least in part, on one or more rules, functions, procedures, neural networks, inference models, and so forth. The rules, functions, procedures, neural networks, and inference models may be applied to the raw physiological data and/or to the preprocessed physiological data. Some examples of such inference models may comprise: a classification model; a regression model; an inference model preprogrammed manually; a result of training algorithms, such as machine learning algorithms and/or deep learning algorithms, on training examples, where the training examples may include examples of data instances, and in some cases, each data instance may be labeled with a corresponding desired label and/or result; and so forth.

In some embodiments, obtaining positioning data (618) may comprise obtaining and/or capturing positioning data from one or more sensors, for example using positioning sensors 374. In some examples, the one or more sensors may comprise one or more wearable sensors, such as positioning sensors 374 included in a wearable version of apparatus 300. In some embodiments, positioning data obtained by module 618 may be synchronized with audio data obtained by module 612 and/or with visual data obtained by module 614 and/or with physiological data obtained by module 616. In some embodiments, obtaining positioning data (618) may comprise receiving positioning data from an external device, for example through a communication device such as communication modules 340, external communication modules 540, internal communication modules 550, and so forth. In some embodiments, obtaining positioning data (618) may comprise reading positioning data from memory, such as memory units 320, shared memory modules 520, and so forth. In some embodiments, obtaining positioning data (618) may comprise obtaining positioning data captured: continuously; at selected times; when specific conditions are met; upon a detection of a trigger; and so forth.

In some embodiments, obtaining positioning data (618) may further comprise analyzing positioning data to obtain preprocessed positioning data. One of ordinary skill in the art will recognize that the followings are examples, and that the positioning data may be preprocessed using other kinds of preprocessing methods. In some examples, the positioning data may be preprocessed by transforming the positioning data using a transformation function to obtain a transformed positioning data, and the preprocessed positioning data may comprise the transformed positioning data. For example, the transformation function may comprise convolutions, filters (such as low-pass filters, high-pass filters, band-pass filters, all-pass filters, etc.), nonlinear functions, and so forth. In some examples, the positioning data may be preprocessed by smoothing the positioning data, for example using Gaussian convolution, using a median filter, and so forth. In some examples, the positioning data may be preprocessed to obtain a different representation of the positioning data. For example, the preprocessed positioning data may comprise: a representation of at least part of the positioning data in a frequency domain; a Discrete Fourier Transform of at least part of the positioning data; a Discrete Wavelet Transform of at least part of the positioning data; a time/frequency representation of at least part of the positioning data; a representation of at least part of the positioning data in a lower dimension; a lossy representation of at least part of the positioning data; a lossless representation of at least part of the positioning data; a time order series of any of the above; any combination of the above; and so forth. In some examples, the positioning data may be preprocessed to detect features and/or patterns within the positioning data, and the preprocessed positioning data may comprise information based on and/or related to the detected features and/or the detected patterns. In some examples, the positioning data may be preprocessed by comparing the positioning data to positions of known sites to determine sites from the positioning data.

In some embodiments, analysis of the positioning data may be performed on the raw positioning data and/or on the preprocessed positioning data. In some examples, the analysis of the positioning data and/or the preprocessed positioning data may be based, at least in part, on one or more rules, functions, procedures, neural networks, inference models, and so forth. The rules, functions, procedures, neural networks, and inference models may be applied to the raw positioning data and/or to the preprocessed positioning data. Some examples of such inference models may comprise: a classification model; a regression model; an inference model preprogrammed manually; a result of training algorithms, such as machine learning algorithms and/or deep learning algorithms, on training examples, where the training examples may include examples of data instances, and in some cases, each data instance may be labeled with a corresponding desired label and/or result; and so forth.

In some embodiments, obtaining motion data (620) may comprise obtaining and/or capturing motion data from one or more sensors, for example using accelerometers 373 and/or gyroscopes and/or positioning sensors 374. In some examples, the one or more sensors may comprise one or more wearable sensors, such as accelerometers 373 and/or gyroscopes and/or positioning sensors 374 included in a wearable version of apparatus 300. In some embodiments, motion data obtained by module 620 may be synchronized with audio data obtained by module 612 and/or with visual data obtained by module 614 and/or with physiological data obtained by module 616 and/or with positioning data obtained by module 618. In some embodiments, obtaining motion data (620) may comprise receiving motion data from an external device, for example through a communication device such as communication modules 340, external communication modules 540, internal communication modules 550, and so forth. In some embodiments, obtaining motion data (620) may comprise reading motion data from memory, such as memory units 320, shared memory modules 520, and so forth. In some embodiments, obtaining motion data (620) may comprise obtaining motion data captured: continuously; at selected times; when specific conditions are met; upon a detection of a trigger; and so forth.

In some embodiments, obtaining motion data (620) may further comprise analyzing motion data to obtain preprocessed motion data. One of ordinary skill in the art will recognize that the followings are examples, and that the motion data may be preprocessed using other kinds of preprocessing methods. In some examples, the motion data may be preprocessed by transforming the motion data using a transformation function to obtain a transformed motion data, and the preprocessed motion data may comprise the transformed motion data. For example, the transformation function may comprise convolutions, filters (such as low-pass filters, high-pass filters, band-pass filters, all-pass filters, etc.), nonlinear functions, and so forth. In some examples, the motion data may be preprocessed by smoothing the motion data, for example using Gaussian convolution, using a median filter, and so forth. In some examples, the motion data may be preprocessed to obtain a different representation of the motion data. For example, the preprocessed motion data may comprise: a representation of at least part of the motion data in a frequency domain; a Discrete Fourier Transform of at least part of the motion data; a Discrete Wavelet Transform of at least part of the motion data; a time/frequency representation of at least part of the motion data; a representation of at least part of the motion data in a lower dimension; a lossy representation of at least part of the motion data; a lossless representation of at least part of the motion data; a time order series of any of the above; any combination of the above; and so forth. In some examples, the motion data may be preprocessed to detect features and/or motion patterns within the motion data, and the preprocessed motion data may comprise information based on and/or related to the detected features and/or the detected motion patterns.

In some embodiments, analysis of the motion data may be performed on the raw motion data and/or on the preprocessed motion data. In some examples, the analysis of the motion data and/or the preprocessed motion data may be based, at least in part, on one or more rules, functions, procedures, neural networks, inference models, and so forth. The rules, functions, procedures, neural networks, and inference models may be applied to the raw motion data and/or to the preprocessed motion data. Some examples of such inference models may comprise: a classification model; a regression model; an inference model preprogrammed manually; a result of training algorithms, such as machine learning algorithms and/or deep learning algorithms, on training examples, where the training examples may include examples of data instances, and in some cases, each data instance may be labeled with a corresponding desired label and/or result; and so forth.

In some embodiments, obtaining textual information (650) may comprise analyzing the audio data and/or the preprocessed audio data to obtain information, including textual information. In some examples, obtaining textual information (650) may comprise using speech to text algorithms to transcribe spoken language in the audio data. In some examples, obtaining textual information (650) may comprise: analyzing the audio data and/or the preprocessed audio data to identify words, keywords, and/or phrases in the audio data, for example using sound recognition algorithms; and representing the identified words, keywords, and/or phrases, for example in a textual manner, using graphical symbols, in a vector representation, as a pointer to a database of words, keywords, and/or phrases, and so forth. In some examples, obtaining textual information (650) may comprise: analyzing the audio data and/or the preprocessed audio data using sound recognition algorithms to identify nonverbal sounds in the audio data; and describing the identified nonverbal sounds, for example in a textual manner, using graphical symbols, as a pointer to a database of sounds, and so forth. In some examples, obtaining textual information (650) may comprise using acoustic fingerprint based algorithms to identify items in the audio data. Some examples of such items may include: songs, melodies, tunes, sound effects, and so forth. The identified items may be represented: in a textual manner; using graphical symbols; as a pointer to a database of items; and so forth. In some examples, obtaining textual information (650) may comprise analyzing the audio data and/or the preprocessed audio data to obtain properties of voices present in the audio data, including properties associated with: pitch, intensity, tempo, rhythm, prosody, flatness, and so forth. In some examples, obtaining textual information (650) may comprise: recognizing different voices, for example in different portions of the audio data; and/or identifying different properties of voices present in different parts of the audio data. As a result, different portions of the textual information may be associated with different voices and/or different properties. In some examples, different portions of the textual information may be associated with different textual formats, such as layouts, fonts, font sizes, font styles, font formats, font typefaces, and so forth. For example, different portions of the textual information may be associated with different textual formats based on different voices and/or different properties associated with the different portions of the textual information. Some examples of such speech to text algorithms and/or sound recognition algorithms may include: hidden Markov models based algorithms; dynamic time warping based algorithms; neural networks based algorithms; machine learning and/or deep learning based algorithms; and so forth.

In some embodiments, obtaining spatial information (652) may comprise obtaining spatial information associated with the audio data. In some examples, the obtained spatial information may be synchronized with the audio data. In some examples, the obtained spatial information may comprise location information related to the location of: one or more sound sources associated with sounds present in the audio data; one or more speakers associated with speech present in the audio data; and so forth. Some examples of location information may include information associated with one or more of: direction; distance; 2D position; 3D position; absolute position; relative position; any combination of the above; and so forth. In some examples, location information may be: associated with a single point in time; associated with multiple points in time; associated with a range of times; continuous; and so forth.

In some embodiments, obtaining spatial information (652) may comprise analyzing the audio data and/or the preprocessed audio data to obtain spatial information. In some embodiments, obtaining spatial information (652) may comprise analyzing the audio data and/or the preprocessed audio data using sound localization algorithms to obtain location information associated with sounds and/or speech present in the audio data. Some examples of sound localization algorithms may include: steered beamformer approach based algorithms; collocated microphone array based algorithms; binaural hearing learning based algorithms; head related transfer function based algorithms; cross power spectrum phase based algorithms; 2D sensor line array based algorithms; hierarchical algorithms; neural networks based algorithms; triangulation algorithms; time of arrival based algorithms; particle velocity based algorithms; and so forth. In some embodiments, obtaining spatial information (652) may comprise obtaining estimated direction of arrival associated with the audio data, and in some cases, the location information may be based on the estimated direction of arrival.

In some embodiments, obtaining spatial information (652) may comprise analyzing the visual data and/or the preprocessed visual data to obtain spatial information, such as: location information associated with one or more sound sources visible in the visual data; location information associated with one or more speakers visible in the visual data; and so forth. In some examples, a speaker location in 2D image and/or 2D video may be detected using detection algorithms, for example by face detection algorithms, by algorithms that detect lips movements, etc., and location information may be calculated, for example: a direction may be calculated based on the based on the speaker location in the 2D image and/or 2D video and/or the capturing parameters; a distance may be calculated based on the based on the speaker location in the 2D image and/or 2D video and/or the capturing parameters; and so on. In some examples, a speaker location in 3D image and/or 3D video may be detected using detection algorithms, therefore obtaining location information, such as direction, distance, position, and so forth. In some examples, stereopsis methods may be applied on the visual data and/or the preprocessed visual data to obtain the location information.

In some embodiments, obtaining spatial information (652) may comprise associating a speaker visible in the visual data with one or more portions of speech in the audio data. For example, detection of lips movement at a certain time may hint an association of the speaker moving the lips with speech present in the audio data at the same time. In an additional example, correspondence between an estimated direction associated with the audio data and an estimated direction of a person and/or a face appearing in the visual data may hint an association of the person and/or face with speech present in the audio data at the same time. In some examples, these hints may be aggregated, and after a certain confidence threshold is exceeded, a speaker may be associated with specific portions of speech in the audio data. In some examples, the confidence level may be based, at least in part, on correspondence between speaker diarization of the audio data and on appearance of specific people in the visual data over time, for example based on tracking algorithms, based on face recognition algorithms, and so forth. In some examples, a database of associations of face information with voice profiles may be accessed, a speaker may be associated with one or more portions of speech in the audio data that match the speaker voice profile, the speaker may be detected in the visual data based on the face information, and an association may be made between the one or more portions of speech matching the voice profile and information based on the detection in the visual data.

In some embodiments, obtaining spatial information (652) may comprise obtaining directional information associated of one speaker with respect to another speaker. For example, the directional information may comprise information associated with at least one of: relative direction, relative distance, relative position, and so forth. In some examples, location information for two speakers may be obtained, for example as described above, and relative location information of one speaker with respect to another speaker may be calculated. For example, given direction and distance of the two speakers from the same point, the relative direction and distance may be obtain through subtraction of the two vectors. In another example, given two absolute positions, the relative position may be obtained through subtraction of one position from the other. In some cases, the location of a speaker may be calculated with respect to sensors, such as audio sensors 360 and/or image sensors 371, and in case the sensors are wearable sensors configured to be worn by one of the speakers, the relative location of a speaker may be based on the location information calculated for that speaker.

In some embodiments, obtaining spatial information (652) may comprise obtaining spatial orientation information associated with one or more speakers. For example, spatial orientation information may be associated with a wearer of a wearable sensor, of a speaker speaking in the captured audio data, of a person and/or a speaker visible in the captured visual data, and so forth.

In some embodiments, information captured using one or more wearable sensors configured to be worn by a wearer may be obtained, and the spatial orientation information associated with the wearer may comprise the orientation of at least one wearable sensor with respect to the wearer. In some examples, the orientation of the at least one wearable sensor with respect to the wearer may be obtained using: an accelerometer, such as accelerometer 373; a gyroscope; an image sensor, such as image sensor 371; and so forth. In some examples, the at least one wearable sensor may comprise a wearable image sensor, such as a wearable version of image sensor 371, and the orientation of the at least one wearable sensor with respect to the wearer may be obtained: by detecting the horizon in the captured images, by identifying in the captured images a specific body part of the wearer (such as head, torso, etc.), and so forth. In some examples, the at least one wearable sensor may comprise a wearable audio sensor, such as a wearable version of audio sensor 360, and the orientation of the at least one wearable sensor with respect to the wearer and/or the mouth of the wearer may be based on the directional information associated with the wearer, where the directional information associated with the wearer may be obtained as described above.

In some embodiments, the visual data and/or the preprocessed visual data may be analyzed to obtain spatial orientation information associated with one or more speakers. For example, the torso of a speaker may be detected, and the orientation may be obtained by determining the orientation of the torso. In another example, the head and/or face of the speaker may be detected, and the orientation may be obtained by determining the orientation of the head and/or face. In another example, at least one eye or parts of at least one eye may be detected in the visual data and/or the preprocessed visual data, and the orientation may be obtained by determining the orientation of the speaker gaze, for example using eye tracking algorithms.

In some embodiments, identifying audio portions (654) may comprise analyzing the audio data and/or the preprocessed audio data to identify one or more portions of the audio data. In some examples, an identified portion of the audio data may comprise a continuous part of the audio data or a non-continuous part of the audio data. In some examples, at least one of the one or more portions of the audio data may correspond to at least one of: a silent part of the audio data; a part of the audio data that does not contain speech; a utterance; a phoneme; a syllable; a morpheme; a word; a sentence; a conversation; a number of phonemes; a number of syllables; a number of morphemes; a number of words; a number of sentences; a number of conversations; a continuous part of the audio data corresponding to a single speaker; a non-continuous part of the audio data corresponding to a single speaker; a continuous part of the audio data corresponding to a group of speakers; a non-continuous part of the audio data corresponding to a group of speakers; and so forth.

In some embodiments, identifying audio portions (654) may comprise analyzing the audio data and/or the preprocessed audio data using one or more rules to identify one or more portions of the audio data. In some examples, at least part of the one or more rules may be read from memory. In some examples, at least part of the one or more rules may be preprogrammed manually. In some examples, at least part of the one or more rules may be the result of training algorithms, such as machine learning algorithms and/or deep learning algorithms, on training examples. The training examples may include examples of data instances, and in some cases, each data instance may be labeled with a corresponding desired label and/or result. In some embodiments, the identification of the one or more portions of the audio data may be based, at least in part, on the output of one or more neural networks.

In some embodiments, identifying audio portions (654) may comprise: analyzing the audio data and/or the preprocessed audio data to obtain textual information, for example using module 650; and analyzing of the textual information to identify one or more portions of the audio data. For example, the textual information may comprise a transcription of at least part of the audio data. The textual information may be analyzed in order to identify one or more portions of the textual information corresponding to at least one of: part of the textual information that does not contain meaningful text; a utterance; a phoneme; a syllable; a morpheme; a word; a sentence; a conversation; a number of phonemes; a number of syllables; a number of morphemes; a number of words; a number of sentences; a number of conversations; continuous part of the textual information corresponding to a single speaker; non-continuous part of the textual information corresponding to a single speaker; continuous part of the textual information corresponding to a group of speakers; non-continuous part of the textual information corresponding to a group of speakers; and so forth. One or more portions of the audio data corresponding to the one or more portions of the textual information may be identified. In some examples, the textual information may be analyzed using: natural language processing algorithms, neural networks algorithms, machine learning algorithms and/or deep learning algorithms, and so forth.

In some embodiments, identifying audio portions (654) may comprise analyzing the audio data and/or the preprocessed audio data to identify one or more portions of the audio data associated with a speaker. In some examples, speaker diarization algorithms may be applied to identify the speaking time of each speaker in the audio data, therefore identifying portions of the audio data associated with selected speakers. In some examples, speaker recognition algorithms may be applied to identify when a specified speaker is speaking in the audio data, and/or to identify portions of the audio data associated with selected speakers. In some cases, a speaker may be identified as the wearer of a wearable apparatus, such as a wearable version of apparatus 300. One or more portions of the audio data may be identified as associated with the wearer. One or more portions of the audio data may be identified as associated with a speaker other than the wearer. One or more portions of the audio data may be identified as associated a group of a plurality of speakers, for example where the group of a plurality of speakers does not include the wearer.

In some embodiments, identifying audio portions (654) may comprise analyzing the audio data and/or the preprocessed audio data to identify one or more portions of the audio data based, at least in part, on spatial information associated with the audio data. In some examples, one or more portions of the audio data associated with a selected direction and/or selected range of directions may be identified. For example, the spatial information may comprise directional information of sound sources associated with sounds present in the audio data, directional information associated with speech present in the audio data, and/or directional information associated with speakers, and the one or more portions of the audio data that contain sounds and/or speech associated with a selected direction and/or selected range of directions may be identified. For example, the audio data may comprise audio data captured using a wearable apparatus comprising one or more audio sensors, such as a wearable version of apparatus 300. In such example, the wearer of the wearable apparatus may be associated with a selected direction and/or selected range of directions, and one or more portions of the audio data that contain sounds and/or speech associated with the selected direction and/or the selected range of directions may be identified.

In some embodiments, obtaining prosodic information (656) may comprise analyzing the audio data and/or the preprocessed audio data to obtain prosodic information. The prosodic information may be associated with a group of one or more portions of the audio data and/or with one or more points in time and/or with one or more points in the audio data. For example, the prosodic information may be associated with a group of one or more portions of the audio data that were identified, for example as described above, as associated with a given speaker, a given conversation, a given context, and so forth. In some examples, a group of one or more portions of the audio data and/or a group of one or more portions of the preprocessed audio data may be analyzed to obtain prosodic information associated with a group of one or more portions of the audio data.

In some embodiments, the prosodic information may comprise information associated with speech rhythm. For example, duration of speech sounds may be measured. Some examples of such speech sounds may include: vowels, consonants, syllables, utterances, and so forth. In some cases, statistics related to the duration of speech sounds may be gathered. In some examples, the variance of vowel duration may be calculated. In some examples, the percentage of speech time dedicated to one type of speech sounds may be measured. In some examples, contrasts between durations of neighboring vowels may be measured.

In some embodiments, the prosodic information may comprise information associated with speech tempo. For example, speaking rate may be measured. For example, articulation rate may be measured. In some cases, the number of syllables per a unit of time may be measured, where the unit of time may include and/or exclude times of pauses, hesitations, and so forth. In some cases, the number of words per a unit of time may be measured, where the unit of time may include and/or exclude times of pauses, hesitations, and so forth. In some cases, statistics related to the rate of syllables may be gathered. In some cases, statistics related to the rate of words may be gathered.

In some embodiments, the prosodic information may comprise information associated with pitch of the voice. For example, pitch may be measured at specified times, randomly, continuously, and so forth. In some cases, statistics related to the pitch may be gathered. In some cases, pitch may be measured at different segments of speech, and statistics related to the pitch may be gathered for each type of segment separately. In some cases, the average speaking pitch over a time period may be calculated. In some cases, the minimal and/or maximal speaking pitch in a time period may be found.

In some embodiments, the prosodic information may comprise information associated with loudness of the voice. For example, the loudness may be measured as the intensity of the voice. For example, loudness may be measured at specified times, randomly, continuously, and so forth. In some cases, statistics related to the loudness may be gathered. In some cases, loudness may be measured at different segments of speech, and statistics related to the loudness may be gathered for each type of segment separately. In some cases, the average speaking loudness over a time period may be calculated. In some cases, the minimal and/or maximal speaking loudness in a time period may be found.

In some embodiments, the prosodic information may comprise information associated with intonation of the voice. For example, the pitch of the voice may be analyzed to identify rising and falling intonations. In another example, rising intonation, falling intonation, dipping intonation, and/or peaking intonation may be identified. For example, intonation may be identified at specified times, randomly, continuously, and so forth. In some cases, statistics related to the intonation may be gathered.

In some embodiments, the prosodic information may comprise information associated with a linguistic tone associated with a portion of the audio data. For example, the usage of pitch to distinguish and/or inflect words, to express emotional and/or paralinguistic information, to convey emphasis, contrast, and so forth, may be identified. Some examples of linguistic tone may include: abashed, abrasive, abusive, accepting, acquiescent, admiring, adoring, affectionate, aggravated, aghast, allusive, amused, angry, anxious, apologetic, appreciative, apprehensive, approving, arch, ardent, argumentative, artificial, ashamed, audacious, authoritative, awe-struck, bantering, begrudging, bemused, benevolent, biting, bitter, blithe, boastful, bored, bristling, brusque, calm, candid, caring, caustic, cavalier, cheerful, childish, child-like, clipped, cold, compassionate, complimentary, condemning, condescending, confident, contemptuous, conversational, coy, critical, curt, cutting, cynical, denunciatory, despairing, detached, didactic, disappointed, disbelieving, disconcerted, discouraged, disdainful, disgusted, disinterested, disparaging, disrespectful, distracted, doubtful, dramatic, dreamy, dry, ecstatic, embarrassed, energetic, entranced, enthusiastic, eulogistic, excited, exhilarated, exultant, facetious, fanciful, fearful, flippant, fond, forceful, friendly, frightened, ghoulish, giddy, gleeful, glum, grim, guarded, guilty, happy, harsh, hateful, haughty, heavy-hearted, hollow, horrified, humorous, hypercritical, indifferent, indignant, indulgent, inflammatory, insulting, ironic, irreverent, irritated, joking, joyful, languorous, languid, laudatory, light-hearted, lingering, loving, manipulative, marveling, melancholy, mistrustful, mocking, mysterious, naive, negative, neutral, nostalgic, objective, passionate, patronizing, peaceful, pessimistic, pitiful, playful, poignant, positive, pragmatic, proud, provocative, questioning, rallying, reflective, reminiscing, reproachful, resigned, respectful, restrained, reticent, reverent, ridiculing, romantic, rueful, sad, sarcastic, sardonic, satiric, satisfied, seductive, self-critical, self-dramatizing, self-justifying, self-mocking, self-pitying, self-satisfied, sentimental, serious, severe, sharp, shocked, silly, sly, smug, solemn, somber, stentorian, stern, straightforward, strident, stunned, subdued, surprised, swaggering, sweet, sympathetic, taunting, teasing, tense, thoughtful, threatening, tired, touchy, trenchant, uncertain, understated, upset, urgent, vexed, vibrant, wary, whimsical, withering, wry, zealous, and so forth.

In some embodiments, the prosodic information may comprise information associated with stress of the voice. For example, loudness of the voice and/or vowels length may be analyzed to identify an emphasis given to a specific syllable. In another example, loudness of the voice and pitch may be analyzed to identify emphasis on specific words, phrases, sentences, and so forth. In an additional example, loudness, vowel length, articulation of vowels, pitch, and so forth may be analyzed to identify emphasis associated with a specific time of speaking, with specific portions of speech, and so forth.

In some embodiments, the prosodic information may comprise information associated with pauses. For example, length of pauses may be measured. In some cases, statistics related to the length of pauses may be gathered.

In some embodiments, the prosodic information may comprise information associated with timbre of the voice. For example, voice brightness may be identified. As another example, formant structure associated with the pronunciation of the different sounds may be identified. In some embodiments, the prosodic information may comprise information associated with accent. For example, the type of accent may be identified. In some embodiments, the prosodic information may comprise an identification of flatness level of a voice.

In some embodiments, obtaining prosodic information (656) may comprise analyzing the audio data and/or the preprocessed audio data using one or more rules to obtain prosodic information. In some examples, at least part of the one or more rules may be read from memory. In some examples, at least part of the one or more rules may be received from an external device, for example using a communication device. In some examples, at least part of the one or more rules may be preprogrammed manually. In some examples, at least part of the one or more rules may be the result of training algorithms, such as machine learning algorithms and/or deep learning algorithms, on training examples. The training examples may include examples of data instances, and in some cases, each data instance may be labeled with a corresponding desired label and/or result. For example, the training examples may include audio samples that contain speech, and be labeled according to the prosodic properties of the contained speech. In some embodiments, the identification of the prosodic information may be based, at least in part, on the output of one or more neural networks.

In some embodiments, identifying conversations (658) may comprise obtaining an indication that two or more speakers are engaged in conversation. For example, speaker diarization information may be obtained, for example by using a speaker diarization algorithm. The speaker diarization information may be analyzed in order to identify which speakers are engaged in conversation at what time, for example by detecting a sequence in time in which two or more speakers talk in turns. In another example, clustering algorithms may be used to analyze the speaker diarization information and divide the speaker diarization information to conversations. In another example, the speaker diarization information may be divided when no activity is recorder in the speaker diarization information for duration longer than a selected threshold.

In some embodiments, identifying conversations (658) may comprise analyzing the audio data and/or the preprocessed audio data to identify a conversation in the audio data. Some examples of such analysis methods may include: the application of speaker diarization algorithms in order to obtain speaker diarization information, and analyzing the speaker diarization information as described above; the usage of neural networks trained to detect conversations within audio data, where the input to the neural networks may comprise the audio data and/or the preprocessed audio data; analyzing the audio data and/or the preprocessed audio data to obtain textual information, for example using module 650, and analyzing of the textual information to identify conversations, for example using textual conversation identification algorithms; and so forth. In some examples, speakers taking part in that conversation may be identified, for example using speaker recognition algorithms. Some examples of such speaker recognition algorithms may include: pattern recognition algorithms; hidden Markov models based algorithms; mixture of Gaussians based algorithms; pattern matching based algorithms; neural networks based algorithms; quantization based algorithms; machine learning and/or deep learning based algorithms; and so forth.

In some embodiments, identifying conversations (658) may comprise analyzing the visual data and/or the preprocessed visual data to identify a conversation involving two or more speakers visible in the visual data, and possibly in order to identify the speakers taking part in the conversation, for example using face recognition algorithms. Some examples of such analysis may comprise: usage of action recognition algorithms; usage of lips reading algorithms; and so forth.

In some embodiments, identifying conversations (658) may comprise analyzing information coming from variety of sensors, for example identifying conversations based on an analysis of audio data and visual data.

In some embodiments, identifying speakers (660) may comprise obtaining identifying information associated with one or more speakers. In some examples, identifying speakers (660) may identify the name of one or more speakers, for example by accessing a database that comprises names and identifying audible and/or visual features. In some examples, identifying speakers (660) may identify demographic information associated with one or more speakers, such as age, sex, and so forth. In some embodiments, identifying speakers (660) may comprise analyzing the input data using one or more rules to determine demographic information associated with one or more speakers, such as age, sex, and so forth. In some examples, at least part of the one or more rules may be read from memory. In some examples, at least part of the one or more rules may be preprogrammed manually. In some examples, at least part of the one or more rules may be the result of training algorithms, such as machine learning algorithms and/or deep learning algorithms, on training examples. The training examples may include examples of data instances, and in some cases, each data instance may be labeled with a corresponding desired label and/or result. For example, the training examples may include audio samples that contain speech, and be labeled according to the age and/or sex of the speaker. In another example, the training examples may include images that contain faces, and be labeled according to the age and/or sex of the faces. In some embodiments, the determining demographic information may be based, at least in part, on the output of one or more neural networks.

In some embodiments, identifying speakers (660) may comprise analyzing the audio data and/or the preprocessed audio data to identify one or more speakers and/or to identify information associated with one or more speakers, for example using speaker recognition algorithms. Some examples of such speaker recognition algorithms may include: pattern recognition algorithms; hidden Markov models based algorithms; mixture of Gaussians based algorithms; pattern matching based algorithms; neural networks based algorithms; quantization based algorithms; machine learning and/or deep learning based algorithms; and so forth.

In some embodiments, identifying speakers (660) may comprise analyzing the visual data and/or the preprocessed visual data to detect one or more speakers and/or to identify one or more speakers and/or to identify information associated with one or more speakers, for example using lips movement detection algorithms, face recognition algorithms, and so forth.

In some embodiments, identifying auxiliary information (662) may comprise analyzing the audio data and/or the preprocessed audio data to obtain auxiliary information. In some examples, the auxiliary information may comprise identifying one or more portions of the audio data, such as the one or more portions of the audio data identified by analyzing the audio data and/or the preprocessed audio data, for example using module 654. In some examples, the auxiliary information may comprise information associated with one or more properties of a voice of the wearer, such as: prosody, pitch, intensity, tempo, rhythm, flatness, and so forth. In some examples, the auxiliary information may comprise information associated with a comparison of one or more properties of a voice of the wearer and one or more voices of other speakers, such as: prosody, pitch, intensity, tempo, rhythm, flatness, and so forth. For example, at least part of the one or more properties of a voice may be identified by analyzing the audio data and/or the preprocessed audio data using module 656. In some examples, the auxiliary information may comprise information associated with nonverbal information associated with at least one of: emotional state of the speaker, interest level of the speaker, and so forth. In some examples, the auxiliary information may comprise information associated with nonverbal information, such as: laughter, crying, nonverbal vocal sounds, pauses, and so forth. In some examples, the auxiliary information may comprise information associated with nonverbal information: associated with the wearer; associated with two or more speakers, where at least one of the two or more speakers is the wearer; associated with one or more speakers, none of the one or more speakers is the wearer; and so forth. For example, the audio data and/or the preprocessed audio data using sound recognition algorithms to identify nonverbal sounds in the audio data, such as laughter, crying, nonverbal vocal sounds, and so forth. For example, the audio data and/or the preprocessed audio data using speech recognition algorithms to identify pauses.

In some examples, the auxiliary information may comprise information related to one or more conversations, for examples information obtained by analyzing the audio data and/or the preprocessed audio data using module 658. In some examples, the auxiliary information may comprise information related to one or more conversations involving the wearer and one or more other speakers, such as: instances in which the wearer was involved in conversation; number of times the wearer was involved in conversation; instances in which the wearer initiated the conversation; number of times the wearer initiated the conversation; instances in which the wearer did not initiated the conversation; number of conversations the wearer did not initiated; instances in which the wearer ended the conversation; number of times the wearer ended the conversation; instances in which the wearer did not ended the conversation; number of conversation the wearer did not ended; length of at least one of the one or more conversations; number of participants in at least one of the one or more conversations; instances in which the wearer speaks; amount of time the wearer speaks; instances in which at least one of the one or more other speakers speaks; amount of time at least one of the one or more other speakers speaks; and so forth. For example, such information may be obtained by analyzing speaker diarization information, by using speech recognition algorithms, and so forth.

In some embodiments, measuring lengths (664) may comprise obtaining a measurement associated with the length of one or more segments of the audio data, or a measurement associated with the length of information associated with one or more segments of the audio data, for example by analyzing the audio data and/or the preprocessed audio data.

In some embodiments, measuring lengths (664) may comprise obtaining a measurement associated with the length of time of at least one of the following segments of the audio data: the entire audio data; a silent part of the audio data; a part of the audio data that does not contain speech; a part of the audio data that contains speech; a utterance; a phoneme; a syllable; a morpheme; a word; a sentence; a question; a conversation; a number of phonemes; a number of syllables; a number of morphemes; a number of words; a number of sentences; a number of conversations; a continuous part of the audio data; a non-continuous part of the audio data; a continuous part of the audio data corresponding to a single speaker; a non-continuous part of the audio data corresponding to a single speaker; a continuous part of the audio data corresponding to a group of speakers; a non-continuous part of the audio data corresponding to a group of speakers; any combination of the above; and so forth.

In some embodiments, measuring lengths (664) may comprise obtaining a measurement associated with the length of a segment of the audio data, or a measurement associated with the length of information associated with a segment of the audio data, may be measured by counting the number of objects contained within the segment, or within the information associated with the segment. Some examples of such objects may include: a phoneme; a syllable; a morpheme; a word; a utterance; a sentence; a question; a conversation; and so forth. For example, a length of syllable may be measured by counting the number of phonemes contained within the syllable. In another example, a length of a morpheme may be measured by counting the number of phonemes or syllables contained within the morpheme. In an additional example, the length of a word may be measured by counting the number of phonemes, syllables, or morphemes contained within the word. In another example, the length of a utterance, a sentence or a question may be measured by counting the number of phonemes, syllables, morphemes or words contained within the utterance, the sentence, or the question. In an additional example, the length of a conversation or a part of a conversation may be measured by counting the number of phonemes, syllables, morphemes, words, utterances, sentences, or questions contained within the conversation or the part of a conversation. In another example, the length of a part of the audio data corresponding to a single speaker may be measured by counting the number of phonemes, syllables, morphemes, words, utterances, sentences, questions or conversations contained within the part of the audio data corresponding to a single speaker.

In some embodiments, measuring lengths (664) may comprise analyzing the audio data and/or the preprocessed audio data and/or information associated with a segment of the audio data using one or more rules. In some examples, at least part of the one or more rules may be read from memory. In some examples, at least part of the one or more rules may be preprogrammed manually. In some examples, at least part of the one or more rules may be the result of training algorithms, such as machine learning algorithms and/or deep learning algorithms, on training examples. The training examples may include examples of data instances, and in some cases, each data instance may be labeled with a corresponding desired label and/or result. In some embodiments, measuring lengths (664) may comprise the usage of one or more neural networks, and the obtained measurements may be based, at least in part, on the output of the one or more neural networks. In some embodiments, measuring lengths (664) may comprise analyzing the audio data and/or the preprocessed audio data and/or information associated with a segment of the audio data using one or more regression models.

In some embodiments, measuring lengths (664) may comprise analyzing the audio data and/or the preprocessed audio data to obtain textual information, for example using module 650; and analyzing of the textual information to obtain a measurement associated with the length of one or more segments of the audio data, or a measurement associated with the length of information associated with one or more segments of the audio data. For example, the textual information may comprise a transcription of at least part of the audio data. The transcription may be analyzed in order to identify one or more objects, such as: letters; syllables; morphemes; words; utterances; sentences; questions; conversations; and so forth. The measurement may be based, at least in part, on the number of objects identified within a segment of the transcription, on the number of objects associated with a segment of the audio data, and so forth.

In some examples, the measurement associated with the length of one or more segments of the audio data, and/or the measurement associated with the length of information associated with one or more segments of the audio data, may comprise information related to at least one of: the mean length; the variance of the length; the distribution of lengths; statistics related to the length; histogram of lengths; and so forth.

In some embodiments, identifying context (680) may comprise obtaining context information. For example, identifying context (680) may comprise analyzing input data using one or more rules to identify context information and/or parameters of the context information. For example, the input data may include one or more of: audio data; preprocessed audio data; textual information; visual data; preprocessed visual data; physiological data; preprocessed physiological data; positioning data; preprocessed positioning data; motion data; preprocessed motion data; user input; and so forth. In some examples, at least part of the one or more rules may be read from memory. In some examples, at least part of the one or more rules may be preprogrammed manually. In some examples, at least part of the one or more rules may be the result of training algorithms, such as machine learning algorithms and/or deep learning algorithms, on training examples. The training examples may include examples of input data instances, and in some cases, each input data instance may be labeled with a corresponding desired label and/or result, such as desired context information and/or desired parameters of the context information. In some embodiments, the identification of the context information and/or parameters of the context information may be based, at least in part, on the output of one or more neural networks. In some embodiments, prototypes may be used, the most similar prototype to the input data may be selected, and the context information and/or parameters of the context information may be based, at least in part, on the selected prototype. For example, prototypes may be generated manually. In another example, prototypes may be generated by clustering input data examples, and the centroids of the clusters may be used as prototypes.

In some embodiments, identifying context (680) may comprise analyzing the audio data and/or the preprocessed audio data to identify at least part of the context information. In some examples, identifying context (680) may comprise: analyzing the audio data and/or the preprocessed audio data to obtain textual information, for example using module 650; and analyzing of the textual information to identify context information and/or parameters of the context information. For example, the textual information may comprise a transcription of at least part of the audio data, and natural language processing algorithms may be used to determine context information and/or parameters of the context information. In another example, the textual information may comprise keywords, and the context information and/or parameters of the context information may be determined based on the keywords. In some examples, identifying context (680) may comprise determining the context information and/or parameters of the context information based on prosodic information, such as the prosodic information obtained using module 656.

In some embodiments, identifying context (680) may comprise analyzing the visual data and/or the preprocessed visual data to identify at least part of the context information. For example, the visual data and/or the preprocessed visual data may be analyzed to identify scene information, for example using visual scene recognition algorithms, and the context information and/or parameters of the context information may be based, at least in part, on the scene information. For example, the visual data and/or the preprocessed visual data may be analyzed to identify one or more persons in the environment and/or demographic information related to the one or more persons, for example using face detection and/or face recognition algorithms and/or module 660, and the context information and/or parameters of the context information may be based, at least in part, on the identity of the one or more persons and/or the demographic information related to the one or more persons. For example, the visual data and/or the preprocessed visual data may be analyzed to detect one or more objects in the environment and/or information related to the one or more objects, for example using object detection algorithms, and the context information and/or parameters of the context information may be based, at least in part, on the detected one or more objects and/or the information related to the one or more objects. For example, the visual data and/or the preprocessed visual data may be analyzed to detect one or more activities in the environment and/or information related to the one or more activities, for example using activity detection algorithms, and the context information and/or parameters of the context information may be based, at least in part, on the detected one or more activities and/or the information related to the one or more activities. For example, the visual data and/or the preprocessed visual data may be analyzed to identify text in the environment, for example using optical character recognition algorithms, and the context information and/or parameters of the context information may be based, at least in part, on the identified text.

In some embodiments, identifying context (680) may comprise determining the context information and/or parameters of the context information based, at least in part, on spatial information, such as the spatial information obtained using module 652. In some embodiments, identifying context (680) may comprise determining the context information and/or parameters of the context information based, at least in part, on conversations or information related to conversations, such as the conversations identified using module 658. In some examples, context information and/or parameters of the context information may be based, at least in part, on properties of the identified conversations, such as the length of the conversation, the number of participants in the conversation, the identity of one or more participants, the topics of the conversation, keywords from the conversation, and so forth. In some embodiments, identifying context (680) may comprise determining the context information and/or parameters of the context information based, at least in part, on identifying information associated with one or more speakers, such as identifying information associated with one or more speakers obtained using module 660.

In some embodiments, providing feedbacks (690) may comprise providing one or more feedbacks to one or more users. In some examples, feedback may be provided upon a detection of: an event; an event that matches certain criterions; an event associated with properties that match certain criterions; an assessment result that match certain criterions; an item or object that matches certain criterions; an item or object associated with properties that matches certain criterions; and so forth. In some examples, the nature and/or content of the feedback may depend on: the detected event; the identified properties of the detected event; the detected item; the identified properties of the detected item; the detected object; the identified properties of the detected object; and so forth. In some examples, such events, items and/or objects may be detected by a processing unit, such as processing units 330.

In some embodiments, after providing a first feedback, one or more additional events may be identified. In such cases, providing feedbacks (690) may comprise providing additional feedbacks upon the detection of the additional events. For example, the additional feedbacks may be provided in a similar fashion to the first feedback. In some examples, the system may avoid providing additional similar feedbacks for selected time duration. In some examples, the additional feedback may be identical to the previous feedback. In some examples, the additional feedback may differ from the previous feedback, for example by being of increased intensity, by mentioning the previous feedback, and so forth.

In some embodiments, providing feedbacks (690) may comprise providing one or more feedbacks to one or more users. In some examples, feedbacks may be provided upon the identification of a trigger. In some examples, the nature of the feedback may depend on information associated with the trigger, such as the type of the trigger, properties of the identified trigger, and so forth. Examples of such triggers may include: voice commands, such as voice commands captured using audio sensors 360; press of a button; hand gestures, such as hand gestures captured using image sensors 371; and so forth. In some examples, such triggers may be identified by a processing unit, such as processing units 330.

In some embodiments, providing feedbacks (690) may comprise providing one or more feedbacks as a: visual output, for example using visual outputting units 352; audio output, for example using audio output units 351; tactile output, for example using tactile outputting units 353; electric current output; any combination of the above; and so forth. In some examples, the amount of feedbacks, the events triggering feedbacks, the content of the feedbacks, the nature of the feedbacks, etc., may be controlled by configuration. The feedbacks may be provided: by the apparatus detecting the events; through another apparatus; and so forth. In some examples, the feedbacks may be provided by a wearable apparatus, such as a wearable version of wearable apparatus 300. The feedbacks provided by the wearable apparatus may be provided to: the wearer of the wearable apparatus; one or more caregivers of the wearer of the wearable apparatus; any combination of the above; and so forth.

In some embodiments, providing reports (692) may comprise generating and/or providing one or more reports to one or more users. For example, information may be aggregated, including information related to: detected events; assessment results; identified objects; identified items; and so forth. The information may be aggregated by a processing unit, such as processing units 330. The aggregated information may be stored in memory, such as memory units 320, shared memory modules 520, and so forth. Some examples of such aggregated information may include: a log of detected events, objects, and/or items, possibly together identified properties of the detected events, objects and/or items; statistics related to the detected events, objects, and/or items; statistics related to the identified properties of the detected events, objects, and/or items; and so forth. In some embodiments, providing reports (692) may comprise generating and/or providing one or more reports based on the aggregated information. In some examples, the report may comprise: all or part of the aggregated information; a summary of the aggregated information; information derived from the aggregated information; statistics based on the aggregated information; and so forth. In some examples, the reports may include a comparison of the aggregated information to: past information, such as past performance information; goals; normal range values; and so forth.

In some embodiments, providing reports (692) may comprise providing one or more reports: in a printed form, for example using one or more printers; audibly read, for example using audio outputting units 351; visually displayed, for example using visual outputting units 352; and so forth. In some examples, the reports may be provided by or in conjunction with a wearable apparatus, such as a wearable version of apparatus 300. The generated reports may be provided to: the wearer of the wearable apparatus; one or more caregivers of the wearer of the wearable apparatus; any combination of the above; and so forth.

Figure 7:
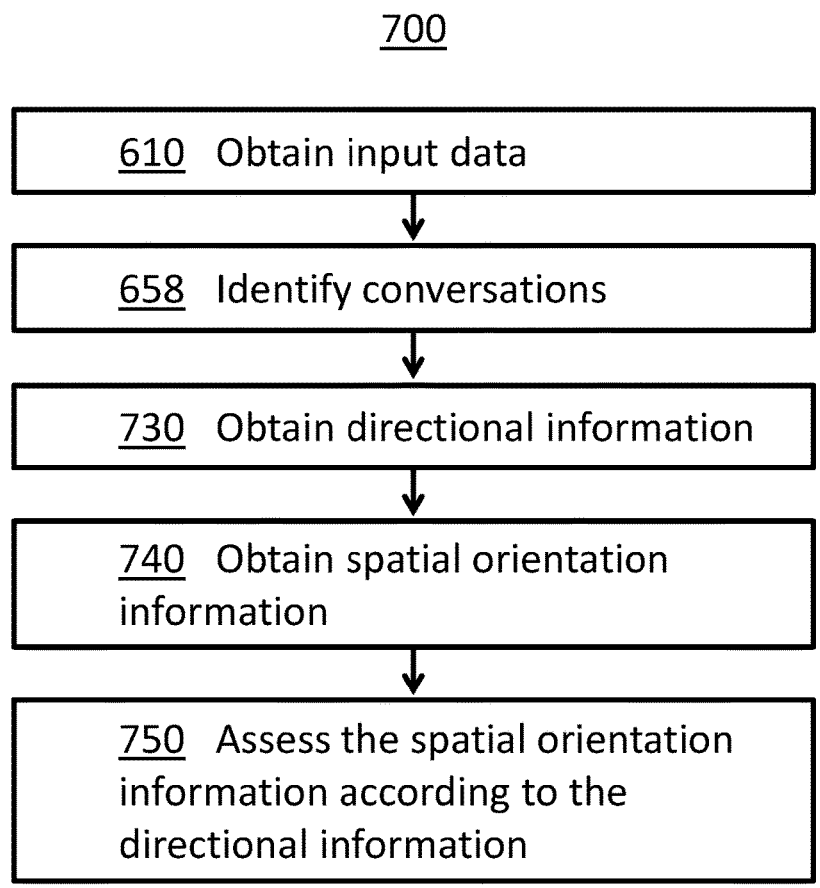
FIG. 7 illustrates an example of a process for analyzing audio to assess spatial orientation.

FIG. 7 illustrates an example of process 700 for analyzing audio to assess spatial orientation. In some examples, process 700, as well as all individual steps therein, may be performed by various aspects of: apparatus 300; server 400; cloud platform 500; computational node 510; and so forth. For example, process 700 may be performed by processing units 330, executing software instructions stored within memory units 320 and/or within shared memory modules 520. In this example, process 700 may comprise: obtaining input data (using module 610); identifying conversations (using module 658); obtaining directional information (Step 730); obtaining spatial orientation information (Step 740); and assessing the spatial orientation information according to the directional information (Step 750). In some implementations, process 700 may comprise one or more additional steps, while some of the steps listed above may be modified or excluded. For example, process 700 may also comprise providing feedbacks (using module 690) and/or providing reports (using module 692). In some implementations, one or more steps illustrated in FIG. 7 may be executed in a different order and/or one or more groups of steps may be executed simultaneously and vice versa. For example, module 658, Step 730, Step 740 and/or Step 750 may be executed after and/or simultaneously with module 610. For example, module 610, module 658, Step 730 and/or Step 740 may be executed before and/or simultaneously with Step 750. For example, module 658, Step 730 and/or Step 740 may be executed before, after and/or simultaneously with one another. Examples of possible execution manners of process 700 may include: continuous execution, returning to the beginning of the process and/or to any step within the process once the process normal execution ends; periodically execution, executing the process at selected times; execution upon the detection of a trigger, where examples of such trigger may include a trigger from a user, a trigger from another process, etc.; any combination of the above; and so forth.

In some embodiments, obtaining directional information (Step 730) may comprise obtaining directional information of a first person with respect to a second person. In some examples, the directional information may comprise at least one of: the relative direction of the first person with respect to the second person; the relative distance of the first person with respect to the second person; the relative position of the first person with respect to the second person; and so forth. In some examples, the first person and the second person may be two speakers engaged in conversation. In some examples, the directional information may vary in time. In some examples, the obtained directional information may be synchronized with the input data, the audio data, the visual data, and so forth. In some examples, obtaining directional information (Step 730) may comprise obtaining directional information of a first person with respect to a second person using module 652. For example, absolute and/or relative locations of the two persons may be obtained using module 652, and the relative direction, distance and/or position of the first person with respect to the second person may be calculated based on the obtained locations. For example, the second person may wear a wearable apparatus, such as a wearable version of apparatus 300, and the relative direction, distance and/or position of the first person with respect to the wearable apparatus may be obtained using module 652, therefore obtaining directional information of the first person with respect to the second person.

In some embodiments, obtaining spatial orientation information (Step 740) may comprise obtaining spatial orientation information associated with a person, such as a the first person and/or the second person of Step 730, a wearer of a wearable apparatus, a speaker, a speaker taking part in a conversation, and so forth. In some examples, obtaining spatial orientation information (Step 740) may comprise obtaining spatial orientation information using module 652.

In some embodiments, assessing the spatial orientation information according to the directional information (Step 750) may comprise assessing spatial orientation information, such as the spatial orientation information obtain by Step 740, according to directional information, such as the directional information obtain by Step 730. In some example, spatial orientation information may be assessed according to directional information to: determine if a person is spatially oriented towards another person; determine if the spatial orientation of a person is socially acceptable, for example for a person engaged in conversation with another person; determine if a person looks in the direction of another person; to determine if a gaze of a person is socially acceptable, for example for a person engaged in conversation with another person; and so forth.

In some examples, assessing the spatial orientation information according to the directional information (Step 750) may comprise comparing a relative direction included in the directional information with a spatial orientation including in the spatial orientation information, for example by calculating the difference between the two directional vectors representing the relative direction and the spatial orientation. In some examples, the difference may be compared with a selected threshold or with a selected range of values to determine if it is socially acceptable. For example, the threshold and/or the range of values may be: predefined; selected based on a relative distance included in the directional information; selected based on a type of interaction the two persons are involved with; based on the type of relationship between the two persons; based on the length and/or type and/or content of the conversation the two persons are involved with; and so forth.

In some embodiments, feedback may be provided to a user based on the assessment of the spatial orientation information associated with a speaker, for example based on the assessment result of Step 750. For example, feedback may be provided when it is determined that the spatial orientation of the speaker is not socially acceptable. As another example, feedback may be provided when it is determined that the gaze of the speaker is not socially acceptable. As an additional example, when it is determined that the spatial orientation of the speaker is socially acceptable, a positive feedback may be provided. The feedback may be provided to a user, for example using module 690.

In some embodiments, information regarding the assessment of the spatial orientation information associated with a speaker may be aggregated, for example the assessment results of Step 750 may be aggregated. In some cases, reports based on the aggregated information may be provided to a user, for example using module 692.

Figure 8A:
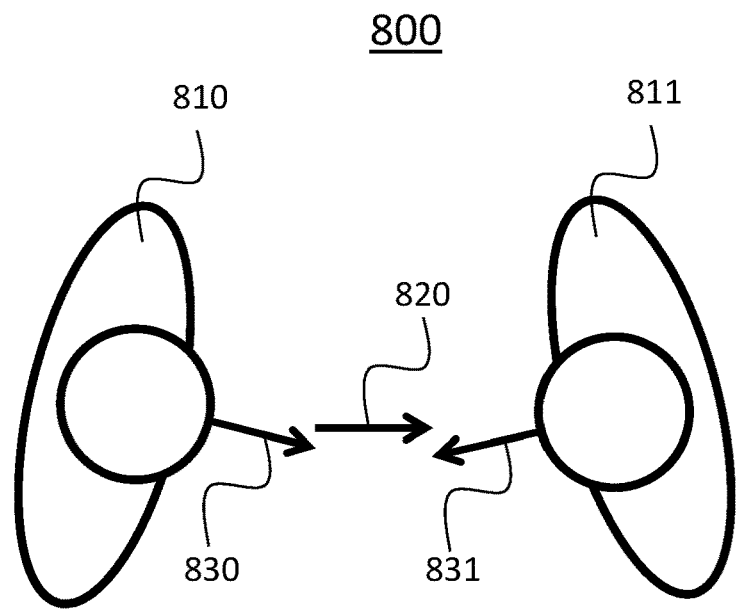
FIGS. 8A and 8B illustrate examples of an environment including two speakers engaged in a conversation.

FIG. 8A illustrates an example of environment 800 including speaker 810 and speaker 811 engaged in a conversation. Arrow 820 shows the relative direction of speaker 811 with respect to speaker 810. Arrow 830 shows a spatial orientation associated with speaker 810. Arrow 831 shows a spatial orientation associated with speaker 811.

Figure 8B:
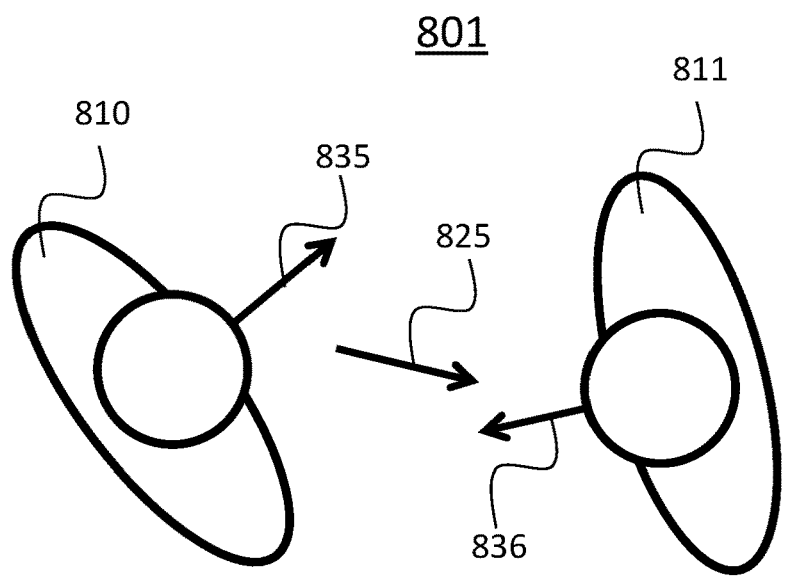

FIG. 8B illustrates an example of environment 801 including speaker 810 and speaker 811 engaged in a conversation. Arrow 825 shows the relative direction of speaker 811 with respect to speaker 810. Arrow 835 shows a spatial orientation associated with speaker 810. Arrow 836 shows a spatial orientation associated with speaker 811.

For example, in scene 800, module 658 may determine that speaker 810 and speaker 811 are engaged in a conversation; Step 730 may obtain relative direction 820 of speaker 811 with respect to speaker 810; Step 740 may obtain spatial orientation 830 associated with speaker 810 and/or spatial orientation 831 associated with speaker 811; and Step 750 may assess spatial orientation 830 associated with speaker 810 and/or spatial orientation 831 associated with speaker 811 according to relative direction 820 of speaker 811 with respect to speaker 810.

For example, in scene 801, module 658 may determine that speaker 810 and speaker 811 are engaged in a conversation; Step 730 may obtain relative direction 825 of speaker 811 with respect to speaker 810; Step 740 may obtain spatial orientation 835 associated with speaker 810 and/or spatial orientation 836 associated with speaker 811; and Step 750 may assess spatial orientation 835 associated with speaker 810 and/or spatial orientation 836 associated with speaker 811 according to relative direction 825 of speaker 811 with respect to speaker 810.

In some examples, it may be determined that the spatial orientation of speaker 810 is socially accepted in scene 800, and that the spatial orientation of speaker 810 is not socially accepted in scene 801, for example based on the angle between relative direction 820 and spatial orientation 830 and/or 831 and on the angle between relative direction 825 and spatial orientation 835 and/or 836. Accordingly, corresponding feedbacks and reports may be provided.

Figure 9:
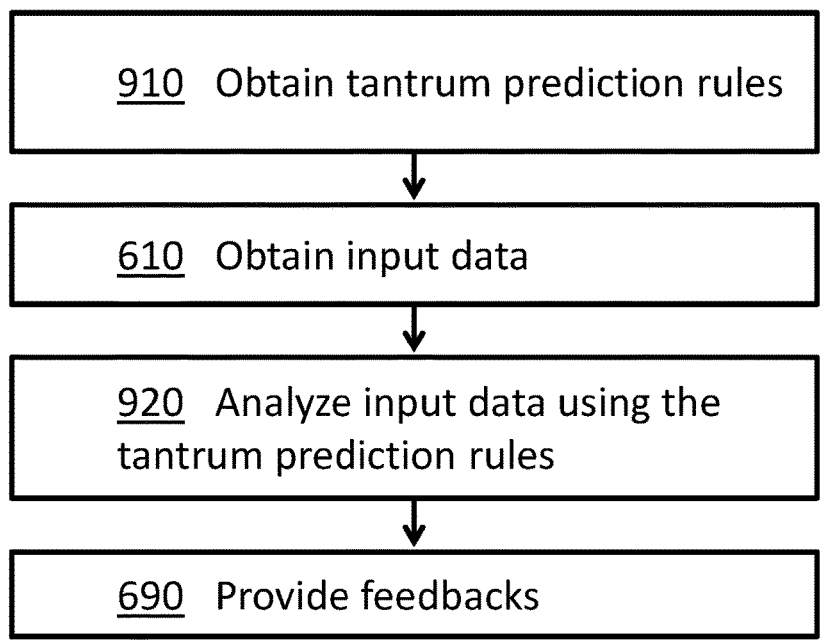
FIG. 9 illustrates an example of a process for predicting tantrums.

FIG. 9 illustrates an example of process 900 for predicting tantrums. In some examples, process 900, as well as all individual steps therein, may be performed by various aspects of: apparatus 300; server 400; cloud platform 500; computational node 510; and so forth. For example, process 900 may be performed by processing units 330, executing software instructions stored within memory units 320 and/or within shared memory modules 520. In this example, process 900 may comprise: obtaining tantrum prediction rules (Step 910); obtaining input data (using module 610); analyzing input data using the tantrum prediction rules (Step 920); and providing feedbacks (using module 690). In some implementations, process 900 may comprise one or more additional steps, while some of the steps listed above may be modified or excluded. For example, Step 910 and/or Step 690 may be excluded from process 900. For example, process 900 may also comprise providing reports (using module 692). In some implementations, one or more steps illustrated in FIG. 9 may be executed in a different order and/or one or more groups of steps may be executed simultaneously and vice versa. For example, Step 910 may be executed before, after and/or simultaneously with module 610. For example, Step 920 and/or module 690 may be executed after and/or simultaneously with Step 910 and/or module 610. For example, Step 920 may be executed before and/or simultaneously with module 690. Examples of possible execution manners of process 900 may include: continuous execution, returning to the beginning of the process and/or to any step within the process once the process normal execution ends; periodically execution, executing the process at selected times; execution upon the detection of a trigger, where examples of such trigger may include a trigger from a user, a trigger from another process, etc.; any combination of the above; and so forth.

In some embodiments, obtaining tantrum prediction rules (Step 910) may comprise obtaining one or more tantrum prediction rules. For example, at least one of the tantrum prediction rules may be read from memory. For example, at least one of the tantrum prediction rules may be received from an external device, for example using a communication device. For example, at least one of the tantrum prediction rules may be preprogrammed manually. In another example, at least one of the tantrum prediction rules may be the result of training machine learning algorithms on training examples, for instance training examples divided to two groups, one group of examples for which the tantrum prediction rules should predict a tantrum, and one group of examples for which the tantrum prediction rules should not predict a tantrum. In some examples, the tantrum prediction rules may be based, at least in part, on the output of one or more neural networks.

In some embodiments, training examples may be identified automatically. For example, once a tantrum is automatically detected, for example using process 1000 and/or Step 1020 (described below), sensor readings preceding the detected tantrum may be used as a training example for a case where the tantrum prediction rules should predict a tantrum. In an additional example, when a tantrum is not detected at a certain time period, sensor readings from the beginning of the time period may be used as a training example for a case where the tantrum prediction rules should not predict a tantrum. In some examples, the automatically detected training examples may be added to an existing corpus of training examples. In some examples, the tantrum prediction rules may be updated based, at least in part, on the automatically identified examples. In some examples, the updated tantrum prediction rules may be specific to a user, for example using training examples based on automatically identified tantrums of the user. In other examples, the updated tantrum prediction rules may be based on training examples of automatically identified tantrums from a number of users.

In some embodiments, analyzing input data using the tantrum prediction rules (Step 920) may comprise analyzing the input data using the tantrum prediction rules to obtain tantrum prediction information. In some examples, analyzing input data using the tantrum prediction rules (Step 920) may comprise analyzing one or more of: the audio data, the preprocessed audio data, the visual data, the preprocessed visual data, the physiological data, the preprocessed physiological data, the motion data, the preprocessed motion data, any combination and/or fusion of the above, and so forth. In some examples, the tantrum prediction information may comprise any combination of: a yes/no tantrum prediction; an estimated time to tantrum; a certainty level associated with the prediction; a predicted degree of the tantrum; a predicted type of the tantrum; and so forth. For example, the tantrum prediction rules may comprise a decision rule and/or a classifier, and the tantrum prediction information may include a yes/no tantrum prediction obtained by using the decision rule and/or a classifier. For example, the tantrum prediction rules may comprise a regression model, and the tantrum prediction information may include an estimated time to tantrum and/or a predicted degree of the tantrum obtained by using the regression models. For example, the tantrum prediction rules may comprise a multiclass classifier, and the tantrum prediction information may include a predicted type of the tantrum obtained by using the multiclass classifier. For example, when using a classifier and/or a regression model, a certainty level associated with the prediction may be based on a certainty level provided by the classifier and/or a regression model.

In some embodiments, analyzing input data using the tantrum prediction rules (Step 920) may comprise analyzing the audio data and/or the preprocessed audio data to obtain textual information, for example using module 650; and analyzing of the textual information to obtain to obtain tantrum prediction information. For example, the textual information may comprise a transcription of at least part of the audio data, and the transcription may be analyzed using: natural language processing algorithms, neural networks algorithms, and so forth. The results of the textual information analysis may be at least part of the input to the tantrum prediction rules.

In some embodiments, analyzing input data using the tantrum prediction rules (Step 920) may comprise analyzing the audio data and/or the preprocessed audio data to obtain prosodic information, for example using module 656; and analyzing of the prosodic information to obtain to obtain tantrum prediction information. For example, the prosodic information may comprise information associated with pitch, intensity, tempo, rhythm, flatness, and so forth. The prosodic information may be at least part of the input to the tantrum prediction rules.

In some embodiments, based on the tantrum prediction information, feedback may be provided to a user, for example using module 690. In some examples, the tantrum prediction information may include a certainty level, and the feedback may be provided when the certainty level exceeds a selected threshold. In some examples, the tantrum prediction information may include an estimated time to tantrum, and the feedback may be provided when the estimated time to tantrum is shorter than a selected threshold. In some examples, the tantrum prediction information may include a predicted degree of the tantrum, and the feedback may be provided when the predicted degree of the tantrum exceeds a selected threshold. In some examples, the tantrum prediction information may include a predicted type of the tantrum, and the feedback may be provided when the predicted type of the tantrum is of a selected group of types. In some examples, the provided feedback may include information associated with and/or based on: an estimated time to tantrum; a certainty level associated with the prediction; a predicted degree of the tantrum; a predicted type of the tantrum; and so forth.

In some embodiments, after providing feedback, a change to the tantrum prediction information may be identified and/or new tantrum prediction information may be obtained. In some examples, additional feedbacks may be provided to a user based on the identified change to the tantrum prediction information and/or the obtained new tantrum prediction information, for example using module 690. In some examples, if and when the additional feedbacks are provided may be determined based, at least in part, on: elapsed time since last feedback; an estimated time to tantrum; a certainty level associated with the prediction; a predicted degree of the tantrum; a predicted type of the tantrum; the change in the estimated time to tantrum; the change in the certainty level associated with the prediction; the change in the predicted degree of the tantrum; the change predicted type of the tantrum; any combination of the above; and so forth. In some examples, the additional feedbacks may include information associated with and/or based on: an estimated time to tantrum; a certainty level associated with the prediction; a predicted degree of the tantrum; a predicted type of the tantrum; the change in the estimated time to tantrum; the change in the certainty level associated with the prediction; the change in the predicted degree of the tantrum; the change predicted type of the tantrum; and so forth. For example, feedback indicating that a previously predicted tantrum was avoided may be provided. For example, feedback indicating that a certainty level associated with a previously predicted tantrum increased and/or decreased may be provided. For example, feedback indicating that an estimated time to tantrum of a previously predicted tantrum changed may be provided. For example, feedback indicating that a predicted degree of the tantrum and/or a predicted degree of the tantrum of a previously predicted tantrum changed may be provided.

In some embodiments, information related to the tantrum predictions may be aggregated. For example, information related to a tantrum prediction may be stored in memory once the tantrum prediction is made and/or after checking whether the prediction was correct, for example using process 1000 and/or Step 1020 (described below). For example, the information may be stored in a log file, in a database, in a data-structure, in a container data-structure, and so forth. In some examples, the aggregated information may comprise one or more of: time of prediction, an estimated time to tantrum, a certainty level associated with the prediction, a predicted degree of the tantrum, a predicted type of the tantrum, indication whether the prediction was correct, and so forth. In some examples, reports based on the aggregated information may be generated and/or provided to one or more users, for example using module 692. For example, a report may comprise at least part of the aggregated information, statistics related to the tantrum predictions, and so forth.

Figure 10:
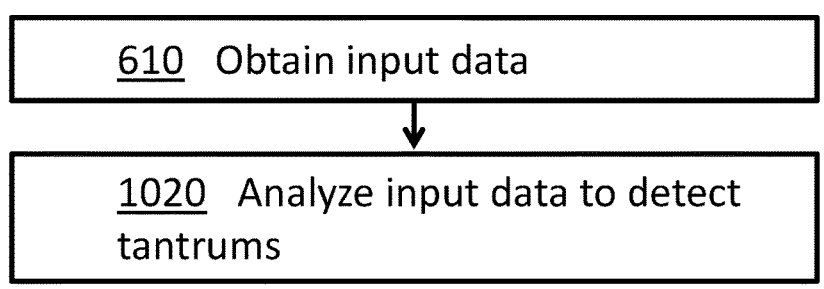
FIG. 10 illustrates an example of a process for analyzing audio to detect tantrums.

FIG. 10 illustrates an example of process 1000 for analyzing audio to detect tantrums. In some examples, process 1000, as well as all individual steps therein, may be performed by various aspects of: apparatus 300; server 400; cloud platform 500; computational node 510; and so forth. For example, process 1000 may be performed by processing units 330, executing software instructions stored within memory units 320 and/or within shared memory modules 520. In this example, process 1000 may comprise: obtaining input data (using module 610); and analyzing input data to detect tantrums (Step 1020). In some implementations, process 1000 may comprise one or more additional steps, while some of the steps listed above may be modified or excluded. For example, process 1000 may also comprise providing feedbacks (using module 690) and/or providing reports (using module 692). In some implementations, one or more steps illustrated in FIG. 10 may be executed in a different order and/or one or more groups of steps may be executed simultaneously and vice versa. For example, Step 1020 may be executed after and/or simultaneously with module 610. Examples of possible execution manners of process 1000 may include: continuous execution, returning to the beginning of the process and/or to Step 1020 once the process normal execution ends; periodically execution, executing the process at selected times; execution upon the detection of a trigger, where examples of such trigger may include a trigger from a user, a trigger from another process, etc.; any combination of the above; and so forth.

In some embodiments, analyzing input data to detect tantrums (Step 1020) may comprise detecting tantrums by analyzing input data, for example by analyzing one or more of: the audio data, the preprocessed audio data, the visual data, the preprocessed visual data, the physiological data, the preprocessed physiological data, the motion data, the preprocessed motion data, any combination and/or fusion of the above, and so forth.

In some embodiments, analyzing input data to detect tantrums (Step 1020) may comprise analyzing the input data to identify one or more properties of the detected tantrums. For example, the tantrum may be identified as: a tantrum of the wearer of the wearable apparatus, a tantrum of another person, and so forth. As another example, the activities involved in the tantrum may be identified, including the identification of: inappropriate stubbornness, crying, screaming, defiance, ranting, hitting, going on a tirade, and so forth. In another example, time related properties of the tantrum may be identified, for instance, the total time length of the tantrum may be measured, for example using module 664.

In some embodiments, the audio data and/or the preprocessed audio data may be analyzed to obtain prosodic information, for example using module 656. For example, the prosodic information may comprise information associated with pitch, intensity, tempo, rhythm, flatness, tone, and so forth. In some examples, the detection of the tantrums and/or the identification of one or more properties of the detected tantrums may be based, at least in part, on the prosodic information. For example, a tantrum detection rule and/or a classifier that identify tantrums may use the prosodic information as input.

In some embodiments, the audio data and/or the preprocessed audio data may be analyzed in order to obtain textual information, for example using module 650; and the detection of the tantrums and/or the identification of one or more properties of the detected tantrums may be based, at least in part, on the textual information. For example, to detect tantrums and/or their properties the textual information may be processed using: natural language processing algorithms, neural networks algorithms, and so forth.

In some embodiments, the motion data and/or the preprocessed motion data may be analyzed to detect tantrums and/or to identify one or more properties of the detected tantrums, for example by identifying erratic motion patterns, by identifying motion patterns indicative of a tantrum, and so forth. For example, a tantrum detection rule and/or classifier that identify tantrums may use the motion information as at least part of the input, for example by using information about the detection of the erratic motion patterns and/or the motion patterns indicative of a tantrum as input.

In some embodiments, the visual data and/or the preprocessed visual data may be analyzed to detect tantrums and/or to identify one or more properties of the detected tantrums, for example by identifying erratic gestures, by identifying activities, by identifying gestures indicative of a tantrum, by identifying ego-motion of the image sensor indicative of a tantrum, and so forth. For example, a tantrum detection rule and/or classifier that identify tantrums may use the visual data as at least part of the input, for example by using information about the detection of the erratic gestures and/or gestures indicative of a tantrum and/or ego-motion of the image sensor indicative of a tantrum as an input.

In some embodiments, the physiological data and/or the preprocessed physiological data may be analyzed to detect tantrums and/or to identify one or more properties of the detected tantrums, for example by identifying physiological conditions indicative of a tantrum. For example, a tantrum detection rule and/or classifier that identify tantrums may use the physiological data as at least part of the input, for example by using information about the detection of the physiological conditions indicative of a tantrum as input.

In some embodiments, analyzing input data to detect tantrums (Step 1020) may comprise analyzing the input data using one or more tantrum detection rules. For example, at least one of the tantrum detection rules may be read from memory. For example, at least one of the tantrum detection rules may be received from an external device, for example using a communication device. For example, at least one of the tantrum detection rules may be preprogrammed manually. For example, at least one of the tantrum detection rules may be the result of training machine learning algorithms on training examples, for instance training examples divided to two groups, one group of examples for which the tantrum detection rules should detect a tantrum, and one group of examples for which the tantrum detection rules should not detect a tantrum. In some examples, the tantrum detection rules may be based, at least in part, on the output of one or more neural networks. In some examples, a regression model may be used to estimate one or more properties of the detected tantrums, such as the tantrum severity.

In some embodiments, feedback may be provided to a user, such as the wearer of the wearable apparatus and/or a caregiver of the wearer, upon the detection of the tantrum, for example using module 690. In some cases, the feedback may be provided upon a detection of a tantrum with identified properties that meet a certain criteria. In some examples, feedback may be provided: when the duration of the tantrum exceeds a certain threshold; when the tantrum involves a specified activity; when the tantrum is a tantrum of the wearer; any combination of the above conditions; and so forth. In some cases, the nature of the feedback may depend on the identified properties of the detected tantrum, such as: ongoing duration of the tantrum; activities involved in the tantrum; and so forth.

In some embodiments, after providing feedback, it may be identified that the tantrum continues. In such cases, additional feedback may be provided. In some examples, additional feedbacks may be provided to a user based on the identified change in the activities involved in the tantrums, on time elapsed, and so forth. In some examples, if and when the additional feedbacks are provided may be determined based, at least in part, on: elapsed time since last feedback; ongoing duration of the tantrum; activities involved in the tantrum; change in the activities involved in the tantrum; and so forth. In some examples, the additional feedbacks may include information associated with and/or based on: elapsed time since last feedback; ongoing duration of the tantrum; activities involved in the tantrum; change in the activities involved in the tantrum; and so forth.

In some embodiments, information related to the detected tantrum may be aggregated. For example, information related to a tantrum may be stored in memory once the tantrum is detected and/or properties of the tantrum are identified, for example in a log file, in a database, in a data-structure, in a container data-structure, and so forth. As more tantrums are detected, the information related to the detected tantrums may be aggregated. In some examples, the aggregated information may comprise one or more of: times at which tantrums were detected; audio and/or video sensors readings recordings of at least part of the tantrums; sensors readings corresponding to at least part of the the time of the tantrums; one or more identified properties of the tantrums, such as the properties listed above; statistics related to the detected tantrums; statistics related to one or more identified properties of the detected tantrums; and so forth. In some examples, reports based on the aggregated information may be generated and/or provided to one or more users, for example using Step 692. For example, a report may comprise statistics related to the detected tantrums. For example, a report may comprise times at which tantrums were detected and/or statistics related to times at which tantrums were detected. For example, a report may comprise one or more identified properties of the tantrums, such as the properties listed above, and/or statistics related to the identified properties.

Figure 11:
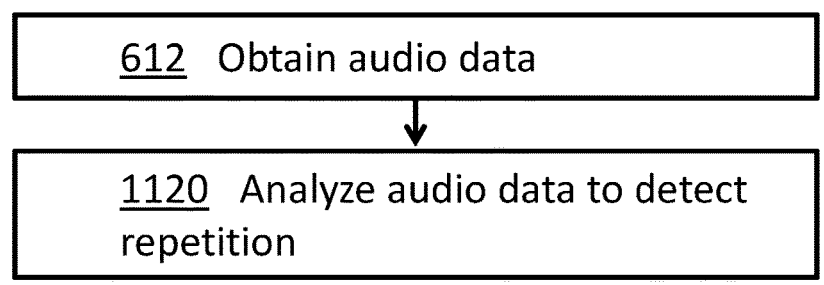
FIG. 11 illustrates an example of a process for analyzing audio to detect repetitions.

FIG. 11 illustrates an example of process 1100 for analyzing audio to detect repetitions. In some examples, process 1100, as well as all individual steps therein, may be performed by various aspects of: apparatus 300; server 400; cloud platform 500; computational node 510; and so forth. For example, process 1100 may be performed by processing units 330, executing software instructions stored within memory units 320 and/or within shared memory modules 520. In this example, process 1100 may comprise: obtaining audio data (using module 612); and analyzing audio data to detect repetition (Step 1120). In some implementations, process 1100 may comprise one or more additional steps, while some of the steps listed above may be modified or excluded. For example, process 1100 may also comprise providing feedbacks (using module 690) and/or providing reports (using module 692). In some implementations, Step 1120 may be executed after and/or simultaneously with module 612. Examples of possible execution manners of process 1100 may include: continuous execution, returning to the beginning of the process and/or to Step 1120 once the process normal execution ends; periodically execution, executing the process at selected times; execution upon the detection of a trigger, where examples of such trigger may include a trigger from a user, a trigger from another process, etc.; any combination of the above; and so forth.

In some embodiments, analyzing audio data to detect repetition (Step 1120) may comprise analyzing the audio data and/or the preprocessed audio data to detect repetitive speech. In some embodiments, analyzing audio data to detect repetition (Step 1120) may comprise analyzing the audio data and/or the preprocessed audio data to detect one or more repetitions in the audio data, each repetition may comprise two or more occurrences of a repeated element. Some examples of the repeated element may include: a sound, a vocalization, speech, a syllable, a number of syllables, a word, a number of words, a utterance, a number of utterances, a phrase, a number of phrases, a sentence, a number of sentences, and so forth.

In some embodiments, analyzing audio data to detect repetition (Step 1120) may also comprise analyzing the audio data and/or the preprocessed audio data to identify one or more properties of the repetition. For example, the number of occurrences of the repeated element may be counted. For example, a repetition may be identified as: a repetition produced by the wearer of a wearable apparatus; a repetition produced by the wearer of sounds originally produced by another person; a repetition produced by the wearer of sounds originally produced by the wearer; a repetition produced by the wearer of sounds originally produced by an inanimate object; a repetition produced by a person other than the wearer; a repetition produced by a person other than the wearer of sounds originally produced by a person other than the wearer; a repetition produced by a person other than the wearer of sounds originally produced by the wearer; a repetition produced by a person other than the wearer of sounds originally produced by an inanimate object; a repetition produced by a person; a repetition produced by a person of sounds originally produced by a person; a repetition produced by an inanimate object of sounds originally produced by a person; a repetition produced by a person of sounds originally produced by an inanimate object; a repetition produced by an inanimate object of sounds originally produced by an inanimate object; and so forth. For example, one or more occurrences of the repeated element may be identified as: occurrences produced by a person; occurrences produced by an inanimate object; occurrences produced by the wearer; occurrences produced by a person other than the wearer; and so forth. As another example, the repetition may be identified as a repetition of a sound, of a vocalization, of speech, of a syllable, of a number of syllables, of a word, of a number of words, of a utterance, of a number of utterances, of a phrase, of a number of phrases, of a sentence, of a number of sentences, and so forth. In some examples, the number of occurrences of the repeated element in a repetition may be counted. In some examples, time related properties may be measured, such as: the total time span of the repetition, the time length of one or more occurrences of the repeated element, the time length of the first occurrence, the time length of the one or more successive occurrences, and so forth.

In some embodiments, analyzing audio data to detect repetition (Step 1120) may also comprise analyzing the audio data and/or the preprocessed audio data to determine if the repetition is socially acceptable, for example as described below. In some embodiments, analyzing audio data to detect repetition (Step 1120) may also comprise analyzing the audio data and/or the preprocessed audio data to determine if the repetition is meaningful, for example as described below.

In some embodiments, analyzing audio data to detect repetition (Step 1120) may comprise: analyzing the audio data and/or the preprocessed audio data to obtain textual information, for example using module 650; and analyzing the obtained textual information. The obtained textual information may be analyzed: to detect repetitive speech, to detect one or more repetitions in the audio data, to identify one or more properties of a repetition, to determine if the repetition is socially acceptable, to determine if the repetition is meaningful, and so forth. In some examples, the textual information may be analyzed using: natural language processing algorithms, neural networks algorithms, machine learning algorithms and/or deep learning algorithms, and so forth.

In some embodiments, analyzing audio data to detect repetition (Step 1120) may comprise analyzing the audio data and/or the preprocessed audio data using one or more rules. The analysis using one or more rules may be used: to detect repetitive speech, to detect one or more repetitions in the audio data, to identify one or more properties of a repetition, to determine if a repetition is socially acceptable, to determine if a repetition is meaningful, and so forth. In some examples, at least part of the one or more rules may be read from memory. In some examples, at least part of the one or more rules may be received from an external device, for example using a communication device. In some examples, at least part of the one or more rules may be preprogrammed manually. In some examples, at least part of the one or more rules may be the result of training algorithms, such as machine learning algorithms and/or deep learning algorithms, on training examples. The training examples may include examples of data instances, and in some cases, each data instance may be labeled with a corresponding desired label and/or result. For example, the training examples may include audio clips with and without repetitions, and the training examples may be labeled accordingly. In an additional example, the training examples may include audio clips that include a repetition, and the training examples may be labeled according to a property of the included repetition. In an additional example, the training examples may include audio clips that include a repetition, and the training examples may be labeled based on the social acceptability of the repetition and/or based on the meaningfulness of the repetition. In some examples, the one or more rules may be based, at least in part, on the output of one or more neural networks. In some embodiments, identifying one or more properties of a repetition may be based, at least in part, on one or more regression models.

In some embodiments, feedback may be provided to a user upon the detection of the repetition, for example using module 690. For example, the feedback may be provided to the wearer of a wearable apparatus, to a caregiver of the wearer of the wearable apparatus, and so forth. In some cases, the feedback may be provided upon the detection of a repetition with identified properties that meet a certain criteria. For example, feedback may be provided: when at least one occurrence of the repeated element is produced by the wearer; when all occurrences of the repeated element are produced by the wearer; when all but the first occurrence of the repeated element are produced by the wearer; when at least one occurrence of the repeated element that is not the first occurrence is produced by the wearer; when the first occurrence is produced by the wearer and at least one successive occurrence is not produced by the wearer; when the number of occurrences of the repeated element exceeds certain threshold; when the number of occurrences of the repeated element that were produced by the wearer exceeds certain threshold; when the duration of some occurrences of the repeated element exceeds certain threshold; when the duration of the occurrences of the repeated element that were produced by the wearer exceeds certain threshold; when the repetition is meaningless; when the repetition is not socially acceptable; when identified properties of the repetition meet a certain condition; when identified properties of the repeated element meet a certain condition; when the repeated element is of a selected type, such as a sound, a vocalization, speech, a syllable, a word, a utterance, a phrase, a sentence, etc.; when identified properties of an occurrence of the repeated element meet a certain condition; any combination of the above; and so forth. In some cases, the nature of the feedback may depend on the identified properties of the detected repetition, of the repeated element, of one or more occurrences of the repeated element, and so forth. For example, the feedback intensity may be controlled based on identified durations, such as one or more of the durations listed above. In an additional example, the feedback may contain visual text and/or audible speech, and the content of the visual text and/or audible speech may be selected based on the type of the repeated element.

In some embodiments, after providing feedback, additional occurrences of the repeated element may be identified. In such cases, an additional feedback may be provided. In some examples, the additional feedback may be provided after the detection of a single additional repetition of the repeated element. In other examples, the additional feedback may be provided after at least a minimal number of additional repetitions of the repeated element are identified. The minimal number may be: predefined, preselected; selected based on past performances; selected based on properties of the repetition; and so forth.

In some embodiments, information related to the detected repetitions may be aggregated. For example, information related to a repetition may be stored in memory once the repetition is detected and/or properties of the repetition are identified. For example, the information may be stored in a log file, in a database, in a data-structure, in a container data-structure, and so forth. As more repetitions are detected, the information related to the detected repetitions may be aggregated. In some examples, the aggregated information may comprise one or more of: times at which repetitions were detected; audio recordings of at least part of the repetitions; one or more identified properties of the repetitions, such as the properties listed above; statistics related to the detected repetitions; statistics related to one or more identified properties of the detected repetitions, such as the properties listed above; and so forth. In some examples, reports based on the aggregated information may be generated and/or provided to one or more users, for example using module 692. For example, a report may comprise statistics related to the detected repetitions. For example, a report may comprise times at which repetitions were detected and/or statistics related to times at which repetitions were detected. For example, a report may comprise one or more identified properties of the repetitions, such as the properties listed above. For example, a report may comprise statistics related to the identified properties.

Figure 12:
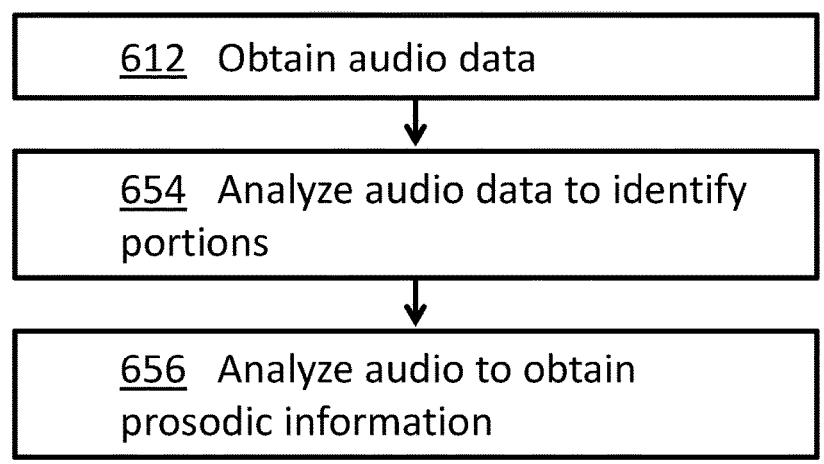
FIG. 12 illustrates an example of a process for analyzing audio to obtain prosodic information.

FIG. 12 illustrates an example of process 1200 for analyzing audio to obtain prosodic information. In some examples, process 1200, as well as all individual steps therein, may be performed by various aspects of: apparatus 300; server 400; cloud platform 500; computational node 510; and so forth. For example, process 1200 may be performed by processing units 330, executing software instructions stored within memory units 320 and/or within shared memory modules 520. In this example, process 1200 may comprise: obtaining audio data (using module 612); analyzing audio data to identify portions (using module 654); and analyzing audio data to obtain prosodic information (using module 656). In some implementations, process 1200 may comprise one or more additional steps, while some of the steps listed above may be modified or excluded. For example, module 654 may be excluded from process 1200. For example, process 1200 may also comprise providing feedbacks (using module 690) and/or providing reports (using module 692). In some implementations, one or more steps illustrated in FIG. 12 may be executed in a different order and/or one or more groups of steps may be executed simultaneously and vice versa. For example, module 654 and/or module 656 may be executed after and/or simultaneously with module 612. For example, module 654 may be executed before, after and/or simultaneously with module 656. Examples of possible execution manners of process 1200 may include: continuous execution, returning to the beginning of the process and/or to any step within the process once the process normal execution ends; periodically execution, executing the process at selected times; execution upon the detection of a trigger, where examples of such trigger may include a trigger from a user, a trigger from another process, etc.; any combination of the above; and so forth.

In some embodiments, feedback may be provided to a user, such as a wearer of the wearable apparatus, based on the prosodic information, for example using module 690. In some cases, the feedback may be provided upon the detection of a segment of the audio data associated with prosodic information that meet a certain criteria. For example, feedback may be provided: when the prosodic information associated with an audio segment produced by the wearer meet a certain criteria; when the prosodic information associated with an audio segment produced by a speaker involved in conversation with the wearer meet a certain criteria; when the duration of the audio segment that is associated with the prosodic information exceeds certain threshold; any combination of the above; and so forth. In some cases, the nature of the feedback may depend on the prosodic information, on the audio segment that is associated with the prosodic information, on a person associated with the prosodic information, and so forth. For example, the nature of the feedback may vary in intensity, in the content of visual text and/or audible speech contained in the feedback, and so forth.

In some embodiments, information related to the identified prosodic information and/or to segments of the audio data associated with the prosodic information may be aggregated, for example the aggregated information may be stored in memory. For example, a record of the prosodic information and/or segment of the audio data associated with the prosodic information may be stored in memory, for example in a log file, in a database, in a data-structure, in a container data-structure, and so forth. As more prosodic information is identified, the prosodic information may be aggregated. In some examples, the aggregated information may comprise one or more of: the prosodic information; information related to a speaker associated with the prosodic information; information related to the segment of the audio data associated with the prosodic information; audio recordings of at least part of the segment of the audio data associated with the prosodic information; statistics related to the prosodic information and/or segments of the audio data associated with the prosodic information; and so forth. In some examples, reports based on the aggregated information may be generated and/or provided to one or more users, for example using module 692. For example, a report may comprise statistics related to the prosodic information and/or segments of the audio data associated with the prosodic information. For example, a report may comprise times at which prosodic information that meets a certain condition was identified, the total duration corresponding to prosodic information that meets a certain condition, and so forth. In some examples, the reports may include a comparison of the aggregated information to: past performances, goals, normal range values, and so forth.

In some embodiments, the audio data and/or the preprocessed audio data may be analyzed in order to obtain prosodic information records associated with different speakers. For example, each prosodic information record may be associated with a specific speaker; each prosodic information record may be associated with a group of speakers; a group of prosodic information records may be associated with a specific speaker; a group of prosodic information records may be associated with a group of speakers; and so forth. Each prosodic information record may be associated with a group of one or more portions of the audio data. For example, a group of portions of the audio data may be identified as associated with a speaker or with a group of speakers. For example, two speaker engaged in conversation may be identified, and two prosodic information records associated with the two speakers may be obtained. For example, a conversation between the wearer of the wearable apparatus and a second person may be identified, a group of prosodic information records associated with the wearer may be obtained, and a group of prosodic information records associated with the second person may be obtained, and so forth.

In some embodiments, one prosodic information record may be assessed according to other prosodic information records. For example, assessing prosodic information records may comprise comparing measurements associated with speech rhythm, speech tempo, pitch, loudness, intonation, linguistic tone, stress, pauses, timbre, and so forth. In some examples, information regarding such assessments may be aggregated. Some examples of such aggregated information may include: a log of assessments; statistics regarding the assessments; and so forth. In some examples, reports based on the aggregated information may be generated. In some examples, the reports may include a comparison of the aggregated information to: past performances, goals, normal range values, and so forth. In some examples, feedbacks based on the assessment may be provided, for example to the wearer of the wearable apparatus. In some cases, the feedback may be provided when the assessment result meet certain criterions. In some cases, the nature and/or content of the feedback may depend on the assessment result.

In some embodiments, the emotional state of a speaker may be estimated based, at least in part, on the prosodic information. For example, the linguistic tone may indicate the state of mind of a speaker, the speaker attitude toward a discussed subject, and so forth. In some examples, feedbacks based on the estimated emotional state may be provided, for example to the wearer of the wearable apparatus. In some cases, the feedback may be provided when the estimated emotional state is a select emotional state, when the estimated emotional states of two speakers meet certain criterions, and so forth. In some cases, the nature and/or content of the feedback may depend on the estimated emotional state. In some examples, estimated emotional state may be aggregated over time, and reports may be provided to a user based on the aggregated information.

In some embodiments, a speaker may be associated with a presentation region, and each portion of the information may be visually presented in the presentation region associated with the speaker associated with that portion. The association of a presentation region with a speaker may be determined based, at least in part, on information associated with spatial orientation and/or position and/or direction associated with the speaker, for example in a way that will overlay information associated with a speaker over or in proximity to the speaker in an augmented reality display system. The spatial orientation and/or position of the speaker may be determined using module 652. For example, graphical symbol indicative of the linguistic tone and/or estimated emotional state of the speaker (such as a smileys, emojis, ideograms, etc.) may be presented according to the presentation region. For example, a color background and/or color scheme and/or color indicator may be presented according to the presentation region to convey the linguistic tone and/or estimated emotional state of the speaker, for example a red color may be used to convey a negative linguistic tone, a blue color may be used to convey a positive linguistic tone, and so forth.

In some embodiments, the prosodic information associated with a speaker may be analyzed to assess how socially appropriate is the prosody of a speaker. For example, a context associated with the prosodic information may be determined, for example using module 680, and the prosodic information may be assessed according to the context. In some examples, the prosodic information may be analyzed using one or more rules to obtain prosodic information, for example to assess how socially appropriate is the prosody of a speaker. In some examples, at least part of the one or more rules may be read from memory. In some examples, at least part of the one or more rules may be received from an external device, for example using a communication device. In some examples, at least part of the one or more rules may be preprogrammed manually. In some examples, at least part of the one or more rules may be the result of training algorithms, such as machine learning algorithms and/or deep learning algorithms, on training examples. The training examples may include examples of data instances, and in some cases, each data instance may be labeled with a corresponding desired label and/or result. For example, the training examples may include prosodic information records and/or context information, and be labeled according to whether it is socially appropriate. In some examples, the identification of the prosodic information may be based, at least in part, on the output of one or more neural networks. In some examples, a regression model may be used to determine the degree of inappropriateness.

In some examples, feedbacks based on whether the prosodic is socially appropriate may be provided, for example to a wearer of the wearable apparatus. In some cases, the feedback may be provided when the prosodic is appropriate and/or is inappropriate, when the appropriate and/or inappropriate prosody is prosody of a specific speaker (such as the wearer, a person engaged in conversation with the wearer, a selected person, etc.), and so forth. In some cases, the nature and/or content of the feedback may depend on the degree of inappropriateness, on the identity of the speaker associated with the appropriate and/or inappropriate prosody, and so forth. In some examples, information regarding the socially appropriateness may be aggregated over time, and reports may be provided to a user based on the aggregated information.

In some embodiments, a conversation between two people may be identified, for example using module 658. For example, a conversation between the wearer of the wearable apparatus and a second person may be identified. Prosodic information associated with one or more of the people engaged in the conversation may be obtained, for example using process 1200 and/or module 656. The distance between the two people may be estimated, for example using module 652. In some examples, feedbacks may be provided, for example to a wearer of the wearable apparatus, based on the obtained prosodic information and/or the estimated distance between the two people. For example, the loudness of the voice of the wearer may be assessed according to the estimated distance, and if the voice is inappropriate to the estimated distance, feedback may be provided to the wearer. After a first feedback is provided, additional feedback may be provided, for example after a certain time duration passed and the inappropriate loudness continuous.

Figure 13:
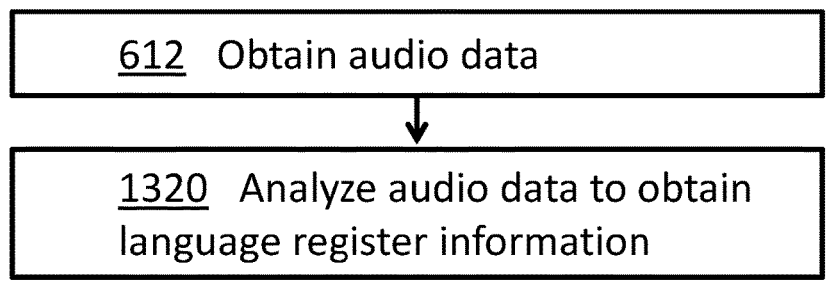
FIG. 13 illustrates an example of a process for analyzing audio to obtain language register information.

FIG. 13 illustrates an example of process 1300 for analyzing audio to obtain language register information. In some examples, process 1300, as well as all individual steps therein, may be performed by various aspects of: apparatus 300; server 400; cloud platform 500; computational node 510; and so forth. For example, process 1300 may be performed by processing units 330, executing software instructions stored within memory units 320 and/or within shared memory modules 520. In this example, process 1300 may comprise: obtaining audio data (using module 612); and analyzing audio data to obtain language register information (Step 1320). In some implementations, process 1300 may comprise one or more additional steps, while some of the steps listed above may be modified or excluded. For example, process 1300 may also comprise providing feedbacks (using module 690) and/or providing reports (using module 692). In some implementations, Step 1320 may be executed after and/or simultaneously with module 612. Examples of possible execution manners of process 1300 may include: continuous execution, returning to the beginning of the process and/or to Step 1320 once the process normal execution ends; periodically execution, executing the process at selected times; execution upon the detection of a trigger, where examples of such trigger may include a trigger from a user, a trigger from another process, etc.; any combination of the above; and so forth.

In some embodiments, analyzing audio data to obtain language register information (Step 1320) may comprise analyzing the audio data and/or the preprocessed audio data to obtain language register information. In some examples, the language register information may be associated with: the entire audio data; with the one or more portions of the audio data, such as one or more portions of the audio identified by module 654; with one or more portions of the audio data associated with a speaker; with one or more portions of the audio data associated with the wearer of a wearable apparatus; with one or more portions of the audio data associated with a group of speakers; with one or more portions of the audio data associated with speakers engaged in conversation with the wearer of the wearable apparatus; and so forth. In some examples, multiple language register information records may be obtained for multiple groups of portions of the audio data. In some examples, a conversation may be identified, for example using module 658, and language register information may be obtained for different speakers engaged in the identified conversation. In some examples, the audio data and/or the preprocessed audio data may be analyzed in order to determine a context associated with the usage of the language register, for example using module 680.

In some embodiments, analyzing audio data to obtain language register information (Step 1320) may comprise analyzing the audio data and/or the preprocessed audio data to determine if and/or when the language register is: an intimate register, a casual register, a formal register, a consultative register, a bench level register, a dialect register, a facetious register, an in house register, an ironic register, a neutral register, a slang register, a taboo register, a technical register, a vulgar register, and so forth. In some examples, the audio data and/or the preprocessed audio data may be analyzed in order to determine the language register type according to ISO 12620 standard.

In some embodiments, analyzing audio data to obtain language register information (Step 1320) may comprise: analyzing the audio data and/or the preprocessed audio data to obtain textual information, for example using module 650; and analyzing the obtained textual information to obtain language register information. For example, the textual information may be analyzed using: natural language processing algorithms, neural networks algorithms, and so forth. For example, the textual information and/or portions of the textual information may be classified using one or more classification rules to determine the language register and/or to determine if the language register is socially acceptable in the current context. For example, the textual information corresponding to a portion of the audio data may be represented in as a bag of words vector, and the bag of words vector may be classified to determine language register, for example using a k-nearest neighbors algorithm, using a nearest centroid classifier algorithm, and so forth.

In some embodiments, analyzing audio data to obtain language register information (Step 1320) may comprise analyzing the audio data and/or the preprocessed audio data using one or more rules to obtain the language register information and/or to determine if the language register is socially acceptable in the current context. In some examples, at least part of the one or more rules may be read from memory. In some examples, at least part of the one or more rules may be received from an external device, for example using a communication device. In some examples, at least part of the one or more rules may be preprogrammed manually. In some examples, at least part of the one or more rules may be the result of training algorithms, such as machine learning algorithms and/or deep learning algorithms, on training examples. The training examples may include examples of data instances, and in some cases, each data instance may be labeled with a corresponding desired label and/or result. For example, the training examples may include audio clips and may be labeled according to the type of the language register of the speech included in the clips. In an additional example, the training examples may include audio clips that include conversations, and the training examples may be labeled based on the social acceptability of the language register of the speakers engaged in the conversation. In some examples, the one or more rules may be based, at least in part, on the output of one or more neural networks.

In some embodiments, feedback may be provided to a user, such as a wearer of the wearable apparatus, based on the language register information, for example using module 690. In some cases, the feedback may be provided upon the detection of language register information that meets a certain criteria, for example that the type of the language register is of a selected language register types. For example, feedback may be provided: when the language register information associated with a specific speaker meets a certain criteria; when the language register information associated with the wearer meets a certain criteria; when the language register information associated with a first speaker meets a certain criteria and the language register information associated with a second speaker meets another criteria; when the language register information associated with a first speaker meets a certain criteria and the language register information associated with a second speaker that is engaged in conversation with the first speaker meets another criteria; when the language register information associated with the wearer meets a certain criteria and the language register information associated with a second speaker meets another criteria; when the language register information associated with the wearer meets a certain criteria and the language register information associated with a speaker that is engaged in conversation with the wearer meets another criteria; when the language register information associated with a speaker that is engaged in conversation with the wearer meets a certain criteria; when the language register of the wearer is not socially acceptable; any combination of the above; and so forth. In some cases, the nature of the feedback may depend on the language register information. For example, the feedback intensity may be control based on the language register information. In an additional example, the feedback may contain visual text and/or audible speech, and the content of the visual text and/or audible speech may be selected based on the language register information. In some examples, the feedback may inform the wearer about the language register of a person that is engaged in conversation with the wearer.

In some embodiments, information related to the obtained language register information may be aggregated. For example, information related to the language register information associated with audio data captured at different times may be aggregated. The aggregated information may be stored in memory, for example in a log file, in a database, in a data-structure, in a container data-structure, and so forth. In some examples, the aggregated information may comprise one or more of: records of the language register information; information related to the speaker associated with the language register information; audio recordings of at least part of the audio data associated with the language register information; and so forth. In some examples, reports based on the aggregated information may be generated and/or provided to one or more users, for example using Step 692. For example, a report may comprise statistics related to the language register information, to the language register of a specific speaker, to the language register of the wearer of the wearable apparatus, to the language register information associated with specific context, and so forth. For example, a report may comprise times at which specific language register information were detected and/or statistics related to these times. In some examples, the reports may include a comparison of the aggregated information to: past performances, goals, normal range values, and so forth.

In some examples, one language register information record may be assessed according to other language register information records. For example, language register information record corresponding to audio data from one point in time may be assessed according to language register information record corresponding to audio data from another point in time. For example, language register information record corresponding to one speaker may be assessed according to language register information record corresponding to another speaker, for example when the two speakers are engaged in conversation, when one of the speakers is a wearer of a wearable apparatus, and so forth. For example, it may be determined if a language register information of a speaker is socially acceptable in a conversation given the language register information of other speakers engaged in the conversation, for example by checking an entry corresponding to the two language register types in a socially acceptable combinations matrix. In some examples, information regarding this assessment may be aggregated. In some examples, information, feedbacks and reports based on the assessment and/or the aggregated information may be provided to a user, for example as described above.

Figure 14:
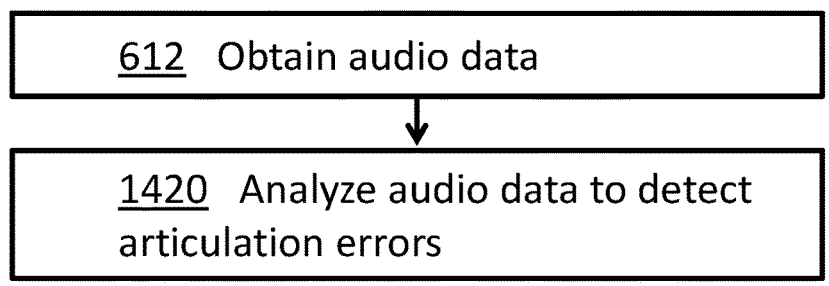
FIG. 14 illustrates an example of a process for analyzing audio to detect articulation errors.

FIG. 14 illustrates an example of process 1400 for analyzing audio to detect articulation errors. In some examples, process 1400, as well as all individual steps therein, may be performed by various aspects of: apparatus 300; server 400; cloud platform 500; computational node 510; and so forth. For example, process 1400 may be performed by processing units 330, executing software instructions stored within memory units 320 and/or within shared memory modules 520. In this example, process 1400 may comprise: obtaining audio data (using module 612); and analyzing audio data to detect articulation errors (Step 1420). In some implementations, process 1400 may comprise one or more additional steps, while some of the steps listed above may be modified or excluded. For example, process 1400 may also comprise providing feedbacks (using module 690) and/or providing reports (using module 692). In some implementations, Step 1420 may be executed after and/or simultaneously with module 612. Examples of possible execution manners of process 1400 may include: continuous execution, returning to the beginning of the process and/or to Step 1420 once the process normal execution ends; periodically execution; executing the process at selected times; execution upon the detection of a trigger, where examples of such trigger may include a trigger from a user, a trigger from another process, etc.; any combination of the above; and so forth.

In some embodiments, analyzing audio data to detect articulation errors (Step 1420) may comprise analyzing the audio data and/or the preprocessed audio data to detect an articulation error. In some examples, one or more properties of the articulation error may also be identified. For example, the articulation error may be identified as: an articulation error produced by the wearer, an articulation error produced by a person other than the wearer, and so forth. As another example, the type of the articulation error may be identified. For example, the audio data and/or the preprocessed audio data may be analyzed to determine that the articulation error is a substitution articulation error, an omission articulation error, a distortion articulation error, an addition articulation error, and so forth. In some examples, the audio data and/or the preprocessed audio data may be analyzed in order to determine the word and/or sentence in which the articulation error occurred. In some examples, the audio data and/or the preprocessed audio data may be analyzed in order to determine the context in which the articulation error occurred, for example using module 680.

In some embodiments, analyzing audio data to detect articulation errors (Step 1420) may comprise: analyzing the audio data and/or the preprocessed audio data to obtain textual information, for example using module 650; and analyzing the obtained textual information to detect articulation errors and/or to determine one or more properties of the detected articulation errors. For example, the textual information may be analyzed using: natural language processing algorithms, neural networks algorithms, spell checkers, and so forth. In some examples, additional information provided by the speech recognition algorithm may be used, such as certainty output associated with different words. In some examples, module 650 may identify a portion of the audio data as corresponding to a certain word in the textual information, and the identified portion of the audio data may be compared with an expected and/or correct articulation of the word, and/or compared with common articulation errors of the word. Based on the comparison results, an articulation error may be detected and/or identified, for example by classifying the articulation of the word as the nearest articulation from the compared articulations.

In some embodiments, analyzing audio data to detect articulation errors (Step 1420) may comprise analyzing the audio data and/or the preprocessed audio data using one or more rules to detect articulation errors and/or to determine one or more properties of the detected articulation errors. In some examples, at least part of the one or more rules may be read from memory. In some examples, at least part of the one or more rules may be received from an external device, for example using a communication device. In some examples, at least part of the one or more rules may be preprogrammed manually. In some examples, at least part of the one or more rules may be the result of training algorithms, such as machine learning algorithms and/or deep learning algorithms, on training examples. The training examples may include examples of data instances, and in some cases, each data instance may be labeled with a corresponding desired label and/or result. For example, the training examples may include audio clips with and without articulation errors, and the training examples may be labeled accordingly. In an additional example, the training examples may include audio clips that include articulation errors, and the training examples may be labeled according to the type of the articulation errors. In some examples, the one or more rules may be based, at least in part, on the output of one or more neural networks.

In some embodiments, feedback may be provided to a user, such as a wearer of the wearable apparatus, upon the detection of an articulation error, for example using module 690. In some cases, the feedback may be provided upon the detection of an articulation error that meets certain criteria. For example, feedback may be provided: when the type of the articulation error is of selected articulation error types; when the articulation error is an articulation error produced by a certain speaker; when the articulation error is an articulation error produced by the wearer; and so forth. For example, feedback may be provided when a context associated with the articulation error meets certain criteria. In some cases, the nature of the feedback may depend on the detected articulation error and/or the context associated with the articulation error. For example, the feedback intensity may be control based on the type of the articulation error. In an additional example, the feedback may contain visual text and/or audible speech, and the content of the visual text and/or audible speech may be selected based on the type of the articulation error.

In some embodiments, after providing feedback, additional articulation error may be detected. In such cases, an additional feedback may be provided. In some examples, the additional feedback may be provided after the detection of a single additional articulation error. In other examples, the additional feedback may be provided after at least a minimal number of additional articulation errors are detected, and feedbacks associated with the intermediate articulation errors may be withheld. The minimal number may be: predefined, preselected; selected based on past performances; selected based on properties of the articulation error; and so forth. In some examples, the additional feedback may be provided after a minimal time has passed since the last feedback and/or since the detection of the first articulation error, and feedbacks associated with the articulation errors within the minimal time period may be withheld. The minimal time may be: predefined, preselected; selected based on past performances; selected based on properties of the articulation error; and so forth. In some examples, the additional feedback may be provided after a minimal number of words and/or sentences have been present and/or detected in the audio data since the last feedback and/or since the detection of the first articulation error, and feedbacks associated with the articulation errors within the minimal number of words and/or sentences may be withheld. The minimal words and/or sentences may be: predefined, preselected; selected based on past performances; selected based on properties of the articulation error; and so forth. The minimal number of words and/or sentences may take into account all words and/or sentences present and/or detected in the audio data, all words and/or sentences spoken by a certain speaker, all words and/or sentences spoken by the wearer, and so forth.

In some embodiments, information related to the detected articulation errors may be aggregated. The aggregated information may be stored in memory unit, for example in a log file, in a database, in a data-structure, in a container data-structure, and so forth. In some examples, the aggregated information may comprise one or more of: information associated with a speaker associated with the articulation error; times at which articulation errors were detected; audio recordings of at least part of the articulation errors; one or more identified properties of the articulation errors, such as the type of the articulation errors; statistics related to the detected articulation errors; statistics related to one or more identified properties of the articulation error; and so forth. In some examples, reports based on the aggregated information may be generated and/or provided to one or more users, for example using module 692. For example, a report may comprise statistics related to the detected articulation errors. For example, a report may comprise times at which articulation errors were detected and/or statistics related to times at which articulation errors were detected. For example, a report may comprise one or more identified properties of the articulation errors, such as the type of the articulation errors, and/or statistics related to the identified properties.

Figure 15:
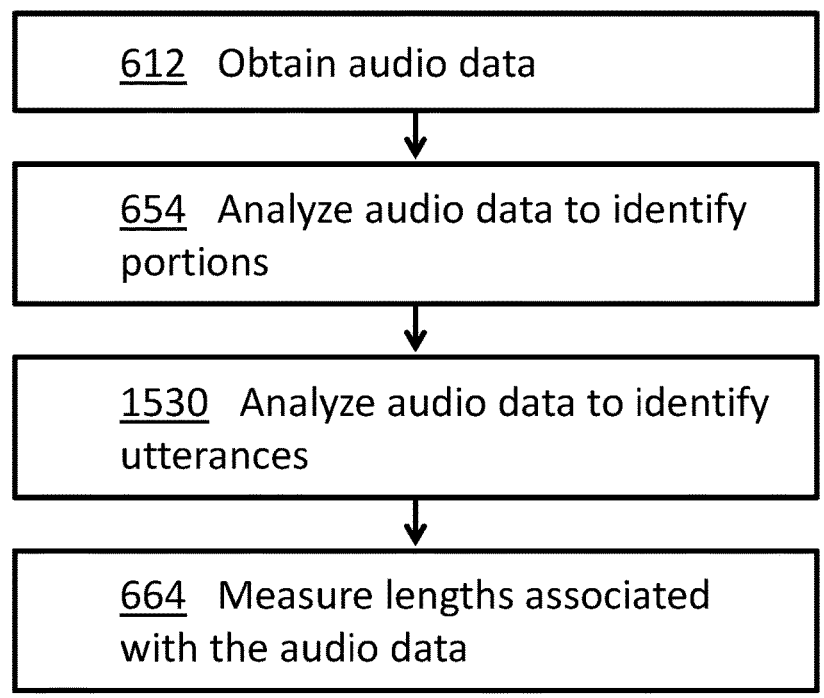
FIG. 15 illustrates an example of a process for analyzing audio to measure length of utterance.

FIG. 15 illustrates an example of process 1500 for analyzing audio to measure length of utterance. In some examples, process 1500, as well as all individual steps therein, may be performed by various aspects of: apparatus 300; server 400; cloud platform 500; computational node 510; and so forth. For example, process 1500 may be performed by processing units 330, executing software instructions stored within memory units 320 and/or within shared memory modules 520. In this example, process 1500 may comprise: obtaining audio data (using module 612); analyzing audio data to identify portions (using module 654); analyzing audio data to identify utterances (Step 1530); and measuring lengths associated with the audio data (using module 664). In some implementations, process 1500 may comprise one or more additional steps, while some of the steps listed above may be modified or excluded. For example, process 1500 may also comprise providing feedbacks (using module 690) and/or providing reports (using module 692). In some implementations, one or more steps illustrated in FIG. 15 may be executed in a different order and/or one or more groups of steps may be executed simultaneously and vice versa. For example, module 654 and/or Step 1530 and/or module 664 may be executed after and/or simultaneously with module 612. For example, module 654 may be executed before, after and/or simultaneously with Step 1530 and/or module 664. Examples of possible execution manners of process 1500 may include: continuous execution, returning to the beginning of the process and/or to any step within the process once the process normal execution ends; periodically execution, executing the process at selected times; execution upon the detection of a trigger, where examples of such trigger may include a trigger from a user, a trigger from another process, etc.; any combination of the above; and so forth.

In some embodiments, analyzing audio data to identify utterances (Step 1530) may comprise analyzing the audio data and/or the preprocessed audio data to identify one or more utterances in the audio data. In some cases, the identified one or more utterances may be associated with the entire audio data. In some cases, the identified one or more utterances may be associated with a group of one or more portions of the audio data, for example with a group of one or more portions of the audio data that were identified as associated with a given speaker (such as a wearer of a wearable device, a person engaged in a conversation with the wearer, etc.), given locations, given regions, given time frames, a given context, conversations with given speakers, conversations regarding given topics, any combination of the above, and so forth.

In some embodiments, the audio data and/or the preprocessed audio data may be analyzed in order to obtain one or more measurements associated with the one or more utterances. In some cases, at least one of the one or more measurements may be associated with the length of the one or more utterances. For example, the length of the one or more utterances may be measured in phonemes, syllables, morphemes or words as described above. In an additional example, the length of the one or more utterances may be associated with the time length of the one or more utterances as described above. In some examples, at least one of the one of the one or more measurements associated with the length of the one or more utterances may comprise at least one of: the mean length of utterance; the variance of the length of utterances; a distribution of the length of utterances; statistics regarding the length of utterances; and so forth.

In some embodiments, feedback may be provided to a wearer of a wearable device upon the detection of one or more measurements that meets certain criterions. The feedbacks may be provided using module 690. For example, when detecting short utterances, the feedback may remind the wearer to use longer utterances. In another example, when detecting short utterances, the feedback may suggest longer alternative utterances to the wearer. In an additional example, when detecting long utterances in certain contexts, the feedback may suggest to the wearer using shorter utterances. In another example, when determining that the wearer is engaged in conversation with a person that may benefit from shorter utterances (such as a child, a person with communication difficulties, etc.), the feedback may suggest shorter alternative utterances to the wearer. In another example, when the wearer may benefit from shorter utterances (such as a child, a person with communication difficulties, etc.), the feedback may repeat one or more utterances said by another person in a form that comprises shorter alternative utterances.

In some embodiments, one or more groups of measurements may be obtained. For example, the audio data and/or the preprocessed audio data may be analyzed in order to identify one or more groups of portions, where each group of portions comprises one or more portions of the audio data. The audio data and/or the preprocessed audio data may be further analyzed to identify one or more groups of utterances, where each group of utterances is associated with one group of portions. The audio data and/or the preprocessed audio data may be further analyzed to obtain the one or more groups of measurements, where each group of measurements comprises one or more measurements associated with one group of utterances. For example, at least one of the one or more groups of measurements may be associated with at least one of: a given speaker (such as a wearer of a wearable device, a person engaged in a conversation with the wearer, etc.), given group of speakers, given locations, given regions, given time frames, a given context, conversations with given speakers, conversations regarding given topics, any combination of the above, and so forth. In some examples, a group of measurements may comprise a single measurement.

In some embodiments, at least two of the one or more groups of measurements may be compared to one another. For example, a group of measurements associated with a first speaker may be compared to a group of measurements associated with a second speaker. For example, a group of measurements associated with a wearer of a wearable device may be compared to a group of measurements associated with a person engaged in conversation with the wearer. In another example, a group of measurements associated with a first time frame may be compared to a group of measurements associated with a second time frame. In an additional example, a group of measurements associated with a first geographical region may be compared to a group of measurements associated with a second geographical region. In another example, a group of measurements associated with a first context may be compared to a group of measurements associated with a second context. In an additional example, a group of measurements associated with conversations regarding a first group of topics may be compared to a group of measurements associated with conversations regarding a second group of topics. In another example, a group of measurements associated with conversations with speakers of a first group of speakers may be compared to a group of measurements associated with conversations with speakers of a second group of speakers. And so forth.

In some examples, one or more groups of measurements may be aggregated, for example in memory. In some examples, statistics regarding the aggregated measurements may be calculated. In some embodiments, reports based on the calculated statistics and/or the aggregated groups of measurements may be generated. The reports may be produced in using module 692. In some examples, the reports may comprise a comparison of the aggregated groups of measurements to: past groups of measurements; goals; normal range values; and so forth. In some cases, the reports may comprise comparisons of at least two of the one or more groups of measurements to one another, such as the comparisons described above. In some embodiments, feedback based on the aggregated groups of measurements may be provided to the wearer. The feedbacks may be provided in using module 690.

Figure 16:
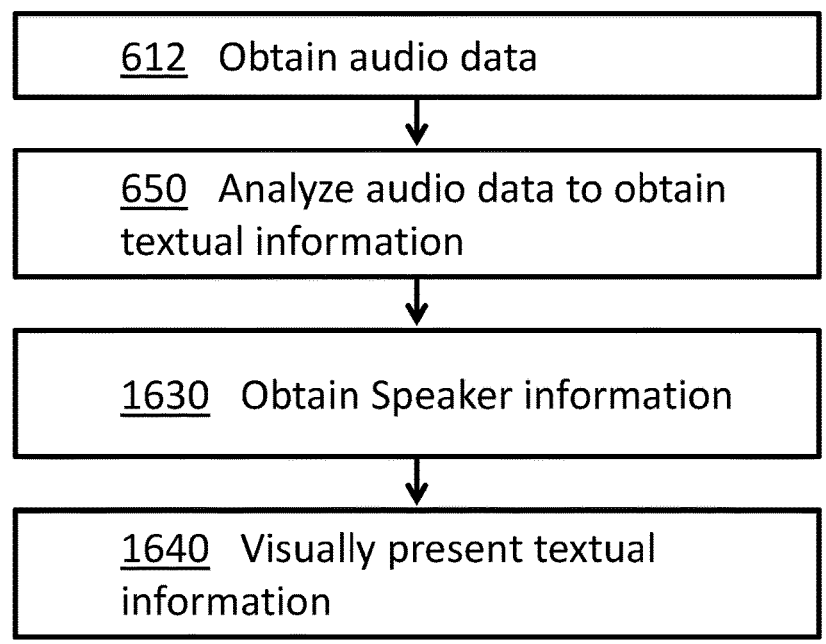
FIG. 16 illustrates an example of a process for visually presenting auditory information.

FIG. 16 illustrates an example of process 1600 for visually presenting auditory information. In some examples, process 1600, as well as all individual steps therein, may be performed by various aspects of: apparatus 300; server 400; cloud platform 500; computational node 510; and so forth. For example, process 1600 may be performed by processing units 330, executing software instructions stored within memory units 320 and/or within shared memory modules 520. In this example, process 1600 may comprise: obtaining audio data (using module 612); analyzing the audio data to obtain textual information (using module 650); obtaining speaker information (Step 1630); and visually presenting textual information (Step 1640). In some implementations, process 1600 may comprise one or more additional steps, while some of the steps listed above may be modified or excluded. In some implementations, one or more steps illustrated in FIG. 16 may be executed in a different order and/or one or more groups of steps may be executed simultaneously and vice versa. For example, module 650 and/or Step 1630 and/or Step 1640 may be executed after and/or simultaneously with module 612. For example, module 650 and/or Step 1630 may be executed before and/or simultaneously with Step 1640. For example, module 650 may be executed before, after and/or simultaneously with Step 1630. Examples of possible execution manners of process 1600 may include: continuous execution, returning to the beginning of the process and/or to module 650, and/or to Step 1630, and/or to Step 1640 once the process normal execution ends; periodically execution, executing the process at selected times; execution upon the detection of a trigger, where examples of such trigger may include a trigger from a user, a trigger from another process, etc.; any combination of the above; and so forth.

In some embodiments, obtaining speaker information (Step 1630) may comprise obtaining speaker information associated with one or more speakers that produced speech and/or sounds in the audio data. In some examples, audio data captured simultaneously using two or more audio sensors and/or the corresponding preprocessed audio data may be analyzed to estimate the location of the source of each sound, for example using sound localization algorithms. The estimated locations may be clustered, and speakers may be identified according to the clustering results. In some examples, visual data and/or preprocessed visual data may be analyzed to identify speakers, speaker's identity, speaker's location, speaker's spatial orientation and so forth. For example, the visual data and/or the preprocessed visual data may be analyzed using face detection algorithms, face recognition algorithms, person detection algorithms, tracking algorithms, lips tracking algorithms, and so forth. In some examples, speaker diarization algorithms may be applied to identify the speaking time of each speaker in the audio data, to associate different speakers with different portions of the audio data and/or with different portions of the information obtained by analyzing the audio data and/or the preprocessed audio data, and so forth.

In some embodiments, visually presenting textual information (Step 1640) may comprise visually presenting to a user information obtained by analyzing the audio data and/or the preprocessed audio data, for example using module 650. In some examples, the information may be visually presented using: an augmented reality display system; a head mounted display system; a tablet screen; a smart watch screen; a mobile phone screen; visual outputting units 352; any combination of the above; and so forth. Textual information may be presented as captions, as a text document that may be continuously updated in real time, in a chat like format, and so forth. Graphical information, such as graphical symbols, may be displayed independently or in conjunction with textual information.

In some embodiments, visually presenting textual information (Step 1640) may comprise visually presenting information obtained by analyzing the audio data and/or the preprocessed audio data to a user according to visual display parameters. In some examples, the entire information may be visually presented according to the same visual display parameters. In some examples, different portions of the information may be visually presented according to different sets of visual display parameters. Some examples of such visual display parameters may include: background color, foreground color, background texture, foreground texture, background image, background video, font, font size, font style, font format, font typefaces, layout, region of the display to perform the visual presentation in, a selection of a visual outputting unit of a plurality of available visual outputting units, and so forth. For example, based on the properties of the voice and/or textual information, it may be determined that a portion of a speech is said in specific linguistic tone; visual display parameters may be selected based on the specific linguistic tone; and the textual information associated with the specific portion of the audio data may be presented using the selected visual display parameters.

In some embodiments, visually presenting textual information (Step 1640) may comprise visually presenting information obtained by analyzing the audio data and/or the preprocessed audio data to a user based, at least in part, on the speaker information obtained by Step 1630. In some examples, the speaker information may comprise an association of portions of the information with speech and sounds produced by the user. In some settings, portions of the information associated with speech and sounds produced by the user will not be visually presented while other portions may be visually presented. In some settings portions of the information associated with speech and sounds produced by the user may be visually presented using a first set of visual display parameters, while other portions may be displayed using other sets of visual display parameters. In some examples, the speaker information may comprise an association of different portions of the information with different speakers, as well as information associated with the speakers, and information associated with a speaker may be visually presented in conjunction with the presentation of portions associated with that speaker. Some examples of information associated with a speaker may include: name, age, picture, information extracted from a social media profile, and so forth. In some examples, the speaker information may comprise an association of different portions of the information with different speakers, and each portion of the information may be visually presented using visual display parameters determined based, at least in part, on the speakers associated with that portion. In some examples, the speaker information may comprise an association of different portions of the information with different speakers, each speaker may be associated with a different presentation region, and each portion of the information may be visually presented in the presentation region associated with the speaker associated with that portion. The association of a presentation region with a speaker may be determined based, at least in part, on information associated with spatial orientation and/or position of the speaker, for example in a way that will overlay information associated with a speaker over or in proximity to the speaker in an augmented reality display system.

In some embodiments, visually presenting textual information (Step 1640) may comprise selectively presenting information obtained by analyzing the audio data and/or the preprocessed audio data visually to a user. In some examples, the system may avoid presenting information associated with speech and sounds produced by the user, or visually present the information associated with speech and sounds produced by the user using a different set of visual display parameters. In some examples, the system may determine which information is associated with speech and sounds that do not involve the user, and avoid presenting that information or visually present that information using a different set of visual display parameters. Some examples of information that is associated with speech and sounds that do not involve the user may include: conversations that do not involve the user; speech not directed at the user; and so forth. The determination that a conversation does not involve the user and/or that a speech is not directed at the user may be based, at least in part, on directional information and spatial orientation information associated with the speakers involved in the conversation or producing the speech, on speaker diarization information, and so forth. For example, directional information and spatial orientation information may be obtained using module 652, speaker diarization information may be obtain using module 658, and so forth.

In some embodiments, visually presenting textual information (Step 1640) may comprise visually presenting information obtained by analyzing the audio data and/or the preprocessed audio data to a user based, at least in part, on properties of voices present in the audio data. In some examples, different portions of the information may be associated with different properties of voices, for example as determined using module 656. In some examples, portions of the information may be visually presented using a set of visual display parameters determined based, at least in part, on the properties of voices associated with that portion. In some examples, information based on properties of a voice present in the audio data may be visually presented in conjunction with the presentation of portions associated with that voice. For example, properties such as pitch, intensity, tempo, rhythm, prosody, and/or flatness of a voice present in a specific portion of the audio data may be identified; information based on the identified properties may be determined; and the determined information may be presented along textual information associated with the specific portion of the audio data. For example, based on the properties of the voice and/or textual information, it may be determined that a portion of a speech is said in specific linguistic tone; and an indication of the linguistic tone may be presented along textual information associated with the specific portion of the audio data. For example, a graphical symbol indicative of the linguistic tone (such as a smileys, emojis, ideograms, etc.) may be presented along textual information associated with the specific portion of the audio data. For example, a color background and/or color scheme and/or color indicator may be presented to convey the linguistic tone of the speaker, for example a red color may be used to convey a negative linguistic tone, a blue color may be used to convey a positive linguistic tone, and so forth.

Figure 17:
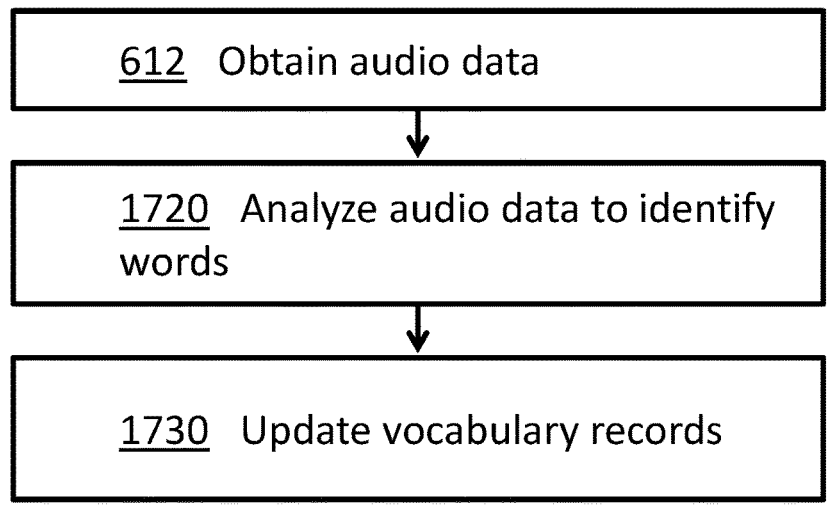
FIG. 17 illustrates an example of a process for analyzing audio to update vocabulary records.

FIG. 17 illustrates an example of process 1700 for analyzing audio to update vocabulary records. In some examples, process 1700, as well as all individual steps therein, may be performed by various aspects of: apparatus 300; server 400; cloud platform 500; computational node 510; and so forth. For example, process 1700 may be performed by processing units 330, executing software instructions stored within memory units 320 and/or within shared memory modules 520. In this example, process 1700 may comprise: obtaining audio data (using module 612); analyzing audio data to identify words (Step 1720); and updating vocabulary records (Step 1730). In some implementations, process 1700 may comprise one or more additional steps, while some of the steps listed above may be modified or excluded. For example, process 1700 may also comprise providing feedbacks (using module 690) and/or providing reports (using module 692). In some implementations, one or more steps illustrated in FIG. 17 may be executed in a different order and/or one or more groups of steps may be executed simultaneously and vice versa. For example, Step 1720 and/or Step 1730 may be executed after and/or simultaneously with module 612. For example, module 612 and/or Step 1720 may be executed before and/or simultaneously with Step 1730. Examples of possible execution manners of process 1700 may include: continuous execution, returning to the beginning of the process and/or to any step within the process once the process normal execution ends; periodically execution, executing the process at selected times; execution upon the detection of a trigger, where examples of such trigger may include a trigger from a user, a trigger from another process, etc.; any combination of the above; and so forth.

In some embodiments, analyzing audio data to identify words (Step 1720) may comprise analyzing the audio data and/or the preprocessed audio data to identify one or more words. In some examples, the one or more words may be associated with the entire audio data. In some examples, the one or more words may be associated with a group of one or more portions of the audio data, for example, a group of one or more portions of the audio data that were identified as associated with: a given speaker, such as the wearer, a person engaged in a conversation with the wearer, etc.; given locations; given regions; given time frames; a given context; conversations with given speakers; conversations regarding given topics; any combination of the above; and so forth. In some examples, the identified one or more words may comprise words present in the audio data. In some examples, the identified one or more words may comprise lemmas of words present in the audio data. In some examples, the identified one or more words may comprise word families of words present in the audio data.

In some embodiments, analyzing audio data to identify words (Step 1720) may comprise analyzing the audio data and/or the preprocessed audio data to identify one or more words associated with a selected speaker, such as the wearer, a person engaged in a conversation with the wearer, and so forth. For example, speech may be identified as associated with a speaker using: pattern recognition algorithms; hidden Markov models based algorithms; mixture of Gaussians based algorithms; pattern matching based algorithms; neural networks based algorithms; quantization based algorithms; machine learning and/or deep learning based algorithms; and so forth. The one or more words may be identified based on speech associated with a desired speaker. For example, analyzing audio data to identify words (Step 1720) may comprise analyzing the audio data and/or the preprocessed audio data to identify one or more words spoken by the wearer.

In some embodiments, analyzing audio data to identify words (Step 1720) may comprise: analyzing the audio data and/or the preprocessed audio data to obtain textual information, for example using module 650; and analyzing the obtained textual information to identify the one or more words. For example, the textual information may be analyzed, for example using natural language processing algorithms, to identify topics and/or keywords in the textual information, and the identified one or more words may comprise the keywords and/or words describing the identified topics. In another example, the identified one or more words may comprise words contained in the textual information.

In some embodiments, one or more vocabulary records may be maintained, for example in memory. For example, one or more vocabulary records may be maintained as a log file, as a database, as a data-structure, as a container data-structure, and so forth. In some examples, at least part of the vocabulary records may be associated with speakers, such as the wearer, a person engaged in a conversation with the wearer, and so forth. In some embodiments, a vocabulary record may comprise information associated with one or more words, for example a list of words used by a speaker associated with the vocabulary record. For example, the information associated with one or more words may comprise the one or more words, lemmas of the one or more words, word families of the one or more words, words describing topics discussed by the speaker, and so forth. In some examples, words in the vocabulary record may be accompanied by contextual information, for example by other words commonly used in conjunction with the words. In some examples, words in the vocabulary record may be accompanied by frequencies, for example by the frequencies at which the speaker associated with the vocabulary record use the words. In some examples, words in the vocabulary record may be accompanied by usage information, for example by the times and/or conversations and/or contextual situations at which the speaker associated with the vocabulary record use the words. For example, the contextual situations may be determined using module 680.

In some embodiments, updating vocabulary records (Step 1730) may comprise updating one or more vocabulary records, for example based on the one or more words identified by Step 1720. In some examples, the vocabulary record to be updated may be selected from one or more vocabulary records stored in memory. For example, the selection of the vocabulary record to be updated may be based on at least one of: the one or more words; identity of speaker of the one or more words; identity of speakers engaged in conversation with the speaker of the one or more words; topic of the conversation; geographical location associated with the one or more words; time associated with the one or more words; speech prosody associated with the one or more words; context information, such as the context information obtained using module 680; context information associated with the one or more words; any combination of the above; and so forth.

In some examples, a vocabulary record may comprise a list of words, and updating vocabulary records (Step 1730) may comprise adding at least part of the one or more words identified by Step 1720 to the list of words. In some examples, vocabulary record may comprise a counter for each word, and updating vocabulary records (Step 1730) may comprise increasing the counters associated with the one or more words identified by Step 1720. In some examples, vocabulary record may comprise contextual information records for words, and updating vocabulary records (Step 1730) may comprise updating the contextual information records associated with the one or more words identified by Step 1720 according to contextual information associated with the one or more words, for example based on the context information obtained using module 680. For example, contextual information may comprise information associated with at least one of: identity of speaker of the one or more words; identity of speakers engaged in conversation with the speaker of the one or more words; topic of the conversation; geographical location associated with the one or more words; time associated with the one or more words; speech prosody associated with the one or more words; and so forth. In some examples, vocabulary records may comprise word co-occurrence information for each word, and updating vocabulary records (Step 1730) may comprise updating the word co-occurrence information according to words that were identified in the audio data in conjunction to the one or more words. In some examples, vocabulary records may comprise information related to the type of words, such as pronouns, nouns, verbs, descriptors, possessives, negatives, demonstratives, question word, and so forth.

In some embodiments, at least two of the one or more vocabulary records may be compared to one another. For example, a vocabulary record associated with a first speaker may be compared to a vocabulary record associated with a second speaker. For example, a vocabulary record associated with the wearer may be compared to a vocabulary record associated with a person engaged in conversation with the wearer. In another example, a vocabulary record associated with a first time frame may be compared to a vocabulary record associated with a second time frame. In an additional example, a vocabulary record associated with a first geographical region may be compared to a vocabulary record associated with a second geographical region. In another example, a vocabulary record associated with a first context may be compared to a vocabulary record associated with a second context. In an additional example, a vocabulary record associated with conversations regarding a first group of topics may be compared to a vocabulary record associated with conversations regarding a second group of topics. In another example, a vocabulary record associated with conversations with speakers of a first group of speakers may be compared to a vocabulary record associated with conversations with speakers of a second group of speakers. And so forth.

In some embodiments, one or more feedbacks may be provided, for example using module 690, based, at least in part, on one or more words, such as the words identified by Step 1720, and/or on one or more vocabulary records, such as the vocabulary records maintained by Step 1730. In some examples, at least one of the words identified by Step 1720 may be selected, for example based on at least one vocabulary record, and the feedback may comprise an interpretation of the selected word. For example, a word spoken by a person engaged in conversation with the wearer may be selected when the word is not included in a vocabulary record associated with the wearer, and an interpretation of that word may be provided. In some examples, at least one of the words identified by Step 1720 may be selected, for example based on at least one vocabulary record, and the feedback may comprise a synonym of the selected word. For example, a word spoken by the wearer may be selected, and a synonym included in a vocabulary record may be provided. In some examples, at least one of the words identified by Step 1720 may be selected, for example based on at least one vocabulary record, and the feedback may comprise information associated with that word. For example, the feedback may include trivia details associated with the selected word. In some examples, the feedbacks may be based on information related to the type of at least one of the one or more words. Some examples of such types may include: pronouns, nouns, verbs, descriptors, possessives, negatives, demonstratives, question word, and so forth. In some examples, the feedbacks may include suggested a usage of a word, a phrase, a sentence, and so forth. In some example, the feedback may include a suggestion of a correct form and/or correct usage of a word, a phrase, a sentence, and so forth.

In some embodiments, one or more reports may be generated and/or provided, for example using module 692, based, at least in part, on one or more words, such as the words identified by Step 1720, and/or on one or more vocabulary records, such as the vocabulary records maintained by Step 1730. For example, the report may comprise at least part of the details included in at least one vocabulary record and/or information inferred from the at least one vocabulary record, such as words, lemmas, word families, topics, frequency of usage of any of the above, contextual information associated with any of the above, and so forth. In some examples, the reports may comprise information related to the type of at least some of the words in a vocabulary record. Some examples of such types may include: as pronouns, nouns, verbs, descriptors, possessives, negatives, demonstratives, question word, and so forth. In some examples, the reports may include a score and/or information related to the usage of grammatical markers. In some examples, the reports may include a comparison of a speaker with other speakers, such as speakers of an age range.

In some examples, the at least one vocabulary record may be selected from one or more vocabulary records stored in memory, and the reports may comprise information from the vocabulary record. In some examples, the reports may comprise a comparison of the vocabulary record to at least one of: past vocabulary records; goals; normal range values; and so forth. For example, the report may comprise at least one of: a comparison of the size of two vocabularies; a comparison of the size of a vocabulary to a goal size; a comparison of the size of a vocabulary to a normal range value according to speaker age; and so forth. In some cases, the reports may comprise comparisons of at least two of the one or more vocabulary records to one another, such as the comparisons described above. In some cases, the reports may comprise suggestions of new words to be used by the speaker. For example, the suggestions of new words may comprise words that are not used by the speaker according to the vocabulary record, but are related to the conversation topics of the conversations the speaker is engaged in.

It will also be understood that the system according to the invention may be a suitably programmed computer, the computer including at least a processing unit and a memory unit. For example, the computer program can be loaded onto the memory unit and can be executed by the processing unit. Likewise, the invention contemplates a computer program being readable by a computer for executing the method of the invention. The invention further contemplates a machine-readable memory tangibly embodying a program of instructions executable by the machine for executing the method of the invention.

What is claimed is:

1. A system for assessing spatial orientation of speakers, the system comprising:
at least one processing unit configured to:
obtain audio data captured by one or more audio sensors;
obtain one or more images captured by one or more image sensors;
analyze the audio data to determine that two speakers are engaged in conversation, the two speakers comprises a first speaker and a second speaker;
obtain directional information associated with a relative direction of the first speaker with respect to the second speaker;
analyze the one or more images to identify a spatial orientation of at least one of a torso, a face and an eye of at least one of the two speakers;
use the obtained directional information and the identified spatial orientation to calculate a difference between the relative direction of the first speaker with respect to the second speaker and the identified spatial orientation of the at least one of a torso, a face and an eye of the at least one of the two speakers to assess the spatial orientation according to the directional information, therefore obtaining spatial orientation assessment; and
provide information based on the calculated difference between the relative direction of the first speaker with respect to the second speaker and the identified spatial orientation of the at least one of a torso, a face and an eye of the at least one of the two speakers.

2. The system of claim 1, wherein the at least one processing unit is further configured to:
compare the calculated difference between the relative direction of the first speaker with respect to the second speaker and the identified spatial orientation of the at least one of a torso, a face and an eye of the at least one of the two speakers with a selected threshold to obtain the spatial orientation assessment; and
provide information based on a result of the comparison of the calculated difference between the relative direction of the first speaker with respect to the second speaker and the identified spatial orientation of the at least one of a torso, a face and an eye of the at least one of the two speakers with a selected threshold.

3. The system of claim 2, wherein the at least one processing unit is further configured to select the threshold based on a type of interaction the two speakers are engaged in.

4. The system of claim 2, wherein the at least one processing unit is further configured to select the threshold based on a type of relationship between the two speakers.

5. The system of claim 2, wherein the at least one processing unit is further configured to:
analyze the audio data to measure a length of the conversation; and
use the measured length to select the threshold.

6. The system of claim 2, wherein the at least one processing unit is further configured to:
analyze the audio data to identify a topic of the conversation; and
use the identified topic to select the threshold.

7. The system of claim 2, wherein the at least one processing unit is further configured to:
analyze the one or more images to produce distance information associated with the distance between the first speaker and the second speaker; and
use the distance information to select the threshold.

8. The system of claim 1, wherein the at least one processing unit is further configured to:
analyze the one or more images to produce distance information associated with the distance between the first speaker and the second speaker; and
assess the spatial orientation according to the directional information and the distance information to obtain the spatial orientation assessment.

9. The system of claim 1, wherein the at least one processing unit is further configured to:
use the calculated difference between the relative direction of the first speaker with respect to the second speaker and the identified spatial orientation of the at least one of a torso, a face and an eye of the at least one of the two speakers to determine whether the first speaker is spatially oriented towards the second speaker; and
use the determination of whether the first speaker is spatially oriented towards the second speaker to produce the spatial orientation assessment.

10. The system of claim 1, wherein the at least one processing unit is further configured to:
analyze the one or more images to identify a spatial orientation of the face of at least one of the two speakers;
calculate a difference between the relative direction of the first speaker with respect to the second speaker and the identified spatial orientation of the face of the at least one of the two speakers; and
provide information based on the calculated difference between the relative direction of the first speaker with respect to the second speaker and the identified spatial orientation of the face of the at least one of the two speakers.

11. The system of claim 1, wherein the one or more audio sensors are included in a wearable apparatus, and wherein the at least one processing unit is further configured to:
use the spatial orientation assessment to determine whether the spatial orientation of the wearer is socially acceptable; and
provide feedback to a wearer of the wearable apparatus when the spatial orientation of the wearer is not socially acceptable.

12. A method for assessing spatial orientation of speakers, the method comprising:
obtaining audio data captured by one or more audio sensors;
obtaining one or more images captured by one or more image sensors;
analyzing the audio data to determine that two speakers are engaged in conversation, the two speakers comprises a first speaker and a second speaker;
obtaining directional information associated with the relative direction of the first speaker with respect to the second speaker;
analyzing the one or more images to identify a spatial orientation of at least one of a torso, a face and an eye of at least one of the two speakers;
using the obtained directional information and the identified spatial orientation to calculate a difference between the relative direction of the first speaker with respect to the second speaker and the identified spatial orientation of the at least one of a torso, a face and an eye of the at least one of the two speakers to assess the spatial orientation according to the directional information, therefore obtaining spatial orientation assessment; and
providing Information based on the calculated difference between the relative direction of the first speaker with respect to the second speaker and the identified spatial orientation of the at least one of a torso, a face and an eye of the at least one of the two speakers.

13. The method of claim 12, further comprising:
comparing the calculated difference between the relative direction of the first speaker with respect to the second speaker and the identified spatial orientation of the at least one of a torso, a face and an eye of the at least one of the two speakers with a selected threshold to obtain the spatial orientation assessment; and
providing information based on a result of the comparison of the calculated difference between the relative direction of the first speaker with respect to the second speaker and the identified spatial orientation of the at least one of a torso, a face and an eye of the at least one of the two speakers with a selected threshold.

14. The method of claim 13, further comprising:
analyzing the audio data to measure a length of the conversation; and
using the measured length to select the threshold.

15. The method of claim 13, further comprising:
analyzing the audio data to identify a topic of the conversation; and
using the identified topic to select the threshold.

16. The method of claim 13, further comprising:
analyzing the one or more images to produce distance information associated with the distance between the first speaker and the second speaker; and
using the distance information to select the threshold.

17. The method of claim 12, further comprising:
analyzing the one or more images to produce distance information associated with the distance between the first speaker and the second speaker; and
assessing the spatial orientation according to the directional information and the distance information to obtain the spatial orientation assessment.

18. The method of claim 12, further comprising:
- analyzing the one or more images to identify a spatial orientation of the eye of at least one of the two speakers;
- calculating a difference between the relative direction of the first speaker with respect to the second speaker and the identified spatial orientation of the eye of the at least one of the two speakers; and
- providing information based on the calculated difference between the relative direction of the first speaker with respect to the second speaker and the identified spatial orientation of the eye of the at least one of the two speakers.

19. The method of claim 12, wherein the one or more audio sensors are included in a wearable apparatus, and further comprising:
- using the spatial orientation assessment to determine whether the gaze of the speaker is socially acceptable; and
- provide feedback to a wearer of the wearable apparatus when the gaze of the speaker is not socially acceptable.

20. A non-transitory computer readable medium storing data and computer implementable instructions for carrying out a method for assessing spatial orientation of speakers, the method comprising:
- obtaining audio data captured by one or more audio sensors;
- obtaining one or more images captured by one or more image sensors;
- analyzing the audio data to determine that two speakers are engaged in conversation, the two speakers comprises a first speaker and a second speaker;
- obtaining directional information associated with the relative direction of the first speaker with respect to the second speaker;
- analyzing the one or more images to identify a spatial orientation of at least one of a torso, a face and an eye of at least one of the two speakers;
- using the obtained directional information and the identified spatial orientation to calculate a difference between the relative direction of the first speaker with respect to the second speaker and the identified spatial orientation of the at least one of a torso, a face and an eye of the at least one of the two speakers to assess the spatial orientation according to the directional information, therefore obtaining spatial orientation assessment; and
- providing information based on the calculated difference between the relative direction of the first speaker with respect to the second speaker and the identified spatial orientation of the at least one of a torso, a face and an eye of the at least one of the two speakers.

* * * * *